US006080400A

United States Patent [19]
Williams et al.

[11] Patent Number: 6,080,400
[45] Date of Patent: Jun. 27, 2000

[54] COMPOSITIONS FOR THE PREVENTION AND TREATMENT OF VEROTOXIN-INDUCED DISEASE

[75] Inventors: James A. Williams, Lincoln, Nebr.; Lisa Marie Byrne, Stoughton, Wis.

[73] Assignee: Ophidian Pharmaceuticals, Inc., Wisconsin

[21] Appl. No.: 08/816,977

[22] Filed: Mar. 13, 1997

Related U.S. Application Data

[63] Continuation-in-part of application No. 08/410,058, Mar. 24, 1995, abandoned.
[51] Int. Cl.$^7$ .......................... A01N 63/00; A61K 39/108
[52] U.S. Cl. .................... 424/93.2; 424/93.4; 424/93.48; 424/241.1
[58] Field of Search .............................. 435/320.1, 69.1, 435/69.7, 91.4, 172.3, 252.3, 7.37; 424/803, 130.1, 164.1, 169.1, 192.1, 134.1, 163.1, 150.1, 236.1, 241.1, 93.2; 530/380; 514/2; 536/23.4, 547

[56] References Cited

U.S. PATENT DOCUMENTS 5,532,142  7/1996  Johnston et al. ........................ 435/69.1

FOREIGN PATENT DOCUMENTS

WO 96/30043  10/1996  WIPO .

OTHER PUBLICATIONS

DWK Acheson et al. Comparison of Shoga–like toxin I B–subunit expression and localization in *E. coli* and *V. cholerae* by using trc or iron–regulated promoter systems. Infect. Immun. 61: 1098–11104, 1993.

DWK Acheson et al. Expression and purification of Shiga–like toxin II B subunits. Infect. Immun. 63: 301–308, 1995.

K. Ramotar et al. Characterization of Shiga–like toxin I B subunit purified from overproducing clones of the SLT–I B cistron. Biochem. J. 272: 805–811, 1990.

TM Zollman et al. Purification of recombinant Shiga–like toxin type I A1 fragment from *E. coli*. Protein Expression and Purification 5: 291–295, 1994.

SB Calderwood et al. A system for production and rapid purification of large amounts of the Shiga toxin/Shiga–like toxin I B subunit. Infect. Immun. 58: 2977–2982, 1990.

I Muhldorfer et al. Regulation of the Shiga–like toxin II operon in *E. coli*. Infect. Immun. 64: 495–502, 1996.

F. Gunzer et al. J. Clin. Microbiol. 31: 2604–2610, 1993.

R. Mierendorf et al. inNovations 1(1): 1–3, 1994.

MP Jackson et al. FEMS microbiol. Lett. 44: 109–114, 1987.

LP Perera et al. Infect. Immun. 59: 829–835, 1991.

*Primary Examiner*—James C. Housel
*Assistant Examiner*—S. Devi
*Attorney, Agent, or Firm*—Medlen & Carroll, LLP

[57] ABSTRACT

The present invention includes methods for generating neutralizing antitoxin directed against verotoxins. In preferred embodiments, the antitoxin directed against these toxins is produced in avian species using soluble recombinant verotoxin proteins. This antitoxin is designed so as to be administrable in therapeutic amounts and may be in any form (i.e., as a solid or in aqueous solution). These antitoxins are useful in the treatment of humans and other animals intoxicated with at least one bacterial toxin, as well as for preventive treatment, and diagnostic assays to detect the presence of toxin in a sample.

2 Claims, 9 Drawing Sheets

SDS-PAGE OF rVT1 AND rVTS rVT1 (LANE 1) AND rVT2 (lane 2). POSITIONS OF MOLECULAR WEIGHT MARKERS (Kda) ARE SHOWN AT THE LEFT. VT COMPONENT POLYPEPTIDES ARE IDENTIFIED AT THE RIGHT.

FIG. 1 rVT1 AND rVT2 TOXICITY IN VERO CELL CULTURE

FIG. 3

WESTREN BLOT REACTIVITY OF rVT1 AND rVT2 ANTIBODIES TO rVT"S

| PANEL A | PANEL B | PANEL C |
|---------|---------|---------|
| 1   2   | 1   2   | 1   2   |

-A
-A1

-A
-A1

-B + A2

-B + A2

IN THIS FIGURE, PANEL A CONTAINS PREIMMUNE IgY, PANEL B CONTAINS rVT1 IgY, AND PANEL C CONTAINS rVT2 IgY. LANE 1 IN EACH PANEL CONTAINS rVT1 (2µg) AND LANE 2 CONTAINS rVT2 (2µg)

FIG. 6

NEUTRALIZATION OF rVT1 CYTOTOXICITY IN VERO CELLS

FIG. 7

NEUTRALIZATION OF rVT2 CYTOTOXICITY IN VERO CELLS

FIG. 8

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
        (A) LENGTH: 945 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..945

(xi) SEQUENCE DESCRIPTION: SEQ ID NO:1:

```
ATG AAA ATA ATT ATT TTT AGA GTG CTA ACT TTT TTC TTT GTT ATC TTT        48
Met Lys Ile Ile Ile Phe Arg Val Leu Thr Phe Phe Phe Val Ile Phe
 1               5                  10                  15

TCA GTT AAT GTG GTG GCG AAG GAA TTT ACC TTA GAC TTC TCG ACT GCA        96
Ser Val Asn Val Val Ala Lys Glu Phe Thr Leu Asp Phe Ser Thr Ala
                20                  25                  30

AAG ACG TAT GTA GAT TCG CTG AAT GTC ATT CGC TCT GCA ATA GGT ACT       144
Lys Thr Tyr Val Asp Ser Leu Asn Val Ile Arg Ser Ala Ile Gly Thr
            35                  40                  45

CCA TTA CAG ACT ATT TCA TCA GGA GGT ACG TCT TTA CTG ATG ATT GAT       192
Pro Leu Gln Thr Ile Ser Ser Gly Gly Thr Ser Leu Leu Met Ile Asp
     50                  55                  60

AGT GGC TCA GGG GAT AAT TTG TTT GCA GTT GAT GTC AGA GGG ATA GAT       240
Ser Gly Ser Gly Asp Asn Leu Phe Ala Val Asp Val Arg Gly Ile Asp
 65                  70                  75                  80

GCA GAG GAA GGG CGG TTT AAT AAT CTA CGG CTT ATT GTT GAA CGA AAT       288
Ala Glu Glu Gly Arg Phe Asn Asn Leu Arg Leu Ile Val Glu Arg Asn
                 85                  90                  95
```

```
AAT TTA TAT GTG ACA GGA TTT GTT AAC AGG ACA AAT AAT GTT TTT TAT      336
Asn Leu Tyr Val Thr Gly Phe Val Asn Arg Thr Asn Asn Val Phe Tyr
            100                 105                 110

CGC TTT GCT GAT TTT TCA CAT GTT ACC TTT CCA GGT ACA ACA GCG GTT      384
Arg Phe Ala Asp Phe Ser His Val Thr Phe Pro Gly Thr Thr Ala Val
            115                 120                 125

ACA TTG TCT GGT GAC AGT AGC TAT ACC ACG TTA CAG CGT GTT GCA GGG      432
Thr Leu Ser Gly Asp Ser Ser Tyr Thr Thr Leu Gln Arg Val Ala Gly
130                 135                 140

ATC AGT CGT ACG GGG ATG CAG ATA AAT CGC CAT TCG TTG ACT ACT TCT      480
Ile Ser Arg Thr Gly Met Gln Ile Asn Arg His Ser Leu Thr Thr Ser
145                 150                 155                 160

TAT CTG GAT TTA ATG TCG CAT AGT GGA ACC TCA CTG ACG CAG TCT GTG      528
Tyr Leu Asp Leu Met Ser His Ser Gly Thr Ser Leu Thr Gln Ser Val
                165                 170                 175

GCA AGA GCG ATG TTA CGG TTT GTT ACT GTG ACA GCT GAA GCT TTA CGT      576
Ala Arg Ala Met Leu Arg Phe Val Thr Val Thr Ala Glu Ala Leu Arg
                180                 185                 190

TTT CGG CAA ATA CAG AGG GGA TTT CGT ACA ACA CTG GAT GAT CTC AGT      624
Phe Arg Gln Ile Gln Arg Gly Phe Arg Thr Thr Leu Asp Asp Leu Ser
            195                 200                 205

GGG CGT TCT TAT GTA ATG ACT GCT GAA GAT GTT GAT CTT ACA TTG AAC      672
Gly Arg Ser Tyr Val Met Thr Ala Glu Asp Val Asp Leu Thr Leu Asn
210                 215                 220

TGG GGA AGG TTG AGT AGC GTC CTG CCT GAC TAT CAT GGA CAA GAC TCT      720
Trp Gly Arg Leu Ser Ser Val Leu Pro Asp Tyr His Gly Gln Asp Ser
225                 230                 235                 240

GTT CGT GTA GGA AGA ATT TCT TTT GGA AGC ATT AAT GCA ATT CTG GGA      768
Val Arg Val Gly Arg Ile Ser Phe Gly Ser Ile Asn Ala Ile Leu Gly
                245                 250                 255

AGC GTG GCA TTA ATA CTG AAT TGT CAT CAT CAT GCA TCG CGA GTT GCC      816
Ser Val Ala Leu Ile Leu Asn Cys His His His Ala Ser Arg Val Ala
                260                 265                 270

AGA ATG GCA TCT GAT GAG TTT CCT TCT ATG TGT CCG GCA GAT GGA AGA      864
Arg Met Ala Ser Asp Glu Phe Pro Ser Met Cys Pro Ala Asp Gly Arg
            275                 280                 285

GTC CGT GGG ATT ACG CAC AAT AAA ATA TTG TGG GAT TCA TCC ACT CTG      912
Val Arg Gly Ile Thr His Asn Lys Ile Leu Trp Asp Ser Ser Thr Leu
290                 295                 300

GGG GCA ATT CTG ATG CGC AGA ACT ATT AGC AGT                          945
Gly Ala Ile Leu Met Arg Arg Thr Ile Ser Ser
305                 310                 315

(2) INFORMATION FOR SEQ ID NO:2:

(i) SEQUENCE CHARACTERISTICS:
        (A) LENGTH: 315 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Ile Ile Ile Phe Arg Val Leu Thr Phe Phe Val Ile Phe
1               5                   10                  15

Ser Val Asn Val Val Ala Lys Glu Phe Thr Leu Asp Phe Ser Thr Ala
            20                  25                  30

Lys Thr Tyr Val Asp Ser Leu Asn Val Ile Arg Ser Ala Ile Gly Thr
        35                  40                  45

Pro Leu Gln Thr Ile Ser Ser Gly Gly Thr Ser Leu Leu Met Ile Asp
    50                  55                  60
```

```
Ser Gly Ser Gly Asp Asn Leu Phe Ala Val Asp Val Arg Gly Ile Asp
 65                  70                  75                  80

Ala Glu Glu Gly Arg Phe Asn Asn Leu Arg Leu Ile Val Glu Arg Asn
                 85                  90                  95

Asn Leu Tyr Val Thr Gly Phe Val Asn Arg Thr Asn Asn Val Phe Tyr
            100                 105                 110

Arg Phe Ala Asp Phe Ser His Val Thr Phe Pro Gly Thr Thr Ala Val
        115                 120                 125

Thr Leu Ser Gly Asp Ser Ser Tyr Thr Thr Leu Gln Arg Val Ala Gly
    130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu Arg
            180                 185                 190

Phe Arg Gln Ile Gln Arg Gly Phe Arg Thr Thr Leu Asp Asp Leu Ser
        195                 200                 205

Gly Arg Ser Tyr Val Met Thr Ala Glu Asp Val Asp Leu Thr Leu Asn
    210                 215                 220

Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly
                245                 250                 255

Ser Val Ala Leu Ile Leu Asn Cys His His His Ala Ser Arg Val Ala
            260                 265                 270

Arg Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser
305                 310                 315
```

(2) INFORMATION FOR SEQ ID NO:3:

(i) SEQUENCE CHARACTERISTICS:
        (A) LENGTH: 267 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..267

(xi) SEQUENCE DESCRIPTION: SEQ ID NO:3:

```
ATG AAA AAA ACA TTA TTA ATA GCT GCA TCG CTT TCA TTT TTT TCA GCA      48
Met Lys Lys Thr Leu Leu Ile Ala Ala Ser Leu Ser Phe Phe Ser Ala
 1               5                  10                  15

AGT GCG CTG GCG ACG CCT GAT TGT GTA ACT GGA AAG GTG GAG TAT ACA      96
Ser Ala Leu Ala Thr Pro Asp Cys Val Thr Gly Lys Val Glu Tyr Thr
            20                  25                  30

AAA TAT AAT GAT GAC GAT ACC TTT ACA GTT AAA GTG GGT GAT AAA GAA     144
Lys Tyr Asn Asp Asp Asp Thr Phe Thr Val Lys Val Gly Asp Lys Glu
        35                  40                  45

TTA TTT ACC AAC AGA TGG AAT CTT CAG TCT CTT CTT CTC AGT GCG CAA     192
```

```
Leu Phe Thr Asn Arg Trp Asn Leu Gln Ser Leu Leu Leu Ser Ala Gln
 50                  55                  60

ATT ACG GGG ATG ACT GTA ACC ATT AAA ACT AAT GCC TGT CAT AAT GGA        240
Ile Thr Gly Met Thr Val Thr Ile Lys Thr Asn Ala Cys His Asn Gly
 65                  70                  75                  80

GGG GGA TTC AGC GAA GTT ATT TTT CGT                                    267
Gly Gly Phe Ser Glu Val Ile Phe Arg
                 85
```

(2) INFORMATION FOR SEQ ID NO:4:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Lys Thr Leu Leu Ile Ala Ala Ser Leu Ser Phe Phe Ser Ala
 1               5                  10                  15

Ser Ala Leu Ala Thr Pro Asp Cys Val Thr Gly Lys Val Glu Tyr Thr
                 20                  25                  30

Lys Tyr Asn Asp Asp Asp Thr Phe Thr Val Lys Val Gly Asp Lys Glu
             35                  40                  45

Leu Phe Thr Asn Arg Trp Asn Leu Gln Ser Leu Leu Leu Ser Ala Gln
 50                  55                  60

Ile Thr Gly Met Thr Val Thr Ile Lys Thr Asn Ala Cys His Asn Gly
 65                  70                  75                  80

Gly Gly Phe Ser Glu Val Ile Phe Arg
                 85
```

(2) INFORMATION FOR SEQ ID NO:5:

(i) SEQUENCE CHARACTERISTICS:
        (A) LENGTH: 954 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..954

(xi) SEQUENCE DESCRIPTION: SEQ ID NO:5:

```
ATG AAG TGT ATA TTA TTT AAA TGG GTA CTG TGC CTG TTA CTG GGT TTT         48
Met Lys Cys Ile Leu Phe Lys Trp Val Leu Cys Leu Leu Leu Gly Phe
 1               5                  10                  15

TCT TCG GTA TCC TAT TCC CGG GAG TTT ACG ATA GAC TTT TCG ACC CAA         96
Ser Ser Val Ser Tyr Ser Arg Glu Phe Thr Ile Asp Phe Ser Thr Gln
                 20                  25                  30

CAA AGT TAT GTC TCT TCG TTA AAT AGT ATA CGG ACA GAG ATA TCG ACC        144
Gln Ser Tyr Val Ser Ser Leu Asn Ser Ile Arg Thr Glu Ile Ser Thr
             35                  40                  45

CCT CTT GAA CAT ATA TCT CAG GGG ACC ACA TCG GTG TCT GTT ATT AAC        192
Pro Leu Glu His Ile Ser Gln Gly Thr Thr Ser Val Ser Val Ile Asn
 50                  55                  60

CAC ACC CAC GGC AGT TAT TTT GCT GTG GAT ATA CGA GGG CTT GAT GTC        240
His Thr His Gly Ser Tyr Phe Ala Val Asp Ile Arg Gly Leu Asp Val
 65                  70                  75                  80

TAT CAG GCG CGT TTT GAC CAT CTT CGT CTG ATT ATT GAG CAA AAT AAT        288
```

```
                Tyr Gln Ala Arg Phe Asp His Leu Arg Leu Ile Ile Glu Gln Asn Asn
                            85                  90                  95

TTA TAT GTG GCA GGG TTC GTT AAT ACG GCA ACA AAT ACT TTC TAC CGT           336
Leu Tyr Val Ala Gly Phe Val Asn Thr Ala Thr Asn Thr Phe Tyr Arg
            100                 105                 110

TTT TCA GAT TTT ACA CAT ATA TCA GTG CCC GGT GTG ACA ACG GTT TCC           384
Phe Ser Asp Phe Thr His Ile Ser Val Pro Gly Val Thr Thr Val Ser
            115                 120                 125

ATG ACA ACG GAC AGC AGT TAT ACC ACT CTG CAA CGT GTC GCA GCG CTG           432
Met Thr Thr Asp Ser Ser Tyr Thr Thr Leu Gln Arg Val Ala Ala Leu
    130                 135                 140

GAA CGT TCC GGA ATG CAA ATC AGT CGT CAC TCA CTG GTT TCA TCA TAT           480
Glu Arg Ser Gly Met Gln Ile Ser Arg His Ser Leu Val Ser Ser Tyr
145                 150                 155                 160

CTG GCG TTA ATG GAG TTC AGT GGT AAT ACA ATG ACC AGA GAT GCA TCC           528
Leu Ala Leu Met Glu Phe Ser Gly Asn Thr Met Thr Arg Asp Ala Ser
                165                 170                 175

AGA GCA GTT CTG CGT TTT GTC ACT GTC ACA GCA GAA GCC TTA CGC TTC           576
Arg Ala Val Leu Arg Phe Val Thr Val Thr Ala Glu Ala Leu Arg Phe
            180                 185                 190

AGG CAG ATA CAG AGA GAA TTT CGT CAG GCA CTG TCT GAA ACT GCT CCT           624
Arg Gln Ile Gln Arg Glu Phe Arg Gln Ala Leu Ser Glu Thr Ala Pro
            195                 200                 205

GTG TAT ACG ATG ACG CCG GGA GAC GTG GAC CTC ACT CTG AAC TGG GGG           672
Val Tyr Thr Met Thr Pro Gly Asp Val Asp Leu Thr Leu Asn Trp Gly
210                 215                 220

CGA ATC AGC AAT GTG CTT CCG GAG TAT CGG GGA GAG GAT GGT GTC AGA           720
Arg Ile Ser Asn Val Leu Pro Glu Tyr Arg Gly Glu Asp Gly Val Arg
225                 230                 235                 240

GTG GGG AGA ATA TCC TTT AAT AAT ATA TCA GCG ATA CTG GGG ACT GTG           768
Val Gly Arg Ile Ser Phe Asn Asn Ile Ser Ala Ile Leu Gly Thr Val
            245                 250                 255

GCC GTT ATA CTG AAT TGC CAT CAT CAG GGG GCG CGT TCT GTT CGC GCC           816
Ala Val Ile Leu Asn Cys His His Gln Gly Ala Arg Ser Val Arg Ala
            260                 265                 270

GTG AAT GAA GAG AGT CAA CCA GAA TGT CAG ATA ACT GGC GAC AGG CCT           864
Val Asn Glu Glu Ser Gln Pro Glu Cys Gln Ile Thr Gly Asp Arg Pro
            275                 280                 285

GTT ATA AAA ATA AAC AAT ACA TTA TGG GAA AGT AAT ACA GCT GCA GCG           912
Val Ile Lys Ile Asn Asn Thr Leu Trp Glu Ser Asn Thr Ala Ala Ala
290                 295                 300

TTT CTG AAC AGA AAG TCA CAG TTT TTA TAT ACA ACG GGT AAA               954
Phe Leu Asn Arg Lys Ser Gln Phe Leu Tyr Thr Thr Gly Lys
305                 310                 315

(2) INFORMATION FOR SEQ ID NO:6:

(i) SEQUENCE CHARACTERISTICS:
        (A) LENGTH: 318 amino acids
        (B) TYPE: amino acid
        (D) TOPOLOGY: linear (ii) MOLECULE TYPE: protein (xi) SEQUENCE DESCRIPTION: SEQ ID NO:6:

Met Lys Cys Ile Leu Phe Lys Trp Val Leu Cys Leu Leu Leu Gly Phe
 1               5                  10                  15

Ser Ser Val Ser Tyr Ser Arg Glu Phe Thr Ile Asp Phe Ser Thr Gln
                20                  25                  30

Gln Ser Tyr Val Ser Ser Leu Asn Ser Ile Arg Thr Glu Ile Ser Thr
            35                  40                  45
```

```
Pro Leu Glu His Ile Ser Gln Gly Thr Thr Ser Val Ser Val Ile Asn
    50                  55                  60

His Thr His Gly Ser Tyr Phe Ala Val Asp Ile Arg Gly Leu Asp Val
 65                  70                  75                  80

Tyr Gln Ala Arg Phe Asp His Leu Arg Leu Ile Ile Glu Gln Asn Asn
                 85                  90                  95

Leu Tyr Val Ala Gly Phe Val Asn Thr Ala Thr Asn Thr Phe Tyr Arg
                100                 105                 110

Phe Ser Asp Phe Thr His Ile Ser Val Pro Gly Val Thr Val Ser
            115                 120                 125

Met Thr Thr Asp Ser Ser Tyr Thr Thr Leu Gln Arg Val Ala Ala Leu
    130                 135                 140

Glu Arg Ser Gly Met Gln Ile Ser Arg His Ser Leu Val Ser Ser Tyr
145                 150                 155                 160

Leu Ala Leu Met Glu Phe Ser Gly Asn Thr Met Thr Arg Asp Ala Ser
                165                 170                 175

Arg Ala Val Leu Arg Phe Val Thr Val Thr Ala Glu Ala Leu Arg Phe
                180                 185                 190

Arg Gln Ile Gln Arg Glu Phe Arg Gln Ala Leu Ser Glu Thr Ala Pro
                195                 200                 205

Val Tyr Thr Met Thr Pro Gly Asp Val Asp Leu Thr Leu Asn Trp Gly
    210                 215                 220

Arg Ile Ser Asn Val Leu Pro Glu Tyr Arg Gly Glu Asp Gly Val Arg
225                 230                 235                 240

Val Gly Arg Ile Ser Phe Asn Asn Ile Ser Ala Ile Leu Gly Thr Val
                245                 250                 255

Ala Val Ile Leu Asn Cys His His Gln Gly Ala Arg Ser Val Arg Ala
            260                 265                 270

Val Asn Glu Glu Ser Gln Pro Glu Cys Gln Ile Thr Gly Asp Arg Pro
            275                 280                 285

Val Ile Lys Ile Asn Asn Thr Leu Trp Glu Ser Asn Thr Ala Ala Ala
    290                 295                 300

Phe Leu Asn Arg Lys Ser Gln Phe Leu Tyr Thr Thr Gly Lys
305                 310                 315

(2) INFORMATION FOR SEQ ID NO:7:

(i) SEQUENCE CHARACTERISTICS:
        (A) LENGTH: 267 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..267

(xi) SEQUENCE DESCRIPTION: SEQ ID NO:7:

ATG AAG AAG ATG TTT ATG GCG GTT TTA TTT GCA TTA GCT TCT GTT AAT        48
Met Lys Lys Met Phe Met Ala Val Leu Phe Ala Leu Ala Ser Val Asn
 1               5                  10                  15

GCA ATG GCG GCG GAT TGT GCT AAA GGT AAA ATT GAG TTT TCC AAG TAT        96
Ala Met Ala Ala Asp Cys Ala Lys Gly Lys Ile Glu Phe Ser Lys Tyr
                20                  25                  30

AAT GAG GAT GAC ACA TTT ACA GTG AAG GTT GAC GGG AAA GAA TAC TGG       144
Asn Glu Asp Asp Thr Phe Thr Val Lys Val Asp Gly Lys Glu Tyr Trp
```

```
              35                  40                  45
ACC AGT CGC TGG AAT CTG CAA CCG TTA CTG CAA AGT GCT CAG TTG ACA          192
Thr Ser Arg Trp Asn Leu Gln Pro Leu Leu Gln Ser Ala Gln Leu Thr
         50                  55                  60

GGA ATG ACT GTC ACA ATC AAA TCC AGT ACC TGT GAA TCA GGC TCC GGA          240
Gly Met Thr Val Thr Ile Lys Ser Ser Thr Cys Glu Ser Gly Ser Gly
 65                  70                  75                  80

TTT GCT GAA GTG CAG TTT AAT AAT GAC                                      267
Phe Ala Glu Val Gln Phe Asn Asn Asp
                 85
```

(2) INFORMATION FOR SEQ ID NO:8:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO:8:

```
Met Lys Lys Met Phe Met Ala Val Leu Phe Ala Leu Ala Ser Val Asn
 1               5                  10                  15

Ala Met Ala Ala Asp Cys Ala Lys Gly Lys Ile Glu Phe Ser Lys Tyr
                 20                  25                  30

Asn Glu Asp Asp Thr Phe Thr Val Lys Val Asp Gly Lys Glu Tyr Trp
                 35                  40                  45

Thr Ser Arg Trp Asn Leu Gln Pro Leu Leu Gln Ser Ala Gln Leu Thr
         50                  55                  60

Gly Met Thr Val Thr Ile Lys Ser Ser Thr Cys Glu Ser Gly Ser Gly
 65                  70                  75                  80

Phe Ala Glu Val Gln Phe Asn Asn Asp
                 85
```

(2) INFORMATION FOR SEQ ID NO:9:

(i) SEQUENCE CHARACTERISTICS:
        (A) LENGTH: 1241 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

```
ATGAAAATAA TTATTTTTAG AGTGCTAACT TTTTTCTTTG TTATCTTTTC AGTTAATGTG     60

GTGGCGAAGG AATTTACCTT AGACTTCTCG ACTGCAAAGA CGTATGTAGA TTCGCTGAAT    120

GTCATTCGCT CTGCAATAGG TACTCCATTA CAGACTATTT CATCAGGAGG TACGTCTTTA    180

CTGATGATTG ATAGTGGCTC AGGGGATAAT TTGTTTGCAG TTGATGTCAG AGGGATAGAT    240

GCAGAGGAAG GCGGTTTAA TAATCTACGG CTTATTGTTG AACGAAATAA TTTATATGTG     300

ACAGGATTTG TTAACAGGAC AAATAATGTT TTTTATCGCT TGCTGATTT TTCACATGTT     360

ACCTTTCCAG GTACAACAGC GGTTACATTG TCTGGTGACA GTAGCTATAC CACGTTACAG    420

CGTGTTGCAG GGATCAGTCG TACGGGGATG CAGATAAATC GCCATTCGTT GACTACTTCT    480

TATCTGGATT TAATGTCGCA TAGTGGAACC TCACTGACGC AGTCTGTGGC AAGAGCGATG    540

TTACGGTTTG TTACTGTGAC AGCTGAAGCT TTACGTTTTC GGCAAATACA GAGGGGATTT    600

CGTACAACAC TGGATGATCT CAGTGGGCGT TCTTATGTAA TGACTGCTGA AGATGTTGAT    660
```

-continued

```
CTTACATTGA ACTGGGGAAG GTTGAGTAGC GTCCTGCCTG ACTATCATGG ACAAGACTCT      720

GTTCGTGTAG GAAGAATTTC TTTTGGAAGC ATTAATGCAA TTCTGGGAAG CGTGGCATTA      780

ATACTGAATT GTCATCATCA TGCATCGCGA GTTGCCAGAA TGGCATCTGA TGAGTTTCCT      840

TCTATGTGTC CGGCAGATGG AAGAGTCCGT GGGATTACGC ACAATAAAAT ATTGTGGGAT      900

TCATCCACTC TGGGGGCAAT TCTGATGCGC AGAACTATTA GCAGTTGAAC AGGGGGTAAA      960

TAAAGGAGTT AAGCATGAAA AAAACATTAT TAATAGCTGC ATCGCTTTCA TTTTTTTCAG     1020

CAAGTGCGCT GGCGACGCCT GATTGTGTAA CTGGAAAGGT GGAGTATACA AAATATAATG     1080

ATGACGATAC CTTTACAGTT AAAGTGGGTG ATAAAGAATT ATTTACCAAC AGATGGAATC     1140

TTCAGTCTCT TCTTCTCAGT GCGCAAATTA CGGGGATGAC TGTAACCATT AAAACTAATG     1200

CCTGTCATAA TGGAGGGGGA TTCAGCGAAG TTATTTTTCG T                        1241
```

(2) INFORMATION FOR SEQ ID NO:10:

(i) SEQUENCE CHARACTERISTICS:
        (A) LENGTH: 1235 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

```
ATGAAGTGTA TATTATTTAA ATGGGTACTG TGCCTGTTAC TGGGTTTTTC TTCGGTATCC       60

TATTCCCGGG AGTTTACGAT AGACTTTTCG ACCCAACAAA GTTATGTCTC TTCGTTAAAT      120

AGTATACGGA CAGAGATATC GACCCCTCTT GAACATATAT CTCAGGGGAC ACATCGGTG      180

TCTGTTATTA ACCACACCCA CGGCAGTTAT TTTGCTGTGG ATATACGAGG GCTTGATGTC      240

TATCAGGCGC GTTTTGACCA TCTTCGTCTG ATTATTGAGC AAAATAATTT ATATGTGGCA      300

GGGTTCGTTA ATACGGCAAC AAATACTTTC TACCGTTTTT CAGATTTTAC ACATATATCA      360

GTGCCCGGTG TGACAACGGT TTCCATGACA ACGGACAGCA GTTATACCAC TCTGCAACGT      420

GTCGCAGCGC TGGAACGTTC CGGAATGCAA ATCAGTCGTC ACTCACTGGT TTCATCATAT      480

CTGGCGTTAA TGGAGTTCAG TGGTAATACA ATGACCAGAG ATGCATCCAG AGCAGTTCTG      540

CGTTTTGTCA CTGTCACAGC AGAAGCCTTA CGCTTCAGGC AGATACAGAG AGAATTTCGT      600

CAGGCACTGT CTGAAACTGC TCCTGTGTAT ACGATGACGC CGGGAGACGT GGACCTCACT      660

CTGAACTGGG GGCGAATCAG CAATGTGCTT CCGGAGTATC GGGGAGAGGA TGGTGTCAGA      720

GTGGGGAGAA TATCCTTTAA TAATATATCA GCGATACTGG GGACTGTGGC CGTTATACTG      780

AATTGCCATC ATCAGGGGGC GCGTTCTGTT CGCGCCGTGA ATGAAGAGAG TCAACCAGAA      840

TGTCAGATAA CTGGCGACAG GCCTGTTATA AAAATAAACA ATACATTATG GGAAAGTAAT      900

ACAGCTGCAG CGTTTCTGAA CAGAAAGTCA CAGTTTTTAT ATACAACGGG TAAATAAAGG      960

AGTTAAGCAT GAAGAAGATG TTTATGGCGG TTTTATTTGC ATTAGCTTCT GTTAATGCAA     1020

TGGCGGCGGA TTGTGCTAAA GGTAAAATTG AGTTTTCCAA GTATAATGAG GATGACACAT     1080

TTACAGTGAA GGTTGACGGG AAAGAATACT GGACCAGTCG CTGGAATCTG CAACCGTTAC     1140

TGCAAAGTGC TCAGTTGACA GGAATGACTG TCACAATCAA ATCCAGTACC TGTGAATCAG     1200

GCTCCGGATT TGCTGAAGTG CAGTTTAATA ATGAC                                1235
```

(2) INFORMATION FOR SEQ ID NO:11:

(i) SEQUENCE CHARACTERISTICS:

(A) LENGTH: 8 amino acids
                (B) TYPE: amino acid
                (C) STRANDEDNESS: unknown
                (D) TOPOLOGY: linear (ii) MOLECULE TYPE: peptide (xi) SEQUENCE DESCRIPTION: SEQ ID NO:11:

Leu Glu His His His His His His
1               5

(2) INFORMATION FOR SEQ ID NO:12:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:12:

GCCATATGAA AATAATTATT TTTAGAGTG                                      29

(2) INFORMATION FOR SEQ ID NO:13:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:13:

GGCTCGAGAC TGCTAATAGT TCTGCGCAT                                      29

(2) INFORMATION FOR SEQ ID NO:14:

(i) SEQUENCE CHARACTERISTICS:
                (A) LENGTH: 28 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:14:

GCCATATGAA AAAAACATTA TTAATAGC                                       28

(2) INFORMATION FOR SEQ ID NO:15:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:15:

GGCTCGAGAC GAAAAATAAC TTCGCTGAA                                      29

(2) INFORMATION FOR SEQ ID NO:16:

(i) SEQUENCE CHARACTERISTICS:
                (A) LENGTH: 29 base pairs
                (B) TYPE: nucleic acid
                (C) STRANDEDNESS: single (D) TOPOLOGY: linear (ii) MOLECULE TYPE: DNA (genomic)

(xi) SEQUENCE DESCRIPTION: SEQ ID NO:16:

GCCATATGAA GTGTATATTA TTTAAATGG                                          29

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GGCTCGAGTT TACCCGTTGT ATATAAAAAC                                         30

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CGCATATGAA GAAGATGTTT ATGGCG                                             26

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGCTCGAGGT CATTATTAAA CTGCACTTC                                          29

(2) INFORMATION FOR SEQ ID NO:20:

(i) SEQUENCE CHARACTERISTICS:
        (A) LENGTH: 969 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..969

(xi) SEQUENCE DESCRIPTION: SEQ ID NO:20:

ATG AAA ATA ATT ATT TTT AGA GTG CTA ACT TTT TTC TTT GTT ATC TTT          48
Met Lys Ile Ile Ile Phe Arg Val Leu Thr Phe Phe Phe Val Ile Phe
1               5                   10                  15

TCA GTT AAT GTG GTG GCG AAG GAA TTT ACC TTA GAC TTC TCG ACT GCA          96
Ser Val Asn Val Val Ala Lys Glu Phe Thr Leu Asp Phe Ser Thr Ala
                20                  25                  30

AAG ACG TAT GTA GAT TCG CTG AAT GTC ATT CGC TCT GCA ATA GGT ACT         144

```
Lys Thr Tyr Val Asp Ser Leu Asn Val Ile Arg Ser Ala Ile Gly Thr
         35                  40                  45

CCA TTA CAG ACT ATT TCA TCA GGA GGT ACG TCT TTA CTG ATG ATT GAT            192
Pro Leu Gln Thr Ile Ser Ser Gly Gly Thr Ser Leu Leu Met Ile Asp
     50                  55                  60

AGT GGC TCA GGG GAT AAT TTG TTT GCA GTT GAT GTC AGA GGG ATA GAT            240
Ser Gly Ser Gly Asp Asn Leu Phe Ala Val Asp Val Arg Gly Ile Asp
 65                  70                  75                  80

GCA GAG GAA GGG CGG TTT AAT AAT CTA CGG CTT ATT GTT GAA CGA AAT            288
Ala Glu Glu Gly Arg Phe Asn Asn Leu Arg Leu Ile Val Glu Arg Asn
                 85                  90                  95

AAT TTA TAT GTG ACA GGA TTT GTT AAC AGG ACA AAT AAT GTT TTT TAT            336
Asn Leu Tyr Val Thr Gly Phe Val Asn Arg Thr Asn Asn Val Phe Tyr
             100                 105                 110

CGC TTT GCT GAT TTT TCA CAT GTT ACC TTT CCA GGT ACA ACA GCG GTT            384
Arg Phe Ala Asp Phe Ser His Val Thr Phe Pro Gly Thr Thr Ala Val
         115                 120                 125

ACA TTG TCT GGT GAC AGT AGC TAT ACC ACG TTA CAG CGT GTT GCA GGG            432
Thr Leu Ser Gly Asp Ser Ser Tyr Thr Thr Leu Gln Arg Val Ala Gly
 130                 135                 140

ATC AGT CGT ACG GGG ATG CAG ATA AAT CGC CAT TCG TTG ACT ACT TCT            480
Ile Ser Arg Thr Gly Met Gln Ile Asn Arg His Ser Leu Thr Thr Ser
145                 150                 155                 160

TAT CTG GAT TTA ATG TCG CAT AGT GGA ACC TCA CTG ACG CAG TCT GTG            528
Tyr Leu Asp Leu Met Ser His Ser Gly Thr Ser Leu Thr Gln Ser Val
                 165                 170                 175

GCA AGA GCG ATG TTA CGG TTT GTT ACT GTG ACA GCT GAA GCT TTA CGT            576
Ala Arg Ala Met Leu Arg Phe Val Thr Val Thr Ala Glu Ala Leu Arg
             180                 185                 190

TTT CGG CAA ATA CAG AGG GGA TTT CGT ACA ACA CTG GAT GAT CTC AGT            624
Phe Arg Gln Ile Gln Arg Gly Phe Arg Thr Thr Leu Asp Asp Leu Ser
         195                 200                 205

GGG CGT TCT TAT GTA ATG ACT GCT GAA GAT GTT GAT CTT ACA TTG AAC            672
Gly Arg Ser Tyr Val Met Thr Ala Glu Asp Val Asp Leu Thr Leu Asn
 210                 215                 220

TGG GGA AGG TTG AGT AGC GTC CTG CCT GAC TAT CAT GGA CAA GAC TCT            720
Trp Gly Arg Leu Ser Ser Val Leu Pro Asp Tyr His Gly Gln Asp Ser
225                 230                 235                 240

GTT CGT GTA GGA AGA ATT TCT TTT GGA AGC ATT AAT GCA ATT CTG GGA            768
Val Arg Val Gly Arg Ile Ser Phe Gly Ser Ile Asn Ala Ile Leu Gly
                 245                 250                 255

AGC GTG GCA TTA ATA CTG AAT TGT CAT CAT CAT GCA TCG CGA GTT GCC            816
Ser Val Ala Leu Ile Leu Asn Cys His His His Ala Ser Arg Val Ala
             260                 265                 270

AGA ATG GCA TCT GAT GAG TTT CCT TCT ATG TGT CCG GCA GAT GGA AGA            864
Arg Met Ala Ser Asp Glu Phe Pro Ser Met Cys Pro Ala Asp Gly Arg
         275                 280                 285

GTC CGT GGG ATT ACG CAC AAT AAA ATA TTG TGG GAT TCA TCC ACT CTG            912
Val Arg Gly Ile Thr His Asn Lys Ile Leu Trp Asp Ser Ser Thr Leu
 290                 295                 300

GGG GCA ATT CTG ATG CGC AGA ACT ATT AGC AGT CTC GAG CAC CAC CAC            960
Gly Ala Ile Leu Met Arg Arg Thr Ile Ser Ser Leu Glu His His His
305                 310                 315                 320

CAC CAC CAC                                                                969
His His His (2) INFORMATION FOR SEQ ID NO:21:

(i) SEQUENCE CHARACTERISTICS:
        (A) LENGTH: 323 amino acids
```

```
            (B) TYPE: amino acid
            (D) TOPOLOGY: linear (ii) MOLECULE TYPE: protein (xi) SEQUENCE DESCRIPTION: SEQ ID NO:21:

Met Lys Ile Ile Ile Phe Arg Val Leu Thr Phe Phe Val Ile Phe
 1               5                  10                  15

Ser Val Asn Val Val Ala Lys Glu Phe Thr Leu Asp Phe Ser Thr Ala
            20                  25                  30

Lys Thr Tyr Val Asp Ser Leu Asn Val Ile Arg Ser Ala Ile Gly Thr
        35                  40                  45

Pro Leu Gln Thr Ile Ser Ser Gly Gly Thr Ser Leu Leu Met Ile Asp
    50                  55                  60

Ser Gly Ser Gly Asp Asn Leu Phe Ala Val Asp Val Arg Gly Ile Asp
65                  70                  75                  80

Ala Glu Glu Gly Arg Phe Asn Asn Leu Arg Leu Ile Val Glu Arg Asn
                85                  90                  95

Asn Leu Tyr Val Thr Gly Phe Val Asn Arg Thr Asn Asn Val Phe Tyr
            100                 105                 110

Arg Phe Ala Asp Phe Ser His Val Thr Phe Pro Gly Thr Thr Ala Val
        115                 120                 125

Thr Leu Ser Gly Asp Ser Ser Tyr Thr Thr Leu Gln Arg Val Ala Gly
    130                 135                 140

Ile Ser Arg Thr Gly Met Gln Ile Asn Arg His Ser Leu Thr Thr Ser
145                 150                 155                 160

Tyr Leu Asp Leu Met Ser His Ser Gly Thr Ser Leu Thr Gln Ser Val
                165                 170                 175

Ala Arg Ala Met Leu Arg Phe Val Thr Val Thr Ala Glu Ala Leu Arg
            180                 185                 190

Phe Arg Gln Ile Gln Arg Gly Phe Arg Thr Thr Leu Asp Asp Leu Ser
        195                 200                 205

Gly Arg Ser Tyr Val Met Thr Ala Glu Asp Val Asp Leu Thr Leu Asn
    210                 215                 220

Trp Gly Arg Leu Ser Ser Val Leu Pro Asp Tyr His Gly Gln Asp Ser
225                 230                 235                 240

Val Arg Val Gly Arg Ile Ser Phe Gly Ser Ile Asn Ala Ile Leu Gly
                245                 250                 255

Ser Val Ala Leu Ile Leu Asn Cys His His Ala Ser Arg Val Ala
            260                 265                 270

Arg Met Ala Ser Asp Glu Phe Pro Ser Met Cys Pro Ala Asp Gly Arg
        275                 280                 285

Val Arg Gly Ile Thr His Asn Lys Ile Leu Trp Asp Ser Ser Thr Leu
    290                 295                 300

Gly Ala Ile Leu Met Arg Arg Thr Ile Ser Ser Leu Glu His His His
305                 310                 315                 320

His His His (2) INFORMATION FOR SEQ ID NO:22:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ii) MOLECULE TYPE: DNA (genomic)
```

(ix) FEATURE:
              (A) NAME/KEY: CDS
              (B) LOCATION: 1..294

(xi) SEQUENCE DESCRIPTION: SEQ ID NO:22:

ATG AAA AAA ACA TTA TTA ATA GCT GCA TCG CTT TCA TTT TTT TCA GCA          48
Met Lys Lys Thr Leu Leu Ile Ala Ala Ser Leu Ser Phe Phe Ser Ala
 1               5                  10                  15

AGT GCG CTG GCG ACG CCT GAT TGT GTA ACT GGA AAG GTG GAG TAT ACA          96
Ser Ala Leu Ala Thr Pro Asp Cys Val Thr Gly Lys Val Glu Tyr Thr
            20                  25                  30

AAA TAT AAT GAT GAC GAT ACC TTT ACA GTT AAA GTG GGT GAT AAA GAA         144
Lys Tyr Asn Asp Asp Asp Thr Phe Thr Val Lys Val Gly Asp Lys Glu
         35                  40                  45

TTA TTT ACC AAC AGA TGG AAT CTT CAG TCT CTT CTT CTC AGT GCG CAA         192
Leu Phe Thr Asn Arg Trp Asn Leu Gln Ser Leu Leu Leu Ser Ala Gln
     50                  55                  60

ATT ACG GGG ATG ACT GTA ACC ATT AAA ACT AAT GCC TGT CAT AAT GGA         240
Ile Thr Gly Met Thr Val Thr Ile Lys Thr Asn Ala Cys His Asn Gly
 65                  70                  75                  80

GGG GGA TTC AGC GAA GTT ATT TTT CGT CTC GAG CAC CAC CAC CAC CAC         288
Gly Gly Phe Ser Glu Val Ile Phe Arg Leu Glu His His His His His
                 85                  90                  95

CAC TGA                                                                 294
His *

(2) INFORMATION FOR SEQ ID NO:23:

(i) SEQUENCE CHARACTERISTICS:
              (A) LENGTH: 97 amino acids
              (B) TYPE: amino acid
              (D) TOPOLOGY: linear (ii) MOLECULE TYPE: protein (xi) SEQUENCE DESCRIPTION: SEQ ID NO:23:

Met Lys Lys Thr Leu Leu Ile Ala Ala Ser Leu Ser Phe Phe Ser Ala
 1               5                  10                  15

Ser Ala Leu Ala Thr Pro Asp Cys Val Thr Gly Lys Val Glu Tyr Thr
            20                  25                  30

Lys Tyr Asn Asp Asp Asp Thr Phe Thr Val Lys Val Gly Asp Lys Glu
         35                  40                  45

Leu Phe Thr Asn Arg Trp Asn Leu Gln Ser Leu Leu Leu Ser Ala Gln
     50                  55                  60

Ile Thr Gly Met Thr Val Thr Ile Lys Thr Asn Ala Cys His Asn Gly
 65                  70                  75                  80

Gly Gly Phe Ser Glu Val Ile Phe Arg Leu Glu His His His His His
                 85                  90                  95

His (2) INFORMATION FOR SEQ ID NO:24:

(i) SEQUENCE CHARACTERISTICS:
              (A) LENGTH: 981 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: CDS (B) LOCATION: 1..981

(xi) SEQUENCE DESCRIPTION: SEQ ID NO:24:

| | | | | | | | | | | | | | | | | |
|---|---|---|---|---|---|---|---|---|---|---|---|---|---|---|---|---|
| ATG | AAG | TGT | ATA | TTA | TTT | AAA | TGG | GTA | CTG | TGC | CTG | TTA | CTG | GGT | TTT | 48 |
| Met | Lys | Cys | Ile | Leu | Phe | Lys | Trp | Val | Leu | Cys | Leu | Leu | Leu | Gly | Phe | |
| 1 | | | | 5 | | | | | 10 | | | | | 15 | | |
| TCT | TCG | GTA | TCC | TAT | TCC | CGG | GAG | TTT | ACG | ATA | GAC | TTT | TCG | ACC | CAA | 96 |
| Ser | Ser | Val | Ser | Tyr | Ser | Arg | Glu | Phe | Thr | Ile | Asp | Phe | Ser | Thr | Gln | |
| | | | 20 | | | | | 25 | | | | | 30 | | | |
| CAA | AGT | TAT | GTC | TCT | TCG | TTA | AAT | AGT | ATA | CGG | ACA | GAG | ATA | TCG | ACC | 144 |
| Gln | Ser | Tyr | Val | Ser | Ser | Leu | Asn | Ser | Ile | Arg | Thr | Glu | Ile | Ser | Thr | |
| | | 35 | | | | | 40 | | | | | 45 | | | | |
| CCT | CTT | GAA | CAT | ATA | TCT | CAG | GGG | ACC | ACA | TCG | GTG | TCT | GTT | ATT | AAC | 192 |
| Pro | Leu | Glu | His | Ile | Ser | Gln | Gly | Thr | Thr | Ser | Val | Ser | Val | Ile | Asn | |
| | 50 | | | | | 55 | | | | | 60 | | | | | |
| CAC | ACC | CAC | GGC | AGT | TAT | TTT | GCT | GTG | GAT | ATA | CGA | GGG | CTT | GAT | GTC | 240 |
| His | Thr | His | Gly | Ser | Tyr | Phe | Ala | Val | Asp | Ile | Arg | Gly | Leu | Asp | Val | |
| 65 | | | | | 70 | | | | | 75 | | | | | 80 | |
| TAT | CAG | GCG | CGT | TTT | GAC | CAT | CTT | CGT | CTG | ATT | ATT | GAG | CAA | AAT | AAT | 288 |
| Tyr | Gln | Ala | Arg | Phe | Asp | His | Leu | Arg | Leu | Ile | Ile | Glu | Gln | Asn | Asn | |
| | | | | 85 | | | | | 90 | | | | | 95 | | |
| TTA | TAT | GTG | GCA | GGG | TTC | GTT | AAT | ACG | GCA | ACA | AAT | ACT | TTC | TAC | CGT | 336 |
| Leu | Tyr | Val | Ala | Gly | Phe | Val | Asn | Thr | Ala | Thr | Asn | Thr | Phe | Tyr | Arg | |
| | | | 100 | | | | | 105 | | | | | 110 | | | |
| TTT | TCA | GAT | TTT | ACA | CAT | ATA | TCA | GTG | CCC | GGT | GTG | ACA | ACG | GTT | TCC | 384 |
| Phe | Ser | Asp | Phe | Thr | His | Ile | Ser | Val | Pro | Gly | Val | Thr | Thr | Val | Ser | |
| | | 115 | | | | | 120 | | | | | 125 | | | | |
| ATG | ACA | ACG | GAC | AGC | AGT | TAT | ACC | ACT | CTG | CAA | CGT | GTC | GCA | GCG | CTG | 432 |
| Met | Thr | Thr | Asp | Ser | Ser | Tyr | Thr | Thr | Leu | Gln | Arg | Val | Ala | Ala | Leu | |
| | 130 | | | | | 135 | | | | | 140 | | | | | |
| GAA | CGT | TCC | GGA | ATG | CAA | ATC | AGT | CGT | CAC | TCA | CTG | GTT | TCA | TCA | TAT | 480 |
| Glu | Arg | Ser | Gly | Met | Gln | Ile | Ser | Arg | His | Ser | Leu | Val | Ser | Ser | Tyr | |
| 145 | | | | | 150 | | | | | 155 | | | | | 160 | |
| CTG | GCG | TTA | ATG | GAG | TTC | AGT | GGT | AAT | ACA | ATG | ACC | AGA | GAT | GCA | TCC | 528 |
| Leu | Ala | Leu | Met | Glu | Phe | Ser | Gly | Asn | Thr | Met | Thr | Arg | Asp | Ala | Ser | |
| | | | | 165 | | | | | 170 | | | | | 175 | | |
| AGA | GCA | GTT | CTG | CGT | TTT | GTC | ACT | GTC | ACA | GCA | GAA | GCC | TTA | CGC | TTC | 576 |
| Arg | Ala | Val | Leu | Arg | Phe | Val | Thr | Val | Thr | Ala | Glu | Ala | Leu | Arg | Phe | |
| | | | 180 | | | | | 185 | | | | | 190 | | | |
| AGG | CAG | ATA | CAG | AGA | GAA | TTT | CGT | CAG | GCA | CTG | TCT | GAA | ACT | GCT | CCT | 624 |
| Arg | Gln | Ile | Gln | Arg | Glu | Phe | Arg | Gln | Ala | Leu | Ser | Glu | Thr | Ala | Pro | |
| | | 195 | | | | | 200 | | | | | 205 | | | | |
| GTG | TAT | ACG | ATG | ACG | CCG | GGA | GAC | GTG | GAC | CTC | ACT | CTG | AAC | TGG | GGG | 672 |
| Val | Tyr | Thr | Met | Thr | Pro | Gly | Asp | Val | Asp | Leu | Thr | Leu | Asn | Trp | Gly | |
| | 210 | | | | | 215 | | | | | 220 | | | | | |
| CGA | ATC | AGC | AAT | GTG | CTT | CCG | GAG | TAT | CGG | GGA | GAG | GAT | GGT | GTC | AGA | 720 |
| Arg | Ile | Ser | Asn | Val | Leu | Pro | Glu | Tyr | Arg | Gly | Glu | Asp | Gly | Val | Arg | |
| 225 | | | | | 230 | | | | | 235 | | | | | 240 | |
| GTG | GGG | AGA | ATA | TCC | TTT | AAT | AAT | ATA | TCA | GCG | ATA | CTG | GGG | ACT | GTG | 768 |
| Val | Gly | Arg | Ile | Ser | Phe | Asn | Asn | Ile | Ser | Ala | Ile | Leu | Gly | Thr | Val | |
| | | | | 245 | | | | | 250 | | | | | 255 | | |
| GCC | GTT | ATA | CTG | AAT | TGC | CAT | CAT | CAG | GGG | GCG | CGT | TCT | GTT | CGC | GCC | 816 |
| Ala | Val | Ile | Leu | Asn | Cys | His | His | Gln | Gly | Ala | Arg | Ser | Val | Arg | Ala | |
| | | | 260 | | | | | 265 | | | | | 270 | | | |
| GTG | AAT | GAA | GAG | AGT | CAA | CCA | GAA | TGT | CAG | ATA | ACT | GGC | GAC | AGG | CCT | 864 |
| Val | Asn | Glu | Glu | Ser | Gln | Pro | Glu | Cys | Gln | Ile | Thr | Gly | Asp | Arg | Pro | |
| | | 275 | | | | | 280 | | | | | 285 | | | | |
| GTT | ATA | AAA | ATA | AAC | AAT | ACA | TTA | TGG | GAA | AGT | AAT | ACA | GCT | GCA | GCG | 912 |
| Val | Ile | Lys | Ile | Asn | Asn | Thr | Leu | Trp | Glu | Ser | Asn | Thr | Ala | Ala | Ala | |
| | 290 | | | | | 295 | | | | | 300 | | | | | |

```
TTT CTG AAC AGA AAG TCA CAG TTT TTA TAT ACA ACG GGT AAA CTC GAG        960
Phe Leu Asn Arg Lys Ser Gln Phe Leu Tyr Thr Thr Gly Lys Leu Glu
305                 310                 315                 320

CAC CAC CAC CAC CAC CAC TGA                                             981
His His His His His His  *
                    325
```

(2) INFORMATION FOR SEQ ID NO:25:

(i) SEQUENCE CHARACTERISTICS:
        (A) LENGTH: 326 amino acids
        (B) TYPE: amino acid
        (D) TOPOLOGY: linear (ii) MOLECULE TYPE: protein (xi) SEQUENCE DESCRIPTION: SEQ ID NO:25:

```
Met Lys Cys Ile Leu Phe Lys Trp Val Leu Cys Leu Leu Gly Phe
 1               5                  10                  15

Ser Ser Val Ser Tyr Ser Arg Glu Phe Thr Ile Asp Phe Ser Thr Gln
                20                  25                  30

Gln Ser Tyr Val Ser Ser Leu Asn Ser Ile Arg Thr Glu Ile Ser Thr
            35                  40                  45

Pro Leu Glu His Ile Ser Gln Gly Thr Thr Ser Val Ser Val Ile Asn
 50                  55                  60

His Thr His Gly Ser Tyr Phe Ala Val Asp Ile Arg Gly Leu Asp Val
 65                  70                  75                  80

Tyr Gln Ala Arg Phe Asp His Leu Arg Leu Ile Ile Glu Gln Asn Asn
                85                  90                  95

Leu Tyr Val Ala Gly Phe Val Asn Thr Ala Thr Asn Thr Phe Tyr Arg
            100                 105                 110

Phe Ser Asp Phe Thr His Ile Ser Val Pro Gly Val Thr Thr Val Ser
            115                 120                 125

Met Thr Thr Asp Ser Ser Tyr Thr Thr Leu Gln Arg Val Ala Ala Leu
130                 135                 140

Glu Arg Ser Gly Met Gln Ile Ser Arg His Ser Leu Val Ser Ser Tyr
145                 150                 155                 160

Leu Ala Leu Met Glu Phe Ser Gly Asn Thr Met Thr Arg Asp Ala Ser
                165                 170                 175

Arg Ala Val Leu Arg Phe Val Thr Val Thr Ala Glu Ala Leu Arg Phe
            180                 185                 190

Arg Gln Ile Gln Arg Glu Phe Arg Gln Ala Leu Ser Glu Thr Ala Pro
            195                 200                 205

Val Tyr Thr Met Thr Pro Gly Asp Val Asp Leu Thr Leu Asn Trp Gly
            210                 215                 220

Arg Ile Ser Asn Val Leu Pro Glu Tyr Arg Gly Glu Asp Gly Val Arg
225                 230                 235                 240

Val Gly Arg Ile Ser Phe Asn Asn Ile Ser Ala Ile Leu Gly Thr Val
                245                 250                 255

Ala Val Ile Leu Asn Cys His His Gln Gly Ala Arg Ser Val Arg Ala
            260                 265                 270

Val Asn Glu Glu Ser Gln Pro Glu Cys Gln Ile Thr Gly Asp Arg Pro
            275                 280                 285

Val Ile Lys Ile Asn Asn Thr Leu Trp Glu Ser Asn Thr Ala Ala Ala
            290                 295                 300

Phe Leu Asn Arg Lys Ser Gln Phe Leu Tyr Thr Thr Gly Lys Leu Glu
```

```
                305                 310                 315                 320
His His His His His His
                325

(2) INFORMATION FOR SEQ ID NO:26:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..294

(xi) SEQUENCE DESCRIPTION: SEQ ID NO:26:

ATG AAG AAG ATG TTT ATG GCG GTT TTA TTT GCA TTA GCT TCT GTT AAT        48
Met Lys Lys Met Phe Met Ala Val Leu Phe Ala Leu Ala Ser Val Asn
 1               5                  10                  15

GCA ATG GCG GCG GAT TGT GCT AAA GGT AAA ATT GAG TTT TCC AAG TAT        96
Ala Met Ala Ala Asp Cys Ala Lys Gly Lys Ile Glu Phe Ser Lys Tyr
             20                  25                  30

AAT GAG GAT GAC ACA TTT ACA GTG AAG GTT GAC GGG AAA GAA TAC TGG       144
Asn Glu Asp Asp Thr Phe Thr Val Lys Val Asp Gly Lys Glu Tyr Trp
         35                  40                  45

ACC AGT CGC TGG AAT CTG CAA CCG TTA CTG CAA AGT GCT CAG TTG ACA       192
Thr Ser Arg Trp Asn Leu Gln Pro Leu Leu Gln Ser Ala Gln Leu Thr
     50                  55                  60

GGA ATG ACT GTC ACA ATC AAA TCC AGT ACC TGT GAA TCA GGC TCC GGA       240
Gly Met Thr Val Thr Ile Lys Ser Ser Thr Cys Glu Ser Gly Ser Gly
 65                  70                  75                  80

TTT GCT GAA GTG CAG TTT AAT AAT GAC CTC GAG CAC CAC CAC CAC CAC       288
Phe Ala Glu Val Gln Phe Asn Asn Asp Leu Glu His His His His His
                 85                  90                  95

CAC TGA                                                                294
His *

(2) INFORMATION FOR SEQ ID NO:27:

(i) SEQUENCE CHARACTERISTICS:
        (A) LENGTH:  97 amino acids
        (B) TYPE: amino acid
        (D) TOPOLOGY: linear (ii) MOLECULE TYPE: protein (xi) SEQUENCE DESCRIPTION: SEQ ID NO:27:

Met Lys Lys Met Phe Met Ala Val Leu Phe Ala Leu Ala Ser Val Asn
 1               5                  10                  15

Ala Met Ala Ala Asp Cys Ala Lys Gly Lys Ile Glu Phe Ser Lys Tyr
             20                  25                  30

Asn Glu Asp Asp Thr Phe Thr Val Lys Val Asp Gly Lys Glu Tyr Trp
         35                  40                  45

Thr Ser Arg Trp Asn Leu Gln Pro Leu Leu Gln Ser Ala Gln Leu Thr
     50                  55                  60

Gly Met Thr Val Thr Ile Lys Ser Ser Thr Cys Glu Ser Gly Ser Gly
 65                  70                  75                  80

Phe Ala Glu Val Gln Phe Asn Asn Asp Leu Glu His His His His
                 85                  90                  95
```

His (2) INFORMATION FOR SEQ ID NO:28:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CGGAATTCAA GGAATTTACC TTAGACTTCT CG                          32

(2) INFORMATION FOR SEQ ID NO:29:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GGCTCGAGTC AACTGCTAAT AGTTCTGC                              28

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CGGAATTCCG GGAGTTTACG ATAGACTTTT CG                          32

(2) INFORMATION FOR SEQ ID NO:31:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GGCTCGAGTT ATTTACCCGT TGTATATAA                             29

(2) INFORMATION FOR SEQ ID NO:32:

(i) SEQUENCE CHARACTERISTICS:
        (A) LENGTH: 2127 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..2127

(xi) SEQUENCE DESCRIPTION: SEQ ID NO:32:

```
ATG AAA ATA AAA ACA GGT GCA CGC ATC CTC GCA TTA TCC GCA TTA ACG         48
Met Lys Ile Lys Thr Gly Ala Arg Ile Leu Ala Leu Ser Ala Leu Thr
 1               5                  10                  15

ACG ATG ATG TTT TCC GCC TCG GCT CTC GCC AAA ATC GAA GAA GGT AAA         96
Thr Met Met Phe Ser Ala Ser Ala Leu Ala Lys Ile Glu Glu Gly Lys
                    20                  25                  30

CTG GTA ATC TGG ATT AAC GGC GAT AAA GGC TAT AAC GGT CTC GCT GAA        144
Leu Val Ile Trp Ile Asn Gly Asp Lys Gly Tyr Asn Gly Leu Ala Glu
             35                  40                  45

GTC GGT AAG AAA TTC GAG AAA GAT ACC GGA ATT AAA GTC ACC GTT GAG        192
Val Gly Lys Lys Phe Glu Lys Asp Thr Gly Ile Lys Val Thr Val Glu
         50                  55                  60

CAT CCG GAT AAA CTG GAA GAG AAA TTC CCA CAG GTT GCG GCA ACT GGC        240
His Pro Asp Lys Leu Glu Glu Lys Phe Pro Gln Val Ala Ala Thr Gly
 65                  70                  75                  80

GAT GGC CCT GAC ATT ATC TTC TGG GCA CAC GAC CGC TTT GGT GGC TAC        288
Asp Gly Pro Asp Ile Ile Phe Trp Ala His Asp Arg Phe Gly Gly Tyr
                     85                  90                  95

GCT CAA TCT GGC CTG TTG GCT GAA ATC ACC CCG GAC AAA GCG TTC CAG        336
Ala Gln Ser Gly Leu Leu Ala Glu Ile Thr Pro Asp Lys Ala Phe Gln
                100                 105                 110

GAC AAG CTG TAT CCG TTT ACC TGG GAT GCC GTA CGT TAC AAC GGC AAG        384
Asp Lys Leu Tyr Pro Phe Thr Trp Asp Ala Val Arg Tyr Asn Gly Lys
            115                 120                 125

CTG ATT GCT TAC CCG ATC GCT GTT GAA GCG TTA TCG CTG ATT TAT AAC        432
Leu Ile Ala Tyr Pro Ile Ala Val Glu Ala Leu Ser Leu Ile Tyr Asn
        130                 135                 140

AAA GAT CTG CTG CCG AAC CCG CCA AAA ACC TGG GAA GAG ATC CCG GCG        480
Lys Asp Leu Leu Pro Asn Pro Pro Lys Thr Trp Glu Glu Ile Pro Ala
145                 150                 155                 160

CTG GAT AAA GAA CTG AAA GCG AAA GGT AAG AGC GCG CTG ATG TTC AAC        528
Leu Asp Lys Glu Leu Lys Ala Lys Gly Lys Ser Ala Leu Met Phe Asn
                165                 170                 175

CTG CAA GAA CCG TAC TTC ACC TGG CCG CTG ATT GCT GCT GAC GGG GGT        576
Leu Gln Glu Pro Tyr Phe Thr Trp Pro Leu Ile Ala Ala Asp Gly Gly
            180                 185                 190

TAT GCG TTC AAG TAT GAA AAC GGC AAG TAC GAC ATT AAA GAC GTG GGC        624
Tyr Ala Phe Lys Tyr Glu Asn Gly Lys Tyr Asp Ile Lys Asp Val Gly
        195                 200                 205

GTG GAT AAC GCT GGC GCG AAA GCG GGT CTG ACC TTC CTG GTT GAC CTG        672
Val Asp Asn Ala Gly Ala Lys Ala Gly Leu Thr Phe Leu Val Asp Leu
    210                 215                 220

ATT AAA AAC AAA CAC ATG AAT GCA GAC ACC GAT TAC TCC ATC GCA GAA        720
Ile Lys Asn Lys His Met Asn Ala Asp Thr Asp Tyr Ser Ile Ala Glu
225                 230                 235                 240

GCT GCC TTT AAT AAA GGC GAA ACA GCG ATG ACC ATC AAC GGC CCG TGG        768
Ala Ala Phe Asn Lys Gly Glu Thr Ala Met Thr Ile Asn Gly Pro Trp
                245                 250                 255

GCA TGG TCC AAC ATC GAC ACC AGC AAA GTG AAT TAT GGT GTA ACG GTA        816
Ala Trp Ser Asn Ile Asp Thr Ser Lys Val Asn Tyr Gly Val Thr Val
            260                 265                 270

CTG CCG ACC TTC AAG GGT CAA CCA TCC AAA CCG TTC GTT GGC GTG CTG        864
Leu Pro Thr Phe Lys Gly Gln Pro Ser Lys Pro Phe Val Gly Val Leu
        275                 280                 285

AGC GCA GGT ATT AAC GCC GCC AGT CCG AAC AAA GAG CTG GCG AAA GAG        912
Ser Ala Gly Ile Asn Ala Ala Ser Pro Asn Lys Glu Leu Ala Lys Glu
    290                 295                 300

TTC CTC GAA AAC TAT CTG CTG ACT GAT GAA GGT CTG GAA GCG GTT AAT        960
Phe Leu Glu Asn Tyr Leu Leu Thr Asp Glu Gly Leu Glu Ala Val Asn
305                 310                 315                 320
```

-continued

| | | | | | | | | | | | | | | | | |
|---|---|---|---|---|---|---|---|---|---|---|---|---|---|---|---|---|
| AAA | GAC | AAA | CCG | CTG | GGT | GCC | GTA | GCG | CTG | AAG | TCT | TAC | GAG | GAA | GAG | 1008 |
| Lys | Asp | Lys | Pro | Leu | Gly | Ala | Val | Ala | Leu | Lys | Ser | Tyr | Glu | Glu | Glu | |
| | | | | 325 | | | | | 330 | | | | | 335 | | |
| TTG | GCG | AAA | GAT | CCA | CGT | ATT | GCC | GCC | ACC | ATG | GAA | AAC | GCC | CAG | AAA | 1056 |
| Leu | Ala | Lys | Asp | Pro | Arg | Ile | Ala | Ala | Thr | Met | Glu | Asn | Ala | Gln | Lys | |
| | | | 340 | | | | | 345 | | | | | 350 | | | |
| GGT | GAA | ATC | ATG | CCG | AAC | ATC | CCG | CAG | ATG | TCC | GCT | TTC | TGG | TAT | GCC | 1104 |
| Gly | Glu | Ile | Met | Pro | Asn | Ile | Pro | Gln | Met | Ser | Ala | Phe | Trp | Tyr | Ala | |
| | | | 355 | | | | | 360 | | | | | 365 | | | |
| GTG | CGT | ACT | GCG | GTG | ATC | AAC | GCC | GCC | AGC | GGT | CGT | CAG | ACT | GTC | GAT | 1152 |
| Val | Arg | Thr | Ala | Val | Ile | Asn | Ala | Ala | Ser | Gly | Arg | Gln | Thr | Val | Asp | |
| | 370 | | | | | 375 | | | | | 380 | | | | | |
| GAA | GCC | CTG | AAA | GAC | GCG | CAG | ACT | TCG | AGC | TCG | AAC | AAC | AAC | AAC | AAT | 1200 |
| Glu | Ala | Leu | Lys | Asp | Ala | Gln | Thr | Ser | Ser | Ser | Asn | Asn | Asn | Asn | Asn | |
| 385 | | | | | 390 | | | | | 395 | | | | | 400 | |
| AAC | AAT | AAC | AAC | AAC | CTC | GGG | ATC | GAG | GGA | AGG | ATT | TCA | GAA | TTC | AAG | 1248 |
| Asn | Asn | Asn | Asn | Asn | Leu | Gly | Ile | Glu | Gly | Arg | Ile | Ser | Glu | Phe | Lys | |
| | | | | 405 | | | | | 410 | | | | | 415 | | |
| GAA | TTT | ACC | TTA | GAC | TTC | TCG | ACT | GCA | AAG | ACG | TAT | GTA | GAT | TCG | CTG | 1296 |
| Glu | Phe | Thr | Leu | Asp | Phe | Ser | Thr | Ala | Lys | Thr | Tyr | Val | Asp | Ser | Leu | |
| | | | 420 | | | | | 425 | | | | | 430 | | | |
| AAT | GTC | ATT | CGC | TCT | GCA | ATA | GGT | ACT | CCA | TTA | CAG | ACT | ATT | TCA | TCA | 1344 |
| Asn | Val | Ile | Arg | Ser | Ala | Ile | Gly | Thr | Pro | Leu | Gln | Thr | Ile | Ser | Ser | |
| | | | 435 | | | | | 440 | | | | | 445 | | | |
| GGA | GGT | ACG | TCT | TTA | CTG | ATG | ATT | GAT | AGT | GGC | TCA | GGG | GAT | AAT | TTG | 1392 |
| Gly | Gly | Thr | Ser | Leu | Leu | Met | Ile | Asp | Ser | Gly | Ser | Gly | Asp | Asn | Leu | |
| | | 450 | | | | | 455 | | | | | 460 | | | | |
| TTT | GCA | GTT | GAT | GTC | AGA | GGG | ATA | GAT | GCA | GAG | GAA | GGG | CGG | TTT | AAT | 1440 |
| Phe | Ala | Val | Asp | Val | Arg | Gly | Ile | Asp | Ala | Glu | Glu | Gly | Arg | Phe | Asn | |
| 465 | | | | | 470 | | | | | 475 | | | | | 480 | |
| AAT | CTA | CGG | CTT | ATT | GTT | GAA | CGA | AAT | AAT | TTA | TAT | GTG | ACA | GGA | TTT | 1488 |
| Asn | Leu | Arg | Leu | Ile | Val | Glu | Arg | Asn | Asn | Leu | Tyr | Val | Thr | Gly | Phe | |
| | | | | 485 | | | | | 490 | | | | | 495 | | |
| GTT | AAC | AGG | ACA | AAT | AAT | GTT | TTT | TAT | CGC | TTT | GCT | GAT | TTT | TCA | CAT | 1536 |
| Val | Asn | Arg | Thr | Asn | Asn | Val | Phe | Tyr | Arg | Phe | Ala | Asp | Phe | Ser | His | |
| | | | 500 | | | | | 505 | | | | | 510 | | | |
| GTT | ACC | TTT | CCA | GGT | ACA | ACA | GCG | GTT | ACA | TTG | TCT | GGT | GAC | AGT | AGC | 1584 |
| Val | Thr | Phe | Pro | Gly | Thr | Thr | Ala | Val | Thr | Leu | Ser | Gly | Asp | Ser | Ser | |
| | | | 515 | | | | | 520 | | | | | 525 | | | |
| TAT | ACC | ACG | TTA | CAG | CGT | GTT | GCA | GGG | ATC | AGT | CGT | ACG | GGG | ATG | CAG | 1632 |
| Tyr | Thr | Thr | Leu | Gln | Arg | Val | Ala | Gly | Ile | Ser | Arg | Thr | Gly | Met | Gln | |
| | | 530 | | | | | 535 | | | | | 540 | | | | |
| ATA | AAT | CGC | CAT | TCG | TTG | ACT | ACT | TCT | TAT | CTG | GAT | TTA | ATG | TCG | CAT | 1680 |
| Ile | Asn | Arg | His | Ser | Leu | Thr | Thr | Ser | Tyr | Leu | Asp | Leu | Met | Ser | His | |
| 545 | | | | | 550 | | | | | 555 | | | | | 560 | |
| AGT | GGA | ACC | TCA | CTG | ACG | CAG | TCT | GTG | GCA | AGA | GCG | ATG | TTA | CGG | TTT | 1728 |
| Ser | Gly | Thr | Ser | Leu | Thr | Gln | Ser | Val | Ala | Arg | Ala | Met | Leu | Arg | Phe | |
| | | | 565 | | | | | 570 | | | | | 575 | | | |
| GTT | ACT | GTG | ACA | GCT | GAA | GCT | TTA | CGT | TTT | CGG | CAA | ATA | CAG | AGG | GGA | 1776 |
| Val | Thr | Val | Thr | Ala | Glu | Ala | Leu | Arg | Phe | Arg | Gln | Ile | Gln | Arg | Gly | |
| | | | 580 | | | | | 585 | | | | | 590 | | | |
| TTT | CGT | ACA | ACA | CTG | GAT | GAT | CTC | AGT | GGG | CGT | TCT | TAT | GTA | ATG | ACT | 1824 |
| Phe | Arg | Thr | Thr | Leu | Asp | Asp | Leu | Ser | Gly | Arg | Ser | Tyr | Val | Met | Thr | |
| | | | 595 | | | | | 600 | | | | | 605 | | | |
| GCT | GAA | GAT | GTT | GAT | CTT | ACA | TTG | AAC | TGG | GGA | AGG | TTG | AGT | AGC | GTC | 1872 |
| Ala | Glu | Asp | Val | Asp | Leu | Thr | Leu | Asn | Trp | Gly | Arg | Leu | Ser | Ser | Val | |
| | | | 610 | | | | | 615 | | | | | 620 | | | |
| CTG | CCT | GAC | TAT | CAT | GGA | CAA | GAC | TCT | GTT | CGT | GTA | GGA | AGA | ATT | TCT | 1920 |
| Leu | Pro | Asp | Tyr | His | Gly | Gln | Asp | Ser | Val | Arg | Val | Gly | Arg | Ile | Ser | |

-continued

```
                    625                 630                 635                 640
TTT GGA AGC ATT AAT GCA ATT CTG GGA AGC GTG GCA TTA ATA CTG AAT          1968
Phe Gly Ser Ile Asn Ala Ile Leu Gly Ser Val Ala Leu Ile Leu Asn
                645                 650                 655

TGT CAT CAT CAT GCA TCG CGA GTT GCC AGA ATG GCA TCT GAT GAG TTT          2016
Cys His His His Ala Ser Arg Val Ala Arg Met Ala Ser Asp Glu Phe
                660                 665                 670

CCT TCT ATG TGT CCG GCA GAT GGA AGA GTC CGT GGG ATT ACG CAC AAT          2064
Pro Ser Met Cys Pro Ala Asp Gly Arg Val Arg Gly Ile Thr His Asn
                675                 680                 685

AAA ATA TTG TGG GAT TCA TCC ACT CTG GGG GCA ATT CTG ATG CGC AGA          2112
Lys Ile Leu Trp Asp Ser Ser Thr Leu Gly Ala Ile Leu Met Arg Arg
                690                 695                 700

ACT ATT AGC AGT TGA                                                       2127
Thr Ile Ser Ser *
705
```

(2) INFORMATION FOR SEQ ID NO:33:

(i) SEQUENCE CHARACTERISTICS:
        (A) LENGTH: 708 amino acids
        (B) TYPE: amino acid
        (D) TOPOLOGY: linear (ii) MOLECULE TYPE: protein (xi) SEQUENCE DESCRIPTION: SEQ ID NO:33:

```
Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
                35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
                100                 105                 110

Asp Lys Leu Tyr Pro Phe Thr Trp Asp Ala Val Arg Tyr Asn Gly Lys
                115                 120                 125

Leu Ile Ala Tyr Pro Ile Ala Val Glu Ala Leu Ser Leu Ile Tyr Asn
        130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
                180                 185                 190

Tyr Ala Phe Lys Tyr Glu Asn Gly Lys Tyr Asp Ile Lys Asp Val Gly
                195                 200                 205

Val Asp Asn Ala Gly Ala Lys Ala Gly Leu Thr Phe Leu Val Asp Leu
        210                 215                 220

Ile Lys Asn Lys His Met Asn Ala Asp Thr Asp Tyr Ser Ile Ala Glu
225                 230                 235                 240
```

-continued

```
Ala Ala Phe Asn Lys Gly Glu Thr Ala Met Thr Ile Asn Gly Pro Trp
            245                 250                 255
Ala Trp Ser Asn Ile Asp Thr Ser Lys Val Asn Tyr Gly Val Thr Val
            260                 265                 270
Leu Pro Thr Phe Lys Gly Gln Pro Ser Lys Pro Phe Val Gly Val Leu
            275                 280                 285
Ser Ala Gly Ile Asn Ala Ala Ser Pro Asn Lys Glu Leu Ala Lys Glu
290                 295                 300
Phe Leu Glu Asn Tyr Leu Leu Thr Asp Glu Gly Leu Glu Ala Val Asn
305                 310                 315                 320
Lys Asp Lys Pro Leu Gly Ala Val Ala Leu Lys Ser Tyr Glu Glu Glu
            325                 330                 335
Leu Ala Lys Asp Pro Arg Ile Ala Ala Thr Met Glu Asn Ala Gln Lys
            340                 345                 350
Gly Glu Ile Met Pro Asn Ile Pro Gln Met Ser Ala Phe Trp Tyr Ala
            355                 360                 365
Val Arg Thr Ala Val Ile Asn Ala Ala Ser Gly Arg Gln Thr Val Asp
            370                 375                 380
Glu Ala Leu Lys Asp Ala Gln Thr Ser Ser Ser Asn Asn Asn Asn Asn
385                 390                 395                 400
Asn Asn Asn Asn Asn Leu Gly Ile Glu Gly Arg Ile Ser Glu Phe Lys
            405                 410                 415
Glu Phe Thr Leu Asp Phe Ser Thr Ala Lys Thr Tyr Val Asp Ser Leu
            420                 425                 430
Asn Val Ile Arg Ser Ala Ile Gly Thr Pro Leu Gln Thr Ile Ser Ser
            435                 440                 445
Gly Gly Thr Ser Leu Leu Met Ile Asp Ser Gly Ser Gly Asp Asn Leu
            450                 455                 460
Phe Ala Val Asp Val Arg Gly Ile Asp Ala Glu Glu Gly Arg Phe Asn
465                 470                 475                 480
Asn Leu Arg Leu Ile Val Glu Arg Asn Asn Leu Tyr Val Thr Gly Phe
            485                 490                 495
Val Asn Arg Thr Asn Asn Val Phe Tyr Arg Phe Ala Asp Phe Ser His
            500                 505                 510
Val Thr Phe Pro Gly Thr Thr Ala Val Thr Leu Ser Gly Asp Ser Ser
            515                 520                 525
Tyr Thr Thr Leu Gln Arg Val Ala Gly Ile Ser Arg Thr Gly Met Gln
            530                 535                 540
Ile Asn Arg His Ser Leu Thr Thr Ser Tyr Leu Asp Leu Met Ser His
545                 550                 555                 560
Ser Gly Thr Ser Leu Thr Gln Ser Val Ala Arg Ala Met Leu Arg Phe
            565                 570                 575
Val Thr Val Thr Ala Glu Ala Leu Arg Phe Arg Gln Ile Gln Arg Gly
            580                 585                 590
Phe Arg Thr Thr Leu Asp Asp Leu Ser Gly Arg Ser Tyr Val Met Thr
            595                 600                 605
Ala Glu Asp Val Asp Leu Thr Leu Asn Trp Gly Arg Leu Ser Ser Val
            610                 615                 620
Leu Pro Asp Tyr His Gly Gln Asp Ser Val Arg Val Gly Arg Ile Ser
625                 630                 635                 640
Phe Gly Ser Ile Asn Ala Ile Leu Gly Ser Val Ala Leu Ile Leu Asn
            645                 650                 655
Cys His His His Ala Ser Arg Val Ala Arg Met Ala Ser Asp Glu Phe
```

```
                      660                 665                 670
Pro Ser Met Cys Pro Ala Asp Gly Arg Val Arg Gly Ile Thr His Asn
            675                 680                 685

Lys Ile Leu Trp Asp Ser Ser Thr Leu Gly Ala Ile Leu Met Arg Arg
    690                 695                 700

Thr Ile Ser Ser
705

(2) INFORMATION FOR SEQ ID NO:34:

(i) SEQUENCE CHARACTERISTICS:
        (A) LENGTH: 2136 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..2136

(xi) SEQUENCE DESCRIPTION: SEQ ID NO:34:

ATG AAA ATA AAA ACA GGT GCA CGC ATC CTC GCA TTA TCC GCA TTA ACG    48
Met Lys Ile Lys Thr Gly Ala Arg Ile Leu Ala Leu Ser Ala Leu Thr
 1               5                  10                  15

ACG ATG ATG TTT TCC GCC TCG GCT CTC GCC AAA ATC GAA GAA GGT AAA    96
Thr Met Met Phe Ser Ala Ser Ala Leu Ala Lys Ile Glu Glu Gly Lys
                20                  25                  30

CTG GTA ATC TGG ATT AAC GGC GAT AAA GGC TAT AAC GGT CTC GCT GAA   144
Leu Val Ile Trp Ile Asn Gly Asp Lys Gly Tyr Asn Gly Leu Ala Glu
            35                  40                  45

GTC GGT AAG AAA TTC GAG AAA GAT ACC GGA ATT AAA GTC ACC GTT GAG   192
Val Gly Lys Lys Phe Glu Lys Asp Thr Gly Ile Lys Val Thr Val Glu
        50                  55                  60

CAT CCG GAT AAA CTG GAA GAG AAA TTC CCA CAG GTT GCG GCA ACT GGC   240
His Pro Asp Lys Leu Glu Glu Lys Phe Pro Gln Val Ala Ala Thr Gly
 65                  70                  75                  80

GAT GGC CCT GAC ATT ATC TTC TGG GCA CAC GAC CGC TTT GGT GGC TAC   288
Asp Gly Pro Asp Ile Ile Phe Trp Ala His Asp Arg Phe Gly Gly Tyr
                85                  90                  95

GCT CAA TCT GGC CTG TTG GCT GAA ATC ACC CCG GAC AAA GCG TTC CAG   336
Ala Gln Ser Gly Leu Leu Ala Glu Ile Thr Pro Asp Lys Ala Phe Gln
            100                 105                 110

GAC AAG CTG TAT CCG TTT ACC TGG GAT GCC GTA CGT TAC AAC GGC AAG   384
Asp Lys Leu Tyr Pro Phe Thr Trp Asp Ala Val Arg Tyr Asn Gly Lys
        115                 120                 125

CTG ATT GCT TAC CCG ATC GCT GTT GAA GCG TTA TCG CTG ATT TAT AAC   432
Leu Ile Ala Tyr Pro Ile Ala Val Glu Ala Leu Ser Leu Ile Tyr Asn
    130                 135                 140

AAA GAT CTG CTG CCG AAC CCG CCA AAA ACC TGG GAA GAG ATC CCG GCG   480
Lys Asp Leu Leu Pro Asn Pro Pro Lys Thr Trp Glu Glu Ile Pro Ala
145                 150                 155                 160

CTG GAT AAA GAA CTG AAA GCG AAA GGT AAG AGC GCG CTG ATG TTC AAC   528
Leu Asp Lys Glu Leu Lys Ala Lys Gly Lys Ser Ala Leu Met Phe Asn
                165                 170                 175

CTG CAA GAA CCG TAC TTC ACC TGG CCG CTG ATT GCT GCT GAC GGG GGT   576
Leu Gln Glu Pro Tyr Phe Thr Trp Pro Leu Ile Ala Ala Asp Gly Gly
            180                 185                 190

TAT GCG TTC AAG TAT GAA AAC GGC AAG TAC GAC ATT AAA GAC GTG GGC   624
Tyr Ala Phe Lys Tyr Glu Asn Gly Lys Tyr Asp Ile Lys Asp Val Gly
        195                 200                 205
```

```
GTG GAT AAC GCT GGC GCG AAA GCG GGT CTG ACC TTC CTG GTT GAC CTG      672
Val Asp Asn Ala Gly Ala Lys Ala Gly Leu Thr Phe Leu Val Asp Leu
    210                 215                 220

ATT AAA AAC AAA CAC ATG AAT GCA GAC ACC GAT TAC TCC ATC GCA GAA      720
Ile Lys Asn Lys His Met Asn Ala Asp Thr Asp Tyr Ser Ile Ala Glu
225                 230                 235                 240

GCT GCC TTT AAT AAA GGC GAA ACA GCG ATG ACC ATC AAC GGC CCG TGG      768
Ala Ala Phe Asn Lys Gly Glu Thr Ala Met Thr Ile Asn Gly Pro Trp
                245                 250                 255

GCA TGG TCC AAC ATC GAC ACC AGC AAA GTG AAT TAT GGT GTA ACG GTA      816
Ala Trp Ser Asn Ile Asp Thr Ser Lys Val Asn Tyr Gly Val Thr Val
            260                 265                 270

CTG CCG ACC TTC AAG GGT CAA CCA TCC AAA CCG TTC GTT GGC GTG CTG      864
Leu Pro Thr Phe Lys Gly Gln Pro Ser Lys Pro Phe Val Gly Val Leu
        275                 280                 285

AGC GCA GGT ATT AAC GCC GCC AGT CCG AAC AAA GAG CTG GCG AAA GAG      912
Ser Ala Gly Ile Asn Ala Ala Ser Pro Asn Lys Glu Leu Ala Lys Glu
    290                 295                 300

TTC CTC GAA AAC TAT CTG CTG ACT GAT GAA GGT CTG GAA GCG GTT AAT      960
Phe Leu Glu Asn Tyr Leu Leu Thr Asp Glu Gly Leu Glu Ala Val Asn
305                 310                 315                 320

AAA GAC AAA CCG CTG GGT GCC GTA GCG CTG AAG TCT TAC GAG GAA GAG     1008
Lys Asp Lys Pro Leu Gly Ala Val Ala Leu Lys Ser Tyr Glu Glu Glu
                325                 330                 335

TTG GCG AAA GAT CCA CGT ATT GCC GCC ACC ATG GAA AAC GCC CAG AAA     1056
Leu Ala Lys Asp Pro Arg Ile Ala Ala Thr Met Glu Asn Ala Gln Lys
            340                 345                 350

GGT GAA ATC ATG CCG AAC ATC CCG CAG ATG TCC GCT TTC TGG TAT GCC     1104
Gly Glu Ile Met Pro Asn Ile Pro Gln Met Ser Ala Phe Trp Tyr Ala
        355                 360                 365

GTG CGT ACT GCG GTG ATC AAC GCC GCC AGC GGT CGT CAG ACT GTC GAT     1152
Val Arg Thr Ala Val Ile Asn Ala Ala Ser Gly Arg Gln Thr Val Asp
    370                 375                 380

GAA GCC CTG AAA GAC GCG CAG ACT TCG AGC TCG AAC AAC AAC AAC AAT     1200
Glu Ala Leu Lys Asp Ala Gln Thr Ser Ser Ser Asn Asn Asn Asn Asn
385                 390                 395                 400

AAC AAT AAC AAC AAC CTC GGG ATC GAG GGA AGG ATT TCA GAA TTC CGG     1248
Asn Asn Asn Asn Asn Leu Gly Ile Glu Gly Arg Ile Ser Glu Phe Arg
                405                 410                 415

GAG TTT ACG ATA GAC TTT TCG ACC CAA CAA AGT TAT GTC TCT TCG TTA     1296
Glu Phe Thr Ile Asp Phe Ser Thr Gln Gln Ser Tyr Val Ser Ser Leu
            420                 425                 430

AAT AGT ATA CGG ACA GAG ATA TCG ACC CCT CTT GAA CAT ATA TCT CAG     1344
Asn Ser Ile Arg Thr Glu Ile Ser Thr Pro Leu Glu His Ile Ser Gln
        435                 440                 445

GGG ACC ACA TCG GTG TCT GTT ATT AAC CAC ACC CAC GGC AGT TAT TTT     1392
Gly Thr Thr Ser Val Ser Val Ile Asn His Thr His Gly Ser Tyr Phe
    450                 455                 460

GCT GTG GAT ATA CGA GGG CTT GAT GTC TAT CAG GCG CGT TTT GAC CAT     1440
Ala Val Asp Ile Arg Gly Leu Asp Val Tyr Gln Ala Arg Phe Asp His
465                 470                 475                 480

CTT CGT CTG ATT ATT GAG CAA AAT AAT TTA TAT GTG GCA GGG TTC GTT     1488
Leu Arg Leu Ile Ile Glu Gln Asn Asn Leu Tyr Val Ala Gly Phe Val
                485                 490                 495

AAT ACG GCA ACA AAT ACT TTC TAC CGT TTT TCA GAT TTT ACA CAT ATA     1536
Asn Thr Ala Thr Asn Thr Phe Tyr Arg Phe Ser Asp Phe Thr His Ile
            500                 505                 510

TCA GTG CCC GGT GTG ACA ACG GTT TCC ATG ACA ACG GAC AGC AGT TAT     1584
Ser Val Pro Gly Val Thr Thr Val Ser Met Thr Thr Asp Ser Ser Tyr
```

-continued

```
            515                 520                      525
ACC ACT CTG CAA CGT GTC GCA GCG CTG GAA CGT TCC GGA ATG CAA ATC     1632
Thr Thr Leu Gln Arg Val Ala Ala Leu Glu Arg Ser Gly Met Gln Ile
        530                 535                 540

AGT CGT CAC TCA CTG GTT TCA TCA TAT CTG GCG TTA ATG GAG TTC AGT     1680
Ser Arg His Ser Leu Val Ser Ser Tyr Leu Ala Leu Met Glu Phe Ser
545                 550                 555                 560

GGT AAT ACA ATG ACC AGA GAT GCA TCC AGA GCA GTT CTG CGT TTT GTC     1728
Gly Asn Thr Met Thr Arg Asp Ala Ser Arg Ala Val Leu Arg Phe Val
                565                 570                 575

ACT GTC ACA GCA GAA GCC TTA CGC TTC AGG CAG ATA CAG AGA GAA TTT     1776
Thr Val Thr Ala Glu Ala Leu Arg Phe Arg Gln Ile Gln Arg Glu Phe
            580                 585                 590

CGT CAG GCA CTG TCT GAA ACT GCT CCT GTG TAT ACG ATG ACG CCG GGA     1824
Arg Gln Ala Leu Ser Glu Thr Ala Pro Val Tyr Thr Met Thr Pro Gly
        595                 600                 605

GAC GTG GAC CTC ACT CTG AAC TGG GGG CGA ATC AGC AAT GTG CTT CCG     1872
Asp Val Asp Leu Thr Leu Asn Trp Gly Arg Ile Ser Asn Val Leu Pro
    610                 615                 620

GAG TAT CGG GGA GAG GAT GGT GTC AGA GTG GGG AGA ATA TCC TTT AAT     1920
Glu Tyr Arg Gly Glu Asp Gly Val Arg Val Gly Arg Ile Ser Phe Asn
625                 630                 635                 640

AAT ATA TCA GCG ATA CTG GGG ACT GTG GCC GTT ATA CTG AAT TGC CAT     1968
Asn Ile Ser Ala Ile Leu Gly Thr Val Ala Val Ile Leu Asn Cys His
                645                 650                 655

CAT CAG GGG GCG CGT TCT GTT CGC GCC GTG AAT GAA GAG AGT CAA CCA     2016
His Gln Gly Ala Arg Ser Val Arg Ala Val Asn Glu Glu Ser Gln Pro
            660                 665                 670

GAA TGT CAG ATA ACT GGC GAC AGG CCT GTT ATA AAA ATA AAC AAT ACA     2064
Glu Cys Gln Ile Thr Gly Asp Arg Pro Val Ile Lys Ile Asn Asn Thr
        675                 680                 685

TTA TGG GAA AGT AAT ACA GCT GCA GCG TTT CTG AAC AGA AAG TCA CAG     2112
Leu Trp Glu Ser Asn Thr Ala Ala Ala Phe Leu Asn Arg Lys Ser Gln
    690                 695                 700

TTT TTA TAT ACA ACG GGT AAA TAA                                     2136
Phe Leu Tyr Thr Thr Gly Lys  *
705                 710
```

(2) INFORMATION FOR SEQ ID NO:35:

(i) SEQUENCE CHARACTERISTICS:
        (A) LENGTH: 711 amino acids
        (B) TYPE: amino acid
        (D) TOPOLOGY: linear (ii) MOLECULE TYPE: protein (xi) SEQUENCE DESCRIPTION: SEQ ID NO:35:

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
                20                  25                  30

Leu Val Ile Trp Ile Asn Gly Asp Lys Gly Tyr Asn Gly Leu Ala Glu
            35                  40                  45

Val Gly Lys Lys Phe Glu Lys Asp Thr Gly Ile Lys Val Thr Val Glu
        50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95
```

-continued

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
            165                 170                 175

Leu Gln Glu Pro Tyr Phe Thr Trp Pro Leu Ile Ala Ala Asp Gly Gly
        180                 185                 190

Tyr Ala Phe Lys Tyr Glu Asn Gly Lys Tyr Asp Ile Lys Asp Val Gly
    195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
            245                 250                 255

Ala Trp Ser Asn Ile Asp Thr Ser Lys Val Asn Tyr Gly Val Thr Val
        260                 265                 270

Leu Pro Thr Phe Lys Gly Gln Pro Ser Lys Pro Phe Val Gly Val Leu
    275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
            325                 330                 335

Leu Ala Lys Asp Pro Arg Ile Ala Ala Thr Met Glu Asn Ala Gln Lys
        340                 345                 350

Gly Glu Ile Met Pro Asn Ile Pro Gln Met Ser Ala Phe Trp Tyr Ala
    355                 360                 365

Val Arg Thr Ala Val Ile Asn Ala Ala Ser Gly Arg Gln Thr Val Asp
    370                 375                 380

Glu Ala Leu Lys Asp Ala Gln Thr Ser Ser Ser Asn Asn Asn Asn Asn
385                 390                 395                 400

Asn Asn Asn Asn Asn Leu Gly Ile Glu Gly Arg Ile Ser Glu Phe Arg
            405                 410                 415

Glu Phe Thr Ile Asp Phe Ser Thr Gln Gln Ser Tyr Val Ser Ser Leu
        420                 425                 430

Asn Ser Ile Arg Thr Glu Ile Ser Thr Pro Leu Glu His Ile Ser Gln
    435                 440                 445

Gly Thr Thr Ser Val Ser Val Ile Asn His Thr His Gly Ser Tyr Phe
    450                 455                 460

Ala Val Asp Ile Arg Gly Leu Asp Val Tyr Gln Ala Arg Phe Asp His
465                 470                 475                 480

Leu Arg Leu Ile Ile Glu Gln Asn Asn Leu Tyr Val Ala Gly Phe Val
            485                 490                 495

Asn Thr Ala Thr Asn Thr Phe Tyr Arg Phe Ser Asp Phe Thr His Ile
        500                 505                 510

-continued

```
Ser Val Pro Gly Val Thr Thr Val Ser Met Thr Thr Asp Ser Ser Tyr
            515                 520                 525

Thr Thr Leu Gln Arg Val Ala Ala Leu Glu Arg Ser Gly Met Gln Ile
        530                 535                 540

Ser Arg His Ser Leu Val Ser Ser Tyr Leu Ala Leu Met Glu Phe Ser
545                 550                 555                 560

Gly Asn Thr Met Thr Arg Asp Ala Ser Arg Ala Val Leu Arg Phe Val
                565                 570                 575

Thr Val Thr Ala Glu Ala Leu Arg Phe Arg Gln Ile Gln Arg Glu Phe
            580                 585                 590

Arg Gln Ala Leu Ser Glu Thr Ala Pro Val Tyr Thr Met Thr Pro Gly
        595                 600                 605

Asp Val Asp Leu Thr Leu Asn Trp Gly Arg Ile Ser Asn Val Leu Pro
            610                 615                 620

Glu Tyr Arg Gly Glu Asp Gly Val Arg Val Gly Arg Ile Ser Phe Asn
625                 630                 635                 640

Asn Ile Ser Ala Ile Leu Gly Thr Val Ala Val Ile Leu Asn Cys His
                645                 650                 655

His Gln Gly Ala Arg Ser Val Arg Ala Val Asn Glu Glu Ser Gln Pro
            660                 665                 670

Glu Cys Gln Ile Thr Gly Asp Arg Pro Val Ile Lys Ile Asn Asn Thr
        675                 680                 685

Leu Trp Glu Ser Asn Thr Ala Ala Ala Phe Leu Asn Arg Lys Ser Gln
        690                 695                 700

Phe Leu Tyr Thr Thr Gly Lys
705                 710
```

(2) INFORMATION FOR SEQ ID NO:36:

(i) SEQUENCE CHARACTERISTICS:
        (A) LENGTH: 981 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..981

(xi) SEQUENCE DESCRIPTION: SEQ ID NO:36:

```
ATG AAA AAG ACA GCT ATC GCG ATT GCA GTG GCA CTG GCT GGT TTC GCT      48
Met Lys Lys Thr Ala Ile Ala Ile Ala Val Ala Leu Ala Gly Phe Ala
  1               5                  10                  15

ACC GTT GCG CAA GCT GAC TAC AAG GAC GAC GAT GAC AAG AAG CTT GAA      96
Thr Val Ala Gln Ala Asp Tyr Lys Asp Asp Asp Asp Lys Lys Leu Glu
             20                  25                  30

TTC AAG GAA TTT ACC TTA GAC TTC TCG ACT GCA AAG ACG TAT GTA GAT     144
Phe Lys Glu Phe Thr Leu Asp Phe Ser Thr Ala Lys Thr Tyr Val Asp
         35                  40                  45

TCG CTG AAT GTC ATT CGC TCT GCA ATA GGT ACT CCA TTA CAG ACT ATT     192
Ser Leu Asn Val Ile Arg Ser Ala Ile Gly Thr Pro Leu Gln Thr Ile
     50                  55                  60

TCA TCA GGA GGT ACG TCT TTA CTG ATG ATT GAT AGT GGC TCA GGG GAT     240
Ser Ser Gly Gly Thr Ser Leu Leu Met Ile Asp Ser Gly Ser Gly Asp
 65                  70                  75                  80

AAT TTG TTT GCA GTT GAT GTC AGA GGG ATA GAT GCA GAG GAA GGG CGG     288
Asn Leu Phe Ala Val Asp Val Arg Gly Ile Asp Ala Glu Glu Gly Arg
                 85                  90                  95
```

```
TTT AAT AAT CTA CGG CTT ATT GTT GAA CGA AAT AAT TTA TAT GTG ACA         336
Phe Asn Asn Leu Arg Leu Ile Val Glu Arg Asn Asn Leu Tyr Val Thr
            100                 105                 110

GGA TTT GTT AAC AGG ACA AAT AAT GTT TTT TAT CGC TTT GCT GAT TTT         384
Gly Phe Val Asn Arg Thr Asn Asn Val Phe Tyr Arg Phe Ala Asp Phe
            115                 120                 125

TCA CAT GTT ACC TTT CCA GGT ACA ACA GCG GTT ACA TTG TCT GGT GAC         432
Ser His Val Thr Phe Pro Gly Thr Thr Ala Val Thr Leu Ser Gly Asp
        130                 135                 140

AGT AGC TAT ACC ACG TTA CAG CGT GTT GCA GGG ATC AGT CGT ACG GGG         480
Ser Ser Tyr Thr Thr Leu Gln Arg Val Ala Gly Ile Ser Arg Thr Gly
145                 150                 155                 160

ATG CAG ATA AAT CGC CAT TCG TTG ACT ACT TCT TAT CTG GAT TTA ATG         528
Met Gln Ile Asn Arg His Ser Leu Thr Thr Ser Tyr Leu Asp Leu Met
                165                 170                 175

TCG CAT AGT GGA ACC TCA CTG ACG CAG TCT GTG GCA AGA GCG ATG TTA         576
Ser His Ser Gly Thr Ser Leu Thr Gln Ser Val Ala Arg Ala Met Leu
            180                 185                 190

CGG TTT GTT ACT GTG ACA GCT GAA GCT TTA CGT TTT CGG CAA ATA CAG         624
Arg Phe Val Thr Val Thr Ala Glu Ala Leu Arg Phe Arg Gln Ile Gln
            195                 200                 205

AGG GGA TTT CGT ACA ACA CTG GAT GAT CTC AGT GGG CGT TCT TAT GTA         672
Arg Gly Phe Arg Thr Thr Leu Asp Asp Leu Ser Gly Arg Ser Tyr Val
    210                 215                 220

ATG ACT GCT GAA GAT GTT GAT CTT ACA TTG AAC TGG GGA AGG TTG AGT         720
Met Thr Ala Glu Asp Val Asp Leu Thr Leu Asn Trp Gly Arg Leu Ser
225                 230                 235                 240

AGC GTC CTG CCT GAC TAT CAT GGA CAA GAC TCT GTT CGT GTA GGA AGA         768
Ser Val Leu Pro Asp Tyr His Gly Gln Asp Ser Val Arg Val Gly Arg
                245                 250                 255

ATT TCT TTT GGA AGC ATT AAT GCA ATT CTG GGA AGC GTG GCA TTA ATA         816
Ile Ser Phe Gly Ser Ile Asn Ala Ile Leu Gly Ser Val Ala Leu Ile
            260                 265                 270

CTG AAT TGT CAT CAT CAT GCA TCG CGA GTT GCC AGA ATG GCA TCT GAT         864
Leu Asn Cys His His His Ala Ser Arg Val Ala Arg Met Ala Ser Asp
            275                 280                 285

GAG TTT CCT TCT ATG TGT CCG GCA GAT GGA AGA GTC CGT GGG ATT ACG         912
Glu Phe Pro Ser Met Cys Pro Ala Asp Gly Arg Val Arg Gly Ile Thr
    290                 295                 300

CAC AAT AAA ATA TTG TGG GAT TCA TCC ACT CTG GGG GCA ATT CTG ATG         960
His Asn Lys Ile Leu Trp Asp Ser Ser Thr Leu Gly Ala Ile Leu Met
305                 310                 315                 320

CGC AGA ACT ATT AGC AGT TGA                                             981
Arg Arg Thr Ile Ser Ser  *
                325
```

(2) INFORMATION FOR SEQ ID NO:37:

(i) SEQUENCE CHARACTERISTICS:
        (A) LENGTH:   326 amino acids
        (B) TYPE: amino acid
        (D) TOPOLOGY: linear (ii) MOLECULE TYPE: protein (xi) SEQUENCE DESCRIPTION: SEQ ID NO:37:

```
Met Lys Lys Thr Ala Ile Ala Ile Ala Val Ala Leu Ala Gly Phe Ala
 1               5                  10                  15

Thr Val Ala Gln Ala Asp Tyr Lys Asp Asp Asp Lys Lys Leu Glu
            20                  25                  30
```

```
Phe Lys Glu Phe Thr Leu Asp Phe Ser Thr Ala Lys Thr Tyr Val Asp
         35                  40                  45

Ser Leu Asn Val Ile Arg Ser Ala Ile Gly Thr Pro Leu Gln Thr Ile
 50                  55                  60

Ser Ser Gly Gly Thr Ser Leu Leu Met Ile Asp Ser Gly Ser Gly Asp
 65                  70                  75                  80

Asn Leu Phe Ala Val Asp Val Arg Gly Ile Asp Ala Glu Glu Gly Arg
                 85                  90                  95

Phe Asn Asn Leu Arg Leu Ile Val Glu Arg Asn Asn Leu Tyr Val Thr
                100                 105                 110

Gly Phe Val Asn Arg Thr Asn Asn Val Phe Tyr Arg Phe Ala Asp Phe
            115                 120                 125

Ser His Val Thr Phe Pro Gly Thr Thr Ala Val Thr Leu Ser Gly Asp
130                 135                 140

Ser Ser Tyr Thr Thr Leu Gln Arg Val Ala Gly Ile Ser Arg Thr Gly
145                 150                 155                 160

Met Gln Ile Asn Arg His Ser Leu Thr Thr Ser Tyr Leu Asp Leu Met
                165                 170                 175

Ser His Ser Gly Thr Ser Leu Thr Gln Ser Val Ala Arg Ala Met Leu
            180                 185                 190

Arg Phe Val Thr Val Thr Ala Glu Ala Leu Arg Phe Arg Gln Ile Gln
        195                 200                 205

Arg Gly Phe Arg Thr Thr Leu Asp Asp Leu Ser Gly Arg Ser Tyr Val
    210                 215                 220

Met Thr Ala Glu Asp Val Asp Leu Thr Leu Asn Trp Gly Arg Leu Ser
225                 230                 235                 240

Ser Val Leu Pro Asp Tyr His Gly Gln Asp Ser Val Arg Val Gly Arg
                245                 250                 255

Ile Ser Phe Gly Ser Ile Asn Ala Ile Leu Gly Ser Val Ala Leu Ile
            260                 265                 270

Leu Asn Cys His His His Ala Ser Arg Val Ala Arg Met Ala Ser Asp
        275                 280                 285

Glu Phe Pro Ser Met Cys Pro Ala Asp Gly Arg Val Arg Gly Ile Thr
    290                 295                 300

His Asn Lys Ile Leu Trp Asp Ser Ser Thr Leu Gly Ala Ile Leu Met
305                 310                 315                 320

Arg Arg Thr Ile Ser Ser
                325

(2) INFORMATION FOR SEQ ID NO:38:

(i) SEQUENCE CHARACTERISTICS:
        (A) LENGTH: 990 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..990

(xi) SEQUENCE DESCRIPTION: SEQ ID NO:38:

ATG AAA AAG ACA GCT ATC GCG ATT GCA GTG GCA CTG GCT GGT TTC GCT      48
Met Lys Lys Thr Ala Ile Ala Ile Ala Val Ala Leu Ala Gly Phe Ala
 1               5                  10                  15

ACC GTT GCG CAA GCT GAC TAC AAG GAC GAC GAT GAC AAG AAG CTT GAA      96
```

```
        Thr Val Ala Gln Ala Asp Tyr Lys Asp Asp Asp Lys Lys Leu Glu
                     20                  25                  30

TTC CGG GAG TTT ACG ATA GAC TTT TCG ACC CAA CAA AGT TAT GTC TCT      144
Phe Arg Glu Phe Thr Ile Asp Phe Ser Thr Gln Gln Ser Tyr Val Ser
             35                  40                  45

TCG TTA AAT AGT ATA CGG ACA GAG ATA TCG ACC CCT CTT GAA CAT ATA      192
Ser Leu Asn Ser Ile Arg Thr Glu Ile Ser Thr Pro Leu Glu His Ile
         50                  55                  60

TCT CAG GGG ACC ACA TCG GTG TCT GTT ATT AAC CAC ACC CAC GGC AGT      240
Ser Gln Gly Thr Thr Ser Val Ser Val Ile Asn His Thr His Gly Ser
 65                  70                  75                  80

TAT TTT GCT GTG GAT ATA CGA GGG CTT GAT GTC TAT CAG GCG CGT TTT      288
Tyr Phe Ala Val Asp Ile Arg Gly Leu Asp Val Tyr Gln Ala Arg Phe
                 85                  90                  95

GAC CAT CTT CGT CTG ATT ATT GAG CAA AAT AAT TTA TAT GTG GCA GGG      336
Asp His Leu Arg Leu Ile Ile Glu Gln Asn Asn Leu Tyr Val Ala Gly
             100                 105                 110

TTC GTT AAT ACG GCA ACA AAT ACT TTC TAC CGT TTT TCA GAT TTT ACA      384
Phe Val Asn Thr Ala Thr Asn Thr Phe Tyr Arg Phe Ser Asp Phe Thr
         115                 120                 125

CAT ATA TCA GTG CCC GGT GTG ACA ACG GTT TCC ATG ACA ACG GAC AGC      432
His Ile Ser Val Pro Gly Val Thr Thr Val Ser Met Thr Thr Asp Ser
    130                 135                 140

AGT TAT ACC ACT CTG CAA CGT GTC GCA GCG CTG GAA CGT TCC GGA ATG      480
Ser Tyr Thr Thr Leu Gln Arg Val Ala Ala Leu Glu Arg Ser Gly Met
145                 150                 155                 160

CAA ATC AGT CGT CAC TCA CTG GTT TCA TCA TAT CTG GCG TTA ATG GAG      528
Gln Ile Ser Arg His Ser Leu Val Ser Ser Tyr Leu Ala Leu Met Glu
                 165                 170                 175

TTC AGT GGT AAT ACA ATG ACC AGA GAT GCA TCC AGA GCA GTT CTG CGT      576
Phe Ser Gly Asn Thr Met Thr Arg Asp Ala Ser Arg Ala Val Leu Arg
             180                 185                 190

TTT GTC ACT GTC ACA GCA GAA GCC TTA CGC TTC AGG CAG ATA CAG AGA      624
Phe Val Thr Val Thr Ala Glu Ala Leu Arg Phe Arg Gln Ile Gln Arg
         195                 200                 205

GAA TTT CGT CAG GCA CTG TCT GAA ACT GCT CCT GTG TAT ACG ATG ACG      672
Glu Phe Arg Gln Ala Leu Ser Glu Thr Ala Pro Val Tyr Thr Met Thr
    210                 215                 220

CCG GGA GAC GTG GAC CTC ACT CTG AAC TGG GGG CGA ATC AGC AAT GTG      720
Pro Gly Asp Val Asp Leu Thr Leu Asn Trp Gly Arg Ile Ser Asn Val
225                 230                 235                 240

CTT CCG GAG TAT CGG GGA GAG GAT GGT GTC AGA GTG GGG AGA ATA TCC      768
Leu Pro Glu Tyr Arg Gly Glu Asp Gly Val Arg Val Gly Arg Ile Ser
                 245                 250                 255

TTT AAT AAT ATA TCA GCG ATA CTG GGG ACT GTG GCC GTT ATA CTG AAT      816
Phe Asn Asn Ile Ser Ala Ile Leu Gly Thr Val Ala Val Ile Leu Asn
             260                 265                 270

TGC CAT CAT CAG GGG GCG CGT TCT GTT CGC GCC GTG AAT GAA GAG AGT      864
Cys His His Gln Gly Ala Arg Ser Val Arg Ala Val Asn Glu Glu Ser
         275                 280                 285

CAA CCA GAA TGT CAG ATA ACT GGC GAC AGG CCT GTT ATA AAA ATA AAC      912
Gln Pro Glu Cys Gln Ile Thr Gly Asp Arg Pro Val Ile Lys Ile Asn
    290                 295                 300

AAT ACA TTA TGG GAA AGT AAT ACA GCT GCA GCG TTT CTG AAC AGA AAG      960
Asn Thr Leu Trp Glu Ser Asn Thr Ala Ala Ala Phe Leu Asn Arg Lys
305                 310                 315                 320

TCA CAG TTT TTA TAT ACA ACG GGT AAA TAA                              990
Ser Gln Phe Leu Tyr Thr Thr Gly Lys *
                 325                 330
```

(2) INFORMATION FOR SEQ ID NO:39:

(i) SEQUENCE CHARACTERISTICS:
        (A) LENGTH: 329 amino acids
        (B) TYPE: amino acid
        (D) TOPOLOGY: linear (ii) MOLECULE TYPE: protein (xi) SEQUENCE DESCRIPTION: SEQ ID NO:39:

```
Met Lys Lys Thr Ala Ile Ala Ile Ala Val Ala Leu Ala Gly Phe Ala
 1               5                  10                  15

Thr Val Ala Gln Ala Asp Tyr Lys Asp Asp Asp Lys Lys Leu Glu
             20                  25                  30

Phe Arg Glu Phe Thr Ile Asp Phe Ser Thr Gln Gln Ser Tyr Val Ser
         35                  40                  45

Ser Leu Asn Ser Ile Arg Thr Glu Ile Ser Thr Pro Leu Glu His Ile
     50                  55                  60

Ser Gln Gly Thr Thr Ser Val Ser Val Ile Asn His Thr His Gly Ser
 65                  70                  75                  80

Tyr Phe Ala Val Asp Ile Arg Gly Leu Asp Val Tyr Gln Ala Arg Phe
                 85                  90                  95

Asp His Leu Arg Leu Ile Ile Glu Gln Asn Asn Leu Tyr Val Ala Gly
            100                 105                 110

Phe Val Asn Thr Ala Thr Asn Thr Phe Tyr Arg Phe Ser Asp Phe Thr
        115                 120                 125

His Ile Ser Val Pro Gly Val Thr Thr Val Ser Met Thr Thr Asp Ser
    130                 135                 140

Ser Tyr Thr Thr Leu Gln Arg Val Ala Ala Leu Glu Arg Ser Gly Met
145                 150                 155                 160

Gln Ile Ser Arg His Ser Leu Val Ser Ser Tyr Leu Ala Leu Met Glu
                165                 170                 175

Phe Ser Gly Asn Thr Met Thr Arg Asp Ala Ser Arg Ala Val Leu Arg
            180                 185                 190

Phe Val Thr Val Thr Ala Glu Ala Leu Arg Phe Arg Gln Ile Gln Arg
        195                 200                 205

Glu Phe Arg Gln Ala Leu Ser Glu Thr Ala Pro Val Tyr Thr Met Thr
    210                 215                 220

Pro Gly Asp Val Asp Leu Thr Leu Asn Trp Gly Arg Ile Ser Asn Val
225                 230                 235                 240

Leu Pro Glu Tyr Arg Gly Glu Asp Gly Val Arg Val Gly Arg Ile Ser
                245                 250                 255

Phe Asn Asn Ile Ser Ala Ile Leu Gly Thr Val Ala Val Ile Leu Asn
            260                 265                 270

Cys His His Gln Gly Ala Arg Ser Val Arg Ala Val Asn Glu Glu Ser
        275                 280                 285

Gln Pro Glu Cys Gln Ile Thr Gly Asp Arg Pro Val Ile Lys Ile Asn
    290                 295                 300

Asn Thr Leu Trp Glu Ser Asn Thr Ala Ala Ala Phe Leu Asn Arg Lys
305                 310                 315                 320

Ser Gln Phe Leu Tyr Thr Thr Gly Lys
                325                 330
```

(2) INFORMATION FOR SEQ ID NO:40:

(i) SEQUENCE CHARACTERISTICS:

```
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:40:

GCCATATGAA GGAATTTACC TTAGAC                                            26

(2) INFORMATION FOR SEQ ID NO:41:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:41:

GCCATATGCG GGAGTTTACG ATAGAC                                            26

(2) INFORMATION FOR SEQ ID NO:42:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:42:

GCCATATGAC GCCTGATTGT GTAACT                                            26

(2) INFORMATION FOR SEQ ID NO:43:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:43:

GCCATATGGC GGATTGTGCT AAAGG                                             25

(2) INFORMATION FOR SEQ ID NO:44:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:44:

GGCTCGAGTC AACGAAAAAT AACTTCGCTG AA                                     32

(2) INFORMATION FOR SEQ ID NO:45:
```

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:45:

GGCTCGAGTC AGTCATTATT AAACTGCACT TC                                    32

(2) INFORMATION FOR SEQ ID NO:46:

(i) SEQUENCE CHARACTERISTICS:
            (A) LENGTH: 2073 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "DNA"

(ix) FEATURE:
            (A) NAME/KEY: CDS
            (B) LOCATION: 1..2070

(xi) SEQUENCE DESCRIPTION: SEQ ID NO:46:

ATG AAA ATC GAA GAA GGT AAA CTG GTA ATC TGG ATT AAC GGC GAT AAA         48
Met Lys Ile Glu Glu Gly Lys Leu Val Ile Trp Ile Asn Gly Asp Lys
  1               5                  10                  15

GGC TAT AAC GGT CTC GCT GAA GTC GGT AAG AAA TTC GAG AAA GAT ACC         96
Gly Tyr Asn Gly Leu Ala Glu Val Gly Lys Lys Phe Glu Lys Asp Thr
             20                  25                  30

GGA ATT AAA GTC ACC GTT GAG CAT CCG GAT AAA CTG GAA GAG AAA TTC        144
Gly Ile Lys Val Thr Val Glu His Pro Asp Lys Leu Glu Glu Lys Phe
         35                  40                  45

CCA CAG GTT GCG GCA ACT GGC GAT GGC CCT GAC ATT ATC TTC TGG GCA        192
Pro Gln Val Ala Ala Thr Gly Asp Gly Pro Asp Ile Ile Phe Trp Ala
     50                  55                  60

CAC GAC CGC TTT GGT GGC TAC GCT CAA TCT GGC CTG TTG GCT GAA ATC        240
His Asp Arg Phe Gly Gly Tyr Ala Gln Ser Gly Leu Leu Ala Glu Ile
 65                  70                  75                  80

ACC CCG GAC AAA GCG TTC CAG GAC AAG CTG TAT CCG TTT ACC TGG GAT        288
Thr Pro Asp Lys Ala Phe Gln Asp Lys Leu Tyr Pro Phe Thr Trp Asp
                 85                  90                  95

GCC GTA CGT TAC AAC GGC AAG CTG ATT GCT TAC CCG ATC GCT GTT GAA        336
Ala Val Arg Tyr Asn Gly Lys Leu Ile Ala Tyr Pro Ile Ala Val Glu
            100                 105                 110

GCG TTA TCG CTG ATT TAT AAC AAA GAT CTG CTG CCG AAC CCG CCA AAA        384
Ala Leu Ser Leu Ile Tyr Asn Lys Asp Leu Leu Pro Asn Pro Pro Lys
        115                 120                 125

ACC TGG GAA GAG ATC CCG GCG CTG GAT AAA GAA CTG AAA GCG AAA GGT        432
Thr Trp Glu Glu Ile Pro Ala Leu Asp Lys Glu Leu Lys Ala Lys Gly
    130                 135                 140

AAG AGC GCG CTG ATG TTC AAC CTG CAA GAA CCG TAC TTC ACC TGG CCG        480
Lys Ser Ala Leu Met Phe Asn Leu Gln Glu Pro Tyr Phe Thr Trp Pro
145                 150                 155                 160

CTG ATT GCT GCT GAC GGG GGT TAT GCG TTC AAG TAT GAA AAC GGC AAG        528
Leu Ile Ala Ala Asp Gly Gly Tyr Ala Phe Lys Tyr Glu Asn Gly Lys
                165                 170                 175

TAC GAC ATT AAA GAC GTG GGC GTG GAT AAC GCT GGC GCG AAA GCG GGT        576
Tyr Asp Ile Lys Asp Val Gly Val Asp Asn Ala Gly Ala Lys Ala Gly
            180                 185                 190

```
CTG ACC TTC CTG GTT GAC CTG ATT AAA AAC AAA CAC ATG AAT GCA GAC      624
Leu Thr Phe Leu Val Asp Leu Ile Lys Asn Lys His Met Asn Ala Asp
        195                 200                 205

ACC GAT TAC TCC ATC GCA GAA GCT GCC TTT AAT AAA GGC GAA ACA GCG      672
Thr Asp Tyr Ser Ile Ala Glu Ala Ala Phe Asn Lys Gly Glu Thr Ala
    210                 215                 220

ATG ACC ATC AAC GGC CCG TGG GCA TGG TCC AAC ATC GAC ACC AGC AAA      720
Met Thr Ile Asn Gly Pro Trp Ala Trp Ser Asn Ile Asp Thr Ser Lys
225                 230                 235                 240

GTG AAT TAT GGT GTA ACG GTA CTG CCG ACC TTC AAG GGT CAA CCA TCC      768
Val Asn Tyr Gly Val Thr Val Leu Pro Thr Phe Lys Gly Gln Pro Ser
                245                 250                 255

AAA CCG TTC GTT GGC GTG CTG AGC GCA GGT ATT AAC GCC GCC AGT CCG      816
Lys Pro Phe Val Gly Val Leu Ser Ala Gly Ile Asn Ala Ala Ser Pro
        260                 265                 270

AAC AAA GAG CTG GCA AAA GAG TTC CTC GAA AAC TAT CTG CTG ACT GAT      864
Asn Lys Glu Leu Ala Lys Glu Phe Leu Glu Asn Tyr Leu Leu Thr Asp
    275                 280                 285

GAA GGT CTG GAA GCG GTT AAT AAA GAC AAA CCG CTG GGT GCC GTA GCG      912
Glu Gly Leu Glu Ala Val Asn Lys Asp Lys Pro Leu Gly Ala Val Ala
290                 295                 300

CTG AAG TCT TAC GAG GAA GAG TTG GCG AAA GAT CCA CGT ATT GCC GCC      960
Leu Lys Ser Tyr Glu Glu Glu Leu Ala Lys Asp Pro Arg Ile Ala Ala
305                 310                 315                 320

ACC ATG GAA AAC GCC CAG AAA GGT GAA ATC ATG CCG AAC ATC CCG CAG     1008
Thr Met Glu Asn Ala Gln Lys Gly Glu Ile Met Pro Asn Ile Pro Gln
                325                 330                 335

ATG TCC GCT TTC TGG TAT GCC GTG CGT ACT GCG GTG ATC AAC GCC GCC     1056
Met Ser Ala Phe Trp Tyr Ala Val Arg Thr Ala Val Ile Asn Ala Ala
        340                 345                 350

AGC GGT CGT CAG ACT GTC GAT GAA GCC CTG AAA GAC GCG CAG ACT AAT     1104
Ser Gly Arg Gln Thr Val Asp Glu Ala Leu Lys Asp Ala Gln Thr Asn
    355                 360                 365

TCG AGC TCG AAC AAC AAC AAC AAT AAC AAT AAC AAC AAC CTC GGG ATC     1152
Ser Ser Ser Asn Asn Asn Asn Asn Asn Asn Asn Asn Asn Leu Gly Ile
370                 375                 380

GAG GGA AGG ATT TCA GAA TTC GGA TCC GCC CCG GAA TTC AAG GAA TTT     1200
Glu Gly Arg Ile Ser Glu Phe Gly Ser Ala Pro Glu Phe Lys Glu Phe
385                 390                 395                 400

ACC TTA GAC TTC TCG ACT GCA AAG ACG TAT GTA GAT TCG CTG AAT GTC     1248
Thr Leu Asp Phe Ser Thr Ala Lys Thr Tyr Val Asp Ser Leu Asn Val
                405                 410                 415

ATT CGC TCT GCA ATA GGT ACT CCA TTA CAG ACT ATT TCA TCA GGA GGT     1296
Ile Arg Ser Ala Ile Gly Thr Pro Leu Gln Thr Ile Ser Ser Gly Gly
        420                 425                 430

ACG TCT TTA CTG ATG ATT GAT AGT GGC TCA GGG GAT AAT TTG TTT GCA     1344
Thr Ser Leu Leu Met Ile Asp Ser Gly Ser Gly Asp Asn Leu Phe Ala
    435                 440                 445

GTT GAT GTC AGA GGG ATA GAT CCA GAG GAA GGG CGG TTT AAT AAT CTA     1392
Val Asp Val Arg Gly Ile Asp Pro Glu Glu Gly Arg Phe Asn Asn Leu
450                 455                 460

CGG CTT ATT GTT GAA CGA AAT AAT TTA TAT GTG ACA GGA TTT GTT AAC     1440
Arg Leu Ile Val Glu Arg Asn Asn Leu Tyr Val Thr Gly Phe Val Asn
465                 470                 475                 480

AGG ACA AAT AAT GTT TTT TAT CGC TTT GCT GAT TTT TCA CAT GTT ACC     1488
Arg Thr Asn Asn Val Phe Tyr Arg Phe Ala Asp Phe Ser His Val Thr
                485                 490                 495

TTT CCA GGT ACA ACA GCG GTT ACA TTG TCT GGT GAC AGT AGC TAT ACC     1536
Phe Pro Gly Thr Thr Ala Val Thr Leu Ser Gly Asp Ser Ser Tyr Thr
        500                 505                 510
```

-continued

```
ACG TTA CAG CGT GTT GCA GGG ATC AGT CGT ACG GGG ATG CAG ATA AAT    1584
Thr Leu Gln Arg Val Ala Gly Ile Ser Arg Thr Gly Met Gln Ile Asn
        515                 520                 525

CGC CAT TCG TTG ACT ACT TCT TAT CTG GAT TTA ATG TCG CAT AGT GGA    1632
Arg His Ser Leu Thr Thr Ser Tyr Leu Asp Leu Met Ser His Ser Gly
        530                 535                 540

ACC TCA CTG ACG CAG TCT GTG GCA AGA GCG ATG TTA CGG TTT GTT ACT    1680
Thr Ser Leu Thr Gln Ser Val Ala Arg Ala Met Leu Arg Phe Val Thr
545                 550                 555                 560

GTG ACA GCT GAA GCT TTA CGT TTT CGG CAA ATA CAG AGG GGA TTT CGT    1728
Val Thr Ala Glu Ala Leu Arg Phe Arg Gln Ile Gln Arg Gly Phe Arg
                565                 570                 575

ACA ACA CTG GAT GAT CTC AGT GGG CGT TCT TAT GTA ATG ACT GCT GAA    1776
Thr Thr Leu Asp Asp Leu Ser Gly Arg Ser Tyr Val Met Thr Ala Glu
        580                 585                 590

GAT GTT GAT CTT ACA TTG AAC TGG GGA AGG TTG AGT AGC GTC CTG CCT    1824
Asp Val Asp Leu Thr Leu Asn Trp Gly Arg Leu Ser Ser Val Leu Pro
        595                 600                 605

GAC TAT CAT GGA CAA GAC TCT GTT CGT GTA GGA AGA ATT TCT TTT GGA    1872
Asp Tyr His Gly Gln Asp Ser Val Arg Val Gly Arg Ile Ser Phe Gly
        610                 615                 620

AGC ATT AAT GCA ATT CTG GGA AGC GTG GCA TTA ATA CTG AAT TGT CAT    1920
Ser Ile Asn Ala Ile Leu Gly Ser Val Ala Leu Ile Leu Asn Cys His
625                 630                 635                 640

CAT CAT GCA TCG CGA GTT GCC AGA ATG GCA TCT GAT GAG TTT CCT TCT    1968
His His Ala Ser Arg Val Ala Arg Met Ala Ser Asp Glu Phe Pro Ser
                645                 650                 655

ATG TGT CCG GCA GAT GGA AGA GTC CGT GGG ATT ACG CAC AAT AAA ATA    2016
Met Cys Pro Ala Asp Gly Arg Val Arg Gly Ile Thr His Asn Lys Ile
        660                 665                 670

TTG TGG GAT TCA TCC ACT CTG GGG GCA ATT CTG ATG CGC AGA ACT ATT    2064
Leu Trp Asp Ser Ser Thr Leu Gly Ala Ile Leu Met Arg Arg Thr Ile
        675                 680                 685

AGC AGT TGA                                                        2073
Ser Ser
    690
```

(2) INFORMATION FOR SEQ ID NO:47:

(i) SEQUENCE CHARACTERISTICS:
        (A) LENGTH: 690 amino acids
        (B) TYPE: amino acid
        (D) TOPOLOGY: linear (ii) MOLECULE TYPE: protein (xi) SEQUENCE DESCRIPTION: SEQ ID NO:47:

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95
```

-continued

```
Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Gly Ser Ala Pro Glu Phe Lys Glu Phe
385                 390                 395                 400

Thr Leu Asp Phe Ser Thr Ala Lys Thr Tyr Val Asp Ser Leu Asn Val
                405                 410                 415

Ile Arg Ser Ala Ile Gly Thr Pro Leu Gln Thr Ile Ser Ser Gly Gly
            420                 425                 430

Thr Ser Leu Leu Met Ile Asp Ser Gly Ser Gly Asp Asn Leu Phe Ala
        435                 440                 445

Val Asp Val Arg Gly Ile Asp Pro Glu Glu Gly Arg Phe Asn Asn Leu
    450                 455                 460

Arg Leu Ile Val Glu Arg Asn Asn Leu Tyr Val Thr Gly Phe Val Asn
465                 470                 475                 480

Arg Thr Asn Asn Val Phe Tyr Arg Phe Ala Asp Phe Ser His Val Thr
                485                 490                 495

Phe Pro Gly Thr Thr Ala Val Thr Leu Ser Gly Asp Ser Ser Tyr Thr
            500                 505                 510

Thr Leu Gln Arg Val Ala Gly Ile Ser Arg Thr Gly Met Gln Ile Asn
```

```
              515                 520                 525
Arg His Ser Leu Thr Thr Ser Tyr Leu Asp Leu Met Ser His Ser Gly
            530                 535                 540

Thr Ser Leu Thr Gln Ser Val Ala Arg Ala Met Leu Arg Phe Val Thr
545                 550                 555                 560

Val Thr Ala Glu Ala Leu Arg Phe Arg Gln Ile Gln Arg Gly Phe Arg
                565                 570                 575

Thr Thr Leu Asp Asp Leu Ser Gly Arg Ser Tyr Val Met Thr Ala Glu
            580                 585                 590

Asp Val Asp Leu Thr Leu Asn Trp Gly Arg Leu Ser Ser Val Leu Pro
                595                 600                 605

Asp Tyr His Gly Gln Asp Ser Val Arg Val Gly Arg Ile Ser Phe Gly
            610                 615                 620

Ser Ile Asn Ala Ile Leu Gly Ser Val Ala Leu Ile Leu Asn Cys His
625                 630                 635                 640

His His Ala Ser Arg Val Ala Arg Met Ala Ser Asp Glu Phe Pro Ser
                645                 650                 655

Met Cys Pro Ala Asp Gly Arg Val Arg Gly Ile Thr His Asn Lys Ile
            660                 665                 670

Leu Trp Asp Ser Ser Thr Leu Gly Ala Ile Leu Met Arg Arg Thr Ile
                675                 680                 685

Ser Ser
690

(2) INFORMATION FOR SEQ ID NO:48:

(i) SEQUENCE CHARACTERISTICS:
        (A) LENGTH: 2085 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 1..2082

(xi) SEQUENCE DESCRIPTION: SEQ ID NO:48:

ATG AAA ATC GAA GAA GGT AAA CTG GTA ATC TGG ATT AAC GGC GAT AAA        48
Met Lys Ile Glu Glu Gly Lys Leu Val Ile Trp Ile Asn Gly Asp Lys
1               5                   10                  15

GGC TAT AAC GGT CTC GCT GAA GTC GGT AAG AAA TTC GAG AAA GAT ACC        96
Gly Tyr Asn Gly Leu Ala Glu Val Gly Lys Lys Phe Glu Lys Asp Thr
                20                  25                  30

GGA ATT AAA GTC ACC GTT GAG CAT CCG GAT AAA CTG GAA GAG AAA TTC       144
Gly Ile Lys Val Thr Val Glu His Pro Asp Lys Leu Glu Glu Lys Phe
            35                  40                  45

CCA CAG GTT GCG GCA ACT GGC GAT GGC CCT GAC ATT ATC TTC TGG GCA       192
Pro Gln Val Ala Ala Thr Gly Asp Gly Pro Asp Ile Ile Phe Trp Ala
        50                  55                  60

CAC GAC CGC TTT GGT GGC TAC GCT CAA TCT GGC CTG TTG GCT GAA ATC       240
His Asp Arg Phe Gly Gly Tyr Ala Gln Ser Gly Leu Leu Ala Glu Ile
65                  70                  75                  80

ACC CCG GAC AAA GCG TTC CAG GAC AAG CTG TAT CCG TTT ACC TGG GAT       288
Thr Pro Asp Lys Ala Phe Gln Asp Lys Leu Tyr Pro Phe Thr Trp Asp
                85                  90                  95

GCC GTA CGT TAC AAC GGC AAG CTG ATT GCT TAC CCG ATC GCT GTT GAA       336
Ala Val Arg Tyr Asn Gly Lys Leu Ile Ala Tyr Pro Ile Ala Val Glu
```

```
                        100                     105                     110
GCG TTA TCG CTG ATT TAT AAC AAA GAT CTG CTG CCG AAC CCG CCA AAA         384
Ala Leu Ser Leu Ile Tyr Asn Lys Asp Leu Leu Pro Asn Pro Pro Lys
        115                     120                     125

ACC TGG GAA GAG ATC CCG GCG CTG GAT AAA GAA CTG AAA GCG AAA GGT         432
Thr Trp Glu Glu Ile Pro Ala Leu Asp Lys Glu Leu Lys Ala Lys Gly
        130                     135                     140

AAG AGC GCG CTG ATG TTC AAC CTG CAA GAA CCG TAC TTC ACC TGG CCG         480
Lys Ser Ala Leu Met Phe Asn Leu Gln Glu Pro Tyr Phe Thr Trp Pro
145                     150                     155                 160

CTG ATT GCT GCT GAC GGG GGT TAT GCG TTC AAG TAT GAA AAC GGC AAG         528
Leu Ile Ala Ala Asp Gly Gly Tyr Ala Phe Lys Tyr Glu Asn Gly Lys
                        165                     170                     175

TAC GAC ATT AAA GAC GTG GGC GTG GAT AAC GCT GGC GCG AAA GCG GGT         576
Tyr Asp Ile Lys Asp Val Gly Val Asp Asn Ala Gly Ala Lys Ala Gly
                        180                     185                     190

CTG ACC TTC CTG GTT GAC CTG ATT AAA AAC AAA CAC ATG AAT GCA GAC         624
Leu Thr Phe Leu Val Asp Leu Ile Lys Asn Lys His Met Asn Ala Asp
        195                     200                     205

ACC GAT TAC TCC ATC GCA GAA GCT GCC TTT AAT AAA GGC GAA ACA GCG         672
Thr Asp Tyr Ser Ile Ala Glu Ala Ala Phe Asn Lys Gly Glu Thr Ala
        210                     215                     220

ATG ACC ATC AAC GGC CCG TGG GCA TGG TCC AAC ATC GAC ACC AGC AAA         720
Met Thr Ile Asn Gly Pro Trp Ala Trp Ser Asn Ile Asp Thr Ser Lys
225                     230                     235                 240

GTG AAT TAT GGT GTA ACG GTA CTG CCG ACC TTC AAG GGT CAA CCA TCC         768
Val Asn Tyr Gly Val Thr Val Leu Pro Thr Phe Lys Gly Gln Pro Ser
                        245                     250                     255

AAA CCG TTC GTT GGC GTG CTG AGC GCA GGT ATT AAC GCC GCC AGT CCG         816
Lys Pro Phe Val Gly Val Leu Ser Ala Gly Ile Asn Ala Ala Ser Pro
                260                     265                     270

AAC AAA GAG CTG GCA AAA GAG TTC CTC GAA AAC TAT CTG CTG ACT GAT         864
Asn Lys Glu Leu Ala Lys Glu Phe Leu Glu Asn Tyr Leu Leu Thr Asp
            275                     280                     285

GAA GGT CTG GAA GCG GTT AAT AAA GAC AAA CCG CTG GGT GCC GTA GCG         912
Glu Gly Leu Glu Ala Val Asn Lys Asp Lys Pro Leu Gly Ala Val Ala
        290                     295                     300

CTG AAG TCT TAC GAG GAA GAG TTG GCG AAA GAT CCA CGT ATT GCC GCC         960
Leu Lys Ser Tyr Glu Glu Glu Leu Ala Lys Asp Pro Arg Ile Ala Ala
305                     310                     315                 320

ACC ATG GAA AAC GCC CAG AAA GGT GAA ATC ATG CCG AAC ATC CCG CAG        1008
Thr Met Glu Asn Ala Gln Lys Gly Glu Ile Met Pro Asn Ile Pro Gln
                        325                     330                     335

ATG TCC GCT TTC TGG TAT GCC GTG CGT ACT GCG GTG ATC AAC GCC GCC        1056
Met Ser Ala Phe Trp Tyr Ala Val Arg Thr Ala Val Ile Asn Ala Ala
                        340                     345                     350

AGC GGT CGT CAG ACT GTC GAT GAA GCC CTG AAA GAC GCG CAG ACT AAT        1104
Ser Gly Arg Gln Thr Val Asp Glu Ala Leu Lys Asp Ala Gln Thr Asn
            355                     360                     365

TCG AGC TCG AAC AAC AAC AAC AAT AAC AAT AAC AAC AAC CTC GGG ATC        1152
Ser Ser Ser Asn Asn Asn Asn Asn Asn Asn Asn Asn Asn Leu Gly Ile
        370                     375                     380

GAG GGA AGG ATT TCA GAA TTC GGA TCC GCC CCG GAA TTC CGG GAG TTT        1200
Glu Gly Arg Ile Ser Glu Phe Gly Ser Ala Pro Glu Phe Arg Glu Phe
385                     390                     395                 400

ACG ATA GAC TTT TCG ACC CAA CAA AGT TAT GTC TCT TCG TTA AAT AGT        1248
Thr Ile Asp Phe Ser Thr Gln Gln Ser Tyr Val Ser Ser Leu Asn Ser
                        405                     410                     415

ATA CGG ACA GAG ATA TCG ACC CCT CTT GAA CAT ATA TCT CAG GGG ACC        1296
```

```
Ile Arg Thr Glu Ile Ser Thr Pro Leu Glu His Ile Ser Gln Gly Thr
        420                 425                 430

ACA TCG GTG TCT GTT ATT AAC CAC ACC CCA CCG GGC AGT TAT TTT GCT           1344
Thr Ser Val Ser Val Ile Asn His Thr Pro Pro Gly Ser Tyr Phe Ala
            435                 440                 445

GTG GAT ATA CGA GGG CTT GAT GTC TAT CAG GCG CGT TTT GAC CAT CTT           1392
Val Asp Ile Arg Gly Leu Asp Val Tyr Gln Ala Arg Phe Asp His Leu
450                 455                 460

CGT CTG ATT ATT GAG CAA AAT AAT TTA TAT GTG GCC GGG TTC GTT AAT           1440
Arg Leu Ile Ile Glu Gln Asn Asn Leu Tyr Val Ala Gly Phe Val Asn
465                 470                 475                 480

ACG GCA ACA AAT ACT TTC TAC CGT TTT TCA GAT TTT ACA CAT ATA TCA           1488
Thr Ala Thr Asn Thr Phe Tyr Arg Phe Ser Asp Phe Thr His Ile Ser
                485                 490                 495

GTG CCC GGT GTG ACA ACG GTT TCC ATG ACA ACG GAC AGC AGT TAT ACC           1536
Val Pro Gly Val Thr Thr Val Ser Met Thr Thr Asp Ser Ser Tyr Thr
            500                 505                 510

ACT CTG CAA CGT GTC GCA GCG CTG GAA CGT TCC GGA ATG CAA ATC AGT           1584
Thr Leu Gln Arg Val Ala Ala Leu Glu Arg Ser Gly Met Gln Ile Ser
            515                 520                 525

CGT CAC TCA CTG GTT TCA TCA TAT CTG GCG TTA ATG GAG TTC AGT GGT           1632
Arg His Ser Leu Val Ser Ser Tyr Leu Ala Leu Met Glu Phe Ser Gly
530                 535                 540

AAT ACA ATG ACC AGA GAT GCA TCC AGA GCA GTT CTG CGT TTT GTC ACT           1680
Asn Thr Met Thr Arg Asp Ala Ser Arg Ala Val Leu Arg Phe Val Thr
545                 550                 555                 560

GTC ACA GCA GAA GCC TTA CGC TTC AGG CAG ATA CAG AGA GAA TTT CGT           1728
Val Thr Ala Glu Ala Leu Arg Phe Arg Gln Ile Gln Arg Glu Phe Arg
                565                 570                 575

CAG GCA CTG TCT GAA ACT GCT CCT GTG TAT ACG ATG ACG CCG GGA GAC           1776
Gln Ala Leu Ser Glu Thr Ala Pro Val Tyr Thr Met Thr Pro Gly Asp
            580                 585                 590

GTG GAC CTC ACT CTG AAC TGG GGG CGA ATC AGC AAT GTG CTT CCG GAG           1824
Val Asp Leu Thr Leu Asn Trp Gly Arg Ile Ser Asn Val Leu Pro Glu
            595                 600                 605

TAT CGG GGA GAG GAT GGT GTC AGA GTG GGG AGA ATA TCC TTT AAT AAT           1872
Tyr Arg Gly Glu Asp Gly Val Arg Val Gly Arg Ile Ser Phe Asn Asn
610                 615                 620

ATA TCA GCG ATA CTG GGG ACT GTG GCC GTT ATA CTG AAT TGC CAT CAT           1920
Ile Ser Ala Ile Leu Gly Thr Val Ala Val Ile Leu Asn Cys His His
625                 630                 635                 640

CAG GGG GCG CGT TCT GTT CGC GCC GTG AAT GAA GAG AGT CAA CCA GAA           1968
Gln Gly Ala Arg Ser Val Arg Ala Val Asn Glu Glu Ser Gln Pro Glu
                645                 650                 655

TGT CAG ATA ACT GGC GAC AGG CCT GTT ATA AAA ATA AAC AAT ACA TTA           2016
Cys Gln Ile Thr Gly Asp Arg Pro Val Ile Lys Ile Asn Asn Thr Leu
            660                 665                 670

TGG GAA AGT AAT ACA GCT GCA GCG TTT CTG AAC AGA AAG TCA CAG TTT           2064
Trp Glu Ser Asn Thr Ala Ala Ala Phe Leu Asn Arg Lys Ser Gln Phe
            675                 680                 685

TTA TAT ACA ACG GGT AAA TAA                                               2085
Leu Tyr Thr Thr Gly Lys
        690

(2) INFORMATION FOR SEQ ID NO:49:

(i) SEQUENCE CHARACTERISTICS:
        (A) LENGTH: 694 amino acids
        (B) TYPE: amino acid
        (D) TOPOLOGY: linear
```

(ii) MOLECULE TYPE: protein (xi) SEQUENCE DESCRIPTION: SEQ ID NO:49:

| Met | Lys | Ile | Glu | Glu | Gly | Lys | Leu | Val | Ile | Trp | Ile | Asn | Gly | Asp | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Gly Ser Ala Pro Glu Phe Arg Glu Phe
385                 390                 395                 400

-continued

```
Thr Ile Asp Phe Ser Thr Gln Gln Ser Tyr Val Ser Ser Leu Asn Ser
            405                 410                 415

Ile Arg Thr Glu Ile Ser Thr Pro Leu Glu His Ile Ser Gln Gly Thr
            420                 425                 430

Thr Ser Val Ser Val Ile Asn His Thr Pro Pro Gly Ser Tyr Phe Ala
            435                 440                 445

Val Asp Ile Arg Gly Leu Asp Val Tyr Gln Ala Arg Phe Asp His Leu
    450                 455                 460

Arg Leu Ile Ile Glu Gln Asn Asn Leu Tyr Val Ala Gly Phe Val Asn
465                 470                 475                 480

Thr Ala Thr Asn Thr Phe Tyr Arg Phe Ser Asp Phe Thr His Ile Ser
            485                 490                 495

Val Pro Gly Val Thr Thr Val Ser Met Thr Thr Asp Ser Ser Tyr Thr
            500                 505                 510

Thr Leu Gln Arg Val Ala Ala Leu Glu Arg Ser Gly Met Gln Ile Ser
            515                 520                 525

Arg His Ser Leu Val Ser Ser Tyr Leu Ala Leu Met Glu Phe Ser Gly
    530                 535                 540

Asn Thr Met Thr Arg Asp Ala Ser Arg Ala Val Leu Arg Phe Val Thr
545                 550                 555                 560

Val Thr Ala Glu Ala Leu Arg Phe Arg Gln Ile Gln Arg Glu Phe Arg
            565                 570                 575

Gln Ala Leu Ser Glu Thr Ala Pro Val Tyr Thr Met Thr Pro Gly Asp
            580                 585                 590

Val Asp Leu Thr Leu Asn Trp Gly Arg Ile Ser Asn Val Leu Pro Glu
            595                 600                 605

Tyr Arg Gly Glu Asp Gly Val Arg Val Gly Arg Ile Ser Phe Asn Asn
            610                 615                 620

Ile Ser Ala Ile Leu Gly Thr Val Ala Val Ile Leu Asn Cys His His
625                 630                 635                 640

Gln Gly Ala Arg Ser Val Arg Ala Val Asn Glu Glu Ser Gln Pro Glu
            645                 650                 655

Cys Gln Ile Thr Gly Asp Arg Pro Val Ile Lys Ile Asn Asn Thr Leu
            660                 665                 670

Trp Glu Ser Asn Thr Ala Ala Ala Phe Leu Asn Arg Lys Ser Gln Phe
            675                 680                 685

Leu Tyr Thr Thr Gly Lys
    690
```

COMPOSITIONS FOR THE PREVENTION AND TREATMENT OF VEROTOXIN-INDUCED DISEASE

This is a Continuation-In-Part of application Ser. No. 08/410,058 filed Mar. 24, 1995 now abandoned.

FIELD OF THE INVENTION

The present invention relates to antitoxin therapy and prevention of disease due to *Escherichia coli* verotoxin in humans and other animals, and diagnostic assays to detect toxins. In particular, the present invention relates to the isolation of polypeptides derived from *Escherichia coli* verotoxins, and the use thereof as immunogens for the production of vaccines, including multivalent vaccines, and antitoxins.

BACKGROUND OF THE INVENTION

A. *Escherichia coli* as a Pathogenic Organism *Escherichia coli* is the organism most commonly isolated in clinical microbiology laboratories, as it is usually present as normal flora in the intestines of humans and other animals. However, it is an important cause of intestinal, as well as extraintestinal infections. For example, in a 1984 survey of nosocomial infections in the United States, *E. coli* was associated with 30.7% of the urinary tract infections, 11.5% of the surgical wound infections, 6.4% of the lower respiratory tract infections, 10.5% of the primary bacteremia cases, 7.0% of the cutaneous infections, and 7.4% of the other infections (J. J. Farmer and M. T. Kelly, "Enterobacteriaceae," in *Manual of Clinical Microbiology,* Balows et al.(eds), American Society for Microbiology, [1991], p. 365). Surveillance reports from England, Wales and Ireland for 1986 indicate that *E. coli* was responsible for 5,473 cases of bacteremia (including blood, bone marrow, spleen and heart specimens); of these, 568 were fatal. For spinal fluid specimens, there were 58 cases, with 10 fatalities (J. J. Farmer and M. T. Kelly, "Enterobacteriaceae," in *Manual of Clinical Microbiology,* Balows et al.(eds), American Society for Microbiology, [1991], p. 366). There are no similar data for United States, as these are not reportable diseases in this country.

Studies in various countries have identified certain serotypes (based on both the O and H antigens) that are associated with the four major groups of *E. coli* recognized as enteric pathogens. Table 1 lists common serotypes included within these groups. The first group includes the classical enteropathogenic serotypes ("EPEC"); the next group includes those that produce heat-labile or heat-stable enterotoxins ("ETEC"); the third group includes the enteroinvasive strains ("EIEC") that mimic Shigella strains in their ability to invade and multiply within intestinal epithelial cells; and the fourth group includes strains and serotypes that cause hemorrhagic colitis or produce Shiga-like toxins (or verotoxins) ("VTEC" or "EHEC" [enterohemmorrhagic *E. coli*]).

TABLE 1

Pathogenic *E. coli* Serotypes

| Group | Associated Serotypes |
|---|---|
| Enterotoxigenic (ETEC) | O6:H16; O8:NM; O8:H9; O11:H27; O15:H11; O20:NM; O25:NM; O25:H42; O27:H7; O27:H20; O63:H12; O78:H11; O78:H12; O85:H7; O114:H21; O115:H21; O126:H9; O128ac:H7; O128ac:H12; O128ac:H21; O148:H28; O149:H4; O159:H4; O159:H20; O166:H27; and O167:H5 |
| Enteropathogenic (EPEC) | O26:NM; O26:HI1; O55:NM; O55:H6; O86:NM; O86:H2; O86:H34; O111ab:NM; O111ab:H2; O111ab:H12; O111ab:H21; O114:H2; O119:H6; O125ac:H21; O127:NM; O127:H6; O127:H9; O127:H21; O128ab:H2; O142:H6; and O158:1123 |
| Enteroinvasive (EIEC) | O28ac:NM; O29:NM; O112ac:NM; O115:NM; O124:NM; O124:H7; O124:H30; O135:NM; O136:NM; O143:NM; O144:NM; O152:NM; O164:NM; and O167:NM |
| Verotoxin-Producing (VTEC)) | O1:NM; O2:H5; O2:H7; O4:NM; O4:H10; O5:NM; O5:H16; O6:H1; O18:NM; O18:H7; O25:NM; O26:NM; O26:H11; O26:H32; O38:H21; O39:H4; O45:H2; O50:H7; O55:H7; O55:H10; O82:H8; O84:H2; O91:NM; O91:H21; O103:H2; O111:NM; O111:H8; O111:H30; O111:H34; O113:H7; O113:H21; O114:H48; O115:H10; O117:H4; O118:H12; O118:H30; O121:NM; O121:H19; O125:NM; O125:H8; O126:NM; O126:H8; O128:NM; O128:H2; O128:H8; O128:H12; O128:H25; O145:NM; O125:H25; O146:H21; O153:H25; O157:NM; O157:H7; O163:H19; O165:NM; O165:19; and O165:H25 |

B. Verotoxin Producing Strains of *E. coli*

Although all of these disease-associated serotypes cause potentially life-threatening disease, *E. coli* O157:H7 and other verotoxin-producing strains have recently gained widespread public attention in the United States due to their recently recognized association with two serious extraintestinal diseases, hemolytic uremic syndrome ("HUS") and thrombotic thrombocytopenic purpura ("TTP"). Worldwide, *E. coli* O157:H7 and other verotoxin-producing *E. coli* (VTEC) are an increasingly important human health problem. First identified as a cause of human illness in early 1982 following two outbreaks of food-related hemorrhagic colitis in Oregon and Michigan (M. A. Karmali, "Infection by Verocytotoxin-Producing *Escherichia coli,* " Clin. Microbiol. Rev., 2:15–38 [1989]; and L. W. Riley, et al. "Hemorrhagic colitis associated with a rare *Escherichia coli* serotype," New Eng. J. Med., 308: 681–685 [1983]), the reported incidence of VTEC-associated disease has risen steadily, with outbreaks occurring in the U.S., Canada, and Europe.

With increased surveillance, *E. coli* O157:H7 has been recognized in other areas of the world including Mexico, China, Argentina, Belgium, and Thailand (N. V. Padhye and M. P. Doyle, "*Escherichia coli* O157:H7: Epidemiology, pathogenesis and methods for detection in food," J. Food. Prot., 55: 555–565 [1992]; and P. M. Griffin and R. V. Tauxe, "The epidemiology of infections caused by *Escherichia coli* O157:H7, other enterohemorrhagic *E. coli,* and the associated hemolytic uremic syndrome," Epidemiol. Rev., 13: 60 [1991]).

The disease attracted national attention in the U.S. after a major outbreak in the Pacific Northwest that was associated with consumption of undercooked *E. coli* O157:H7-contaminated hamburgers. Over 700 hundred people fell ill (more than 170 were hospitalized) and four young children died (P. Recer, "Experts call for irradiation of meat to protect against food-borne bacteria," Associated Press, Jul. 12, 1994 [1994]). Several outbreaks since then have underscored the potential severity and multiple mechanisms for transmission of VTEC-associated diseases (M. Bielaszewská et al., "Verotoxigenic (enterohaemorrhagic) *Escherichia coli* in infants and toddlers in Czechoslovakia," Infection 18: 352–356 [1990]; A. Caprioli et al., "Hemolytic-uremic syndrome and Vero cytotoxin-producing *Escherichia coli* infection in Italy," J. Infect. Dis., 166: 184–158 [1992]; A. Caprioli, et al., "Community-wide Outbreak of Hemolytic-Uremic Syndrome Associated with Non-O157 Verocytotoxin-Producing *Escherichia coli,*" J. Infect. Dis., 169: 208–211 [1994]; N. Cimolai, "Low frequency of high level Shiga-like toxin production in enteropathogenic *Escherichia coli* serogroups," Eur. J. Pediatr., 151: 147 [1992]; and R. Voelker., "Panel calls *E. coli* screening inadequate," *Escherichia coli* O157:H7—Panel sponsored by the American Gastroenterological Association Foundation in July 1994, Medical News & Perspectives, J. Amer. Med. Assoc., 272: 501 [1994]).

While O157:H7 is currently the predominant *E. coli* serotype associated with illness in North America, other serotypes (as shown in Table 1, and in particular O26:H11, O113:H21, O91:H21 and O111:NM) also produce verotoxins which appear to be important in the pathogenesis of gastrointestinal manifestations and the hemolytic uremic syndrome (P. M. Griffin and R. V. Tauxe, "The epidemiology of infections caused by *Escherichia coli* O157:H7, other enterohemorrhagic *E. coli,* and the associated hemolytic uremic syndrome," Epidemiol. Rev., 13: 60 [1991]; M. M. Levine, et al., "Antibodies to Shiga holotoxin and to two synthetic peptides of the B subunit in sera of patients with *Shigella dysenteriae* 1 dysentery," J. Clin. Microbiol., 30: 1636–1641 [1992]; and C. R. Dorn, et al., "Properties of Vero cytotoxin producing *Escherichia coli* of human and animal origin belonging to serotypes other than O157:H7," Epidemiol. Infect., 103: 83–95 [1989]). Since organisms with these serotypes have been shown to cause illness in humans they may assume greater public health importance over time (P. M. Griffin and R. V. Tauxe, "The epidemiology of infections caused by *Escherichia coli* O157:H7, other enterohemorrhagic *E. coli,* and the associated hemolytic uremic syndrome," Epidemiol. Rev., 13: 60 [1991]).

Clinicians usually observe cases of hemolytic uremic syndrome ("HUS") clustered in a geographic region. However, small outbreaks are likely to be missed because many laboratories do not routinely screen stool specimens for *E. coli* O157:H7. Many cases related to non-commercial food preparation also probably go unrecognized. Nonetheless, *E. coli* O157:H7 is responsible for a large number of cases, as more than 20,000 cases of *E. coli* O157:H7 infection are reported annually in the U.S., with 400–500 deaths from HUS. However, these estimates were compiled when only 11 states mandated reporting of *E. coli* O157:H7. Twenty-nine states have recently made *E. coli* O157:H7 infection a reportable disease (R. Voelker, "Panel calls *E. coli* screening inadequate; *Escherichia coli* O157:H7; panel sponsored by the American Gastroenterological Association Foundation in July 1994, Medical News & Perspectives," J. Amer. Med. Assoc., 272: 501 [1994]). Indeed, the Centers for Disease Control recently added *E. coli* O157:H7 to their list of reportable diseases ("Public Health Threats," Science 267:1427 [1995]).

C. Nature of Verotoxin-Induced Disease

Risk factors for HUS progression following infection with *E. coli* O157:H7 include age (very young or elderly), bloody diarrhea, leukocytosis, fever, large amounts of ingested pathogen, previous gastrectomy, and the use of antimicrobial agents (in particular, trimethoprim-sulfamethoxazole)(A. A. Harris et al., "Results of a screening method used in a 12 month stool survey for *Escherichia coli* O157:H7," J. Infect. Dis., 152: 775–777 [1985]; and M. A. Karmali, "Infection by Verocytotoxin-producing *Escherichia coli,*" Clin. Microbiol. Rev., 2: 15–38 [1989]).

As indicated above, *E. coli* O157:H7 is associated with significant morbidity and mortality. The spectrum of illness associated with *E. coli* O157:H7 infection includes asymptomatic infection, mild uncomplicated diarrhea, hemorrhagic colitis, HUS, and TTP". Hemorrhagic colitis (or "ischemic colitis") is a distinct clinical syndrome characterized by sudden onset of abdominal cramps—likened to the pain associated with labor or appendicitis—followed within 24 hours by watery diarrhea. One to two days later, the diarrhea turns grossly bloody in approximately 90% of patients and has been described as "all blood and no stool" (C. H. Pai et al., "Sporadic cases of hemorrhagic colitis associated with *Escherichia coli* O157:H7," Ann. Intern. Med., 101: 738–742 [1984]; and R. S. Remis et al., "Sporadic cases of hemorrhagic colitis associated with *Escherichia coli* O157:H7," Ann. Intern. Med., 101: 738–742 [1984]). Vomiting may occur, but there is little or no fever. The time from ingestion to first loose stool ranges from 3–9 days (with a mean of 4 days) L. W. Riley et al., "Hemorrhagic colitis associated with a rare *Escherichia coli* serotype," New Eng. J. Med., 308: 681–685 [1983]; and D. Pudden et al., "Hemorrhagic colitis in a nursing home," Ontario Can. Dis. Weekly Rpt., 11: 169–170 [1985]), and the duration of illness ranges generally from 2–9 days (with a mean of 4 days).

HUS is a life-threatening blood disorder that appears within 3–7 days following onset of diarrhea in 10–15% of patients. Those younger than 10 years and the elderly are at particular risk. Symptoms include renal glomerular damage, hemolytic anemia (rupturing of erythrocytes as they pass through damaged renal glomeruli), thrombocytopenia and acute kidney failure. Approximately 15% of patients with HUS die or suffer chronic renal failure. Indeed, HUS is a leading cause of renal failure in childhood (reviewed by M. A. Karmali, "Infection by Verocytotoxin-producing *Escherichia coli,*" Clin. Microbiol. Rev., 2: 15–38 [1989]). Currently, blood transfusion and dialysis are the only therapies for HUS.

TTP shares similar histopathologic findings with HUS, but usually results in multiorgan microvascular thrombosis. Neurological signs and fever are more prominent in TTP, compared with HUS. Generally occurring in adults, TTP is characterized by microangiopathic hemolytic anemia, pro-found thrombocytopenia, fluctuating neurologic signs, fever and mild azotemia (H. C. Kwaan, "Clinicopathological features of thrombotic thrombocytopenic purpura," Semin. Hematol., 24: 71–81 [1987]; and S. J. Machin, "Clinical annotation: Thrombotic thrombocytopenic purpura," Br. J. Hematol., 56: 191–197 [1984]). Patients often die from microthrombi in the brain. In one review of 271 cases, a rapidly progressive course was noted, with 75% of patients dying within 90 days (E. L. Amorosi and J. E. Ultmann, "Thrombotic thrombocytopenic purpura: Report of 16 cases and review of the literature," Med., 45:139–159 (1966).

Other diseases associated with E. coli O157:H7 infection include hemorrhagic cystitis and balantitis (W. R. Grandsen et al., "Hemorrhagic cystitis and balantitis associated with verotoxin-producing Escherichia coli O157:H7," Lancet ii: 150 [1985]), convulsions, sepsis with other organisms and anemia (P. C. Rowe et al., "Hemolytic anemia after childhood Escherichia coli O157:H7 infection: Are females at increased risk?" Epidemiol. Infect., 106: 523–530 [1991]).

D. Mechanism of Pathogenesis

Verotoxins are strongly linked to E. coli O157:H7 pathogenesis. All clinical isolates of E. coli O157:H7 have been shown to produce one or both verotoxins (VT1 and VT2) (C. A. Bopp et al., "Unusual Verotoxin-producing Escherichia coli associated with hemorrhagic colitis," J. Clin. Microbiol., 25: 1486–1489 [1987]). The VT1 and VT2 genes are carried by temperate coliphages 933J and 933W, respectively. Once lysogenized, these coliphages lead to the expression of toxin genes by the E. coli host.

Both of these toxins are cytotoxic to Vero (African green monkey kidney) and HeLa cells, and cause paralysis and death in mice (A. D. O'Brien et al., "Purification of Shigella dysenteriae 1 (Shiga) like toxin from Escherichia coli O157:H7 strain associated with hemorrhagic colitis," Lancet ii: 573 [1983]). These toxins are sometimes referred to in the literature as Shiga-like toxins I and II (SLT-I and SLT-II, respectively), due to their similarities with the toxins produced by Shigella. Indeed, much of our understanding of E. coli VTs is based on information accumulated on Shiga toxins. Shiga toxin, first described in 1903, has been recognized as one of the most potent bacterial toxins for eukaryotic cells (reviewed by M. A. Karmali, "Infection by Verocytotoxin-producing Escherichia coli," Clin. Microbiol. Rev., 2: 15–38 [1989]). Hereinafter, the VT convention will be used; thus, VT1 and VT2 correspond to SLT-I and SLT-II, respectively.

While the pathogenic mechanism of E. coli O157:H7 infection is incompletely understood, it is believed that ingested organisms adhere to and colonize the intestinal mucosa, where toxins are released which cause endothelial cell damage and bloody diarrhea. It is also postulated that hemorrhagic colitis progresses to HUS when verotoxins enter the bloodstream, damaging the endothelial cells of the microvasculature and triggering a cascade of events resulting in thrombus deposition in small vessels. These microthrombi occlude the microcapillaries of the kidneys (particularly in the glomeruli) and other organs, resulting in their failure (J. J. Byrnes and J. L. Moake, "TTP and HUS syndrome: Evolving concepts of pathogenesis and therapy," Clin. Hematol., 15: 413–442 [1986]; and T. G. Cleary, "Cytotoxin-producing Escherichia coli and the hemolytic uremic syndrome," Pediatr. Clin. North Am., 35: 485–501 [1988]). Verotoxins entering the bloodstream may also result in direct kidney cytotoxicity.

VT1 is immunologically and structurally indistinguishable from Shiga toxin produced by Shigella dysenteriae (A. D. O'Brien et al., "Purification of Shigella dysenteriae 1 (Shiga) like toxin from Escherichia coli O157:H7 strain associated with hemorrhagic colitis," Lancet ii: 573 [1983]). VT1 and VT2 holotoxins each consist of one A and five B subunits (A. Donohue-Rolfe et al., "Purification of Shiga toxin and Shiga-like toxins I and II by receptor analog affinity chromatography with immobilized P1 glycoprotein and production of cross reactive monoclonal antibodies," Infect. Immun., 57: 3888–3893 [1989]; and A. Donohue-Rolfe et al., "Simplified high yield purification of Shigella toxin and characterization of subunit composition and function by the use of subunit-specific monoclonal and polyclonal antibodies," J. Exp. Med., 160: 1767–1781 [1984]). Intra-chain disulfide bonds are formed and the holotoxin is assembled after secretion of the subunits to the periplasm. Each subunit contains a leader sequence that targets secretion of the toxin. VT1 and VT2 are structurally related, sharing 56% amino acid homology.

The toxic A subunit is enzymatically active, while the B subunit binds the holotoxin to the receptor on the target eukaryotic cell. The A chain is structurally related to the ricin A chain, and acts in a similar manner to inhibit protein synthesis by cleaving a single adenine residue from 28S ribosomal RNA (Endo et al., J. Biol. Chem., 262:5908–5912 [1987]). The A chain is 32 (VT1) or 33 (VT2) kd in size, and is proteolytically cleaved into A1 (approximately 27 kd) and A2 (approximately 3–4 kd) fragments. In both VT1 and VT2, the non-toxic B subunit is approximately 8 kd. Pentamers of the B subunit bind mammalian cell surface receptors, facilitating internalization of holotoxin by cells.

Crystal structure analysis of Shiga holotoxin and VT1 B subunit pentamers have shown that the holotoxin assembles with the C-terminal end of the A subunit associating with, and inserting within, a pentamer of B chains (P. E. Stein et al., "Crystal structure of the cell-binding B oligomer of verotoxin-1 from E. coli," Nature 355: 748–750 [1992]; and M. E. Fraser et al., "Crystal structure of the holotoxin from Shigella dysenteriae at 2.5 Å resolution," Struct. Biol., 1:59–64 [1994]). The alpha helical C-terminal region of the A chain (residues 279–293) is encircled by a pentameric ring of B subunits, with the remainder of the A chain exposed. This conformation is consistent with the observation that a C-terminally truncated A1 subunit of VT1 is toxic (in a ribosomal inhibition assay), but cannot associate with B subunit pentamers (P. R. Austin et al, "Evidence that the $A_2$ fragment of Shiga-like toxin type I is required for holotoxin integrity," Infect. Immun., 62: 1768 [1994]).

The Verotoxin A Subunit.

Examination of the crystal structure of Shiga holotoxin indicates that the N-terminus of its A subunit is both surface-exposed and functionally important. Removal of amino acid interval 3–18 of the A subunit completely abolished toxicity (L. P. Perera et al., "Mapping the minimal contiguous gene segment that encodes functionally active Shiga-like toxin II," Infect. Immun., 59: 829–835 [1991]) while removal of interval 25–44 retained toxicity but abolished its association with B subunit pentamers (J. E. Haddad et al., "Minimum domain of the Shiga toxin A subunit required for enzymatic activity," J. Bacteriol., 175: 4970–4978 [1993]). Deletion of the first 13 residues of the homologous ricin A subunit also abolished toxicity, while deletion of the first 9 residues did not (M. J. May, et al., "Ribosome inactivation by ricin A chain: A sensitive method to assess the activity of wild-type and mutant polypeptides," EMBO J., 8: 301–308 [1989]).

The Verotoxin B Subunit.

Studies of Shiga toxin B subunit suggest that neutralizing epitopes may also be present at both the N- and C-terminal regions of VT1 and VT-2 B subunits. Polyclonal antibodies raised against peptides from these regions (residues 5–18, 13–26, 7–26, 54–67 and 57–67) show partial neutralization of Shiga toxin (I. Harari and R. Arnon, "Carboxy-terminal peptides from the B subunit of Shiga toxin induce a local and parenteral protective effect," Mol. Immunol., 27: 613–621 [1990]; and I. Harari et al., "Synthetic peptides of Shiga toxin B subunit induce antibodies which neutralize its biological activity," Infect. Immun., 56: 1618–1624 [1988]). Deletion of the last five amino acids of Shiga toxin B (M. P. Jackson et al., "Functional Analysis of the Shiga toxin and Shiga-like toxin Type II variant binding subunits by using site-directed mutagenesis," J. Bacteriol., 172: 653–658 [1990]), or four amino acids of VT2 B (L. P. Perera et al., "Mapping the minimal contiguous gene segment that encodes functionally active Shiga-like toxin II," Infect. Immun., 59: 829–835 [1991]), eliminate toxin activity, while deletion of the last two amino acids of VT2 B subunit reduced cytotoxicity. In contrast, the addition of an 18 or 21 amino acid extension to the native C-termiinus of the VT2 B subunit was presumably conformationally correct, as these proteins assembled cytotoxic holotoxin.

Various approaches to express recombinant verotoxins have included individual or coordinate expression of A and B subunits from high-copy number plasmids and expression with fusion partners (J. E. Haddad et al., "Minimum domain of the Shiga toxin A subunit required for enzymatic activity," J. Bacteriol., 175: 4970–4978 ; J. E. Haddad, and M. P. Jackson, "Identification of the Shiga toxin A-subunit residues required for holotoxin assembly," J. Bacteriol., 175: 7652–7657 [1993]; M. P. Jackson et al., "Mutational analysis of the Shiga toxin and Shiga-like toxin II enzymatic subunits," J. Bacteriol., 172: 3346–3350 [1990]; C. J. Hovde et al., "Evidence that glutamic acid 167 is an active-site residue of Shiga-like toxin I," Proc. Natl. Acad. Sci., 85: 2568–2572 [1988]; R. L. Deresiewicz et al., "The role of tyrosine-114 in the enzymatic activity of the Shiga-like toxin I A-chain," Mol. Gen. Genet., 241: 467–473 [1993]; T. M. Zollman et al., "Purification of Recombinant Shiga-like Toxin Type I $A_1$ Fragment from *Escherichia coli*," Protein Express. Purific., 5: 291–295 [1994]; K. Ramotar, et al., "Characterization of Shiga-like toxin I B subunit purified from overproducing clones of the SLT-I B cistron," Biochem J., 272: 805–811 [1990]; S. B. Calderwood et al., "A system for production and rapid purification of large amounts of the Shiga toxin/Shiga-like toxin I B subunit," Infect. Immun., 58: 2977–2982 [1990]; D. W. K. Acheson, et al., "Comparison of Shiga-like toxin I B-subunit expression and localization in *Escherichia coli* and *Vibrio cholerae* by using trc or iron-regulated promoter systems," Infect. Immun. 61: 1098–1104 [1993]; M. P. Jackson et al., "Nucleotide sequence analysis and comparison of the structural genes for Shiga-like toxin I and Shiga-like toxin II encoded by bacteriophages from *Escherichia coli* 933," FEMS Microbiol. Lett., 44: 109–114 [1987]; J. W. Newland et al., "Cloning of genes for production of *Escherichia coli* Shiga-like toxin type II," Infect. Immun. 55: 2675–2680 [1987]; and F. Gunzer and H. Karch, "Expression of A and B subunits of Shiga-like toxin II as fusions with glutathione S-transferase and their potential for use in seroepidemiology," J. Clin. Microbiol., 31: 2604–2610 [1993]; and D. W. Acheson et al., "Expression and purification of Shiga-like toxin II B subunits," Infect. Immun., 63:301–308 [1995]). In one case, bench top fermentation techniques yielded 22 mg/liter of soluble recombinant protein (D. W. K. Acheson, et al., "Comparison of Shiga-like toxin I B-subunit expression and localization in *Escherichia coli* and *Vibrio cholerae* by using trc or Iron-regulated promoter systems," Infect. Immun. 61: 1098– 1104 [1993]). However, there have been no systematic approaches to identifying the appropriate spectrum of VT antigens, preserving immunogen and immunoabsorbant antigenicity and scaling-up.

The receptor for VT1 and VT2 is a globotriaosyl ceramide containing a galactose α-(1-4)-galactose-β-(1-4) glucose ceramide (Gb3) (C. A. Lingwood et al., "Glycolipid binding of natural and recombinant *Escherichia coli* produced verotoxin in vitro," J. Biol. Chem., 262: 1779–1785 [1987]; and T. Wadell et al., "Globotriaosyl ceramide is specifically recognized by the *Escherichia coli* verocytotoxin 2," Biochem. Biophys. Res. Commun., 152: 674–679 [1987]). Gb3 is abundant in the cortex of the human kidney and is present in primary human endothelial cell cultures. Hence, the identification of Gb3 as the functional receptor for VT1 and VT2 is consistent with their role in HUS pathogenesis, in which endothelial cells of the renal vasculature are the principal site of damage. Therefore, toxin-mediated pathogenesis may follow a sequence of B subunit binding to Gb3 receptors on kidney cells, toxin internalization, enzymatic reduction of the A subunit to an A1 fragment, binding of the A1 subunit to the 60S ribosomal subunit, inhibition of protein synthesis and cell death (A. D. O'Brien et al., "Shiga and Shiga-like toxins. Microbial Rev., 51: 206–220 [1987]).

The role of verotoxins in the pathogenesis of *E. coli* O157:H7 infections has been further studied in animal models. Infection or toxin challenge of laboratory animals do not produce all the pathologies and symptoms of hemorrhagic colitis, HUS, and TTP which occur in humans. Glomerular damage is noticeably absent. Nonetheless, experiments using animal models implicate verotoxins as the direct cause of hemorrhagic colitis, microvascular damage leading to the failure of kidneys and other organs and CNS neuropathies.

For example, Barrett, et al. delivered VT2 into the peritoneal cavity of rabbits using mini-osmotic pumps (J. J. Barrett et al., "Continuous peritoneal infusion of shiga-like toxin II (SLTII) as a model for SLT II-induced diseases," J. Infect. Dis., 159: 774–777 [1989]). In three days, most animals receiving the toxin developed diarrhea, with intestinal lesions resembling those seen in humans with hemorrhagic colitis. Although there was some evidence of renal dysfunction, none of the rabbits developed HUS. Beery, et al. showed that VT2, when administered intraperitoneally or intravenously to adult mice, produces lesions of the kidneys and colon (J. T. Beery et al., "Cytotoxic activity of *Escherichia coli* O157:H7 culture filtrate on the mouse colon and kidney," Curr. Microbiol., 11: 335–342 [1984]). Histologic lesions in the kidney included accumulation of numerous exfoliated collecting tubules and marked intracellular vacuolation of proximal convoluted tubular cells.

Sjögren et. al. studied the pathogenesis of an entero-adherent strain of *E. coli* (RDEC-1) lysogenized with a VT1-containing bacteriophage (VT1-producing RDEC-1) (R. Sjögren et al., "Role of Shiga-like toxin I in bacterial enteritis: comparison between isogenic *Escherichia coli* strains induced in rabbits," Gastroenterol., 106: 306–317 [1994]). In this study, rabbits were challenged with RDEC-1 or VT1-producing RDEC-1 and studied for onset of disease. The VT1-producing variant induced a severe, non-invasive, entero-adherent infection in rabbits which was characterized by serious histological lesions with vascular changes, edema and severe epithelial inflammation. Importantly, vascular changes consistent with endothelial damage were seen in infected animals that was similar to intestinal microvascular changes in humans with *E. coli* O157:H7 infection. Based on these observations, they concluded that VT1 is an important virulence factor in enterohemorrhagic *E. coli* O157:H7 infection.

Fuji et. al. described a model in which mice were treated for three days with streptomycin followed by a simultaneous challenge of *E. coli* O157:H7 orally, and mitomycin intraperitoneally (J. Fuji et al., "Direct evidence of neuron impairment by oral infection with Verotoxin-producing *Escherichia coli* O157:H7 in mitomycin-treated mice," Infect. Immun., 62: 3447–34453 [1994]). All of the animals died within four days. Immunoelectron-microscopy strongly suggested that death was due to the toxic effects of VT2v (a structural variant of VT2), on both the endothelial cells and neurons in the central nervous system which resulted in fatal acute encephalopathy.

Wadolkowski et al. studied colonization of *E. coli* O157:H7 in mice. Mice were treated with streptomycin and fed $10^{10}$ *E. coli* O157:H7 (E. A. Wadolkowski et al., "Mouse model for colonization and disease caused by enterohemorrhagic *Escherichia coli* O157:H7," Infect. Immun., 58: 2438–2445 [1990]; and E. A. Wadolkowski et al., "Acute renal tubular necrosis and death of mice orally infected with *Escherichia coli* strains that produce Shiga-like toxin Type II," Infect. Immun., 58: 3959–3965 [1990]). All of the mice died due to severe, disseminated, acute necrosis of proximal convoluted tubules. In mouse models, glomerular damage was not observed, but toxic acute renal tubular necrosis was observed which is characteristic of some HUS patients. The failure of mice to show glomerular damage is thought to be due to the absence of a functional globotriaosyl ceramide receptor specific for verotoxins in the glomeruli of the kidneys. Administration of VT2 subunit-specific monoclonal antibodies prior to infection prevented all pathology and death.

E. Current Therapeutic Approaches

*E. coli* O157:H7 disease is not adequately controlled by current therapy. Patient treatment is tailored to manage fluid and electrolyte disturbances, anemia, renal failure and hypertension. Although *E. coli* O157:H7 is susceptible to common antibiotics, the role of antibiotics in the treatment of infection has questionable merit. In both retrospective and prospective studies, prophylaxis or treatment with antibiotics such as trimethoprim-sulfamethoxazole, there was either no benefit or an increased risk of developing HUS (T. N. Bokete et al., "Shiga-like toxin producing *Escherichia coli* in Seattle children: a prospective study," Gastroenterol., 105: 1724–1731 [1993]; A. T. Pavia et al., "Hemolytic uremic-syndrome during an outbreak of *Escherichia coli* O157:H7 infections in institutions for mentally retarded persons: clinical and epidemiologic observations," J. Pedatr., 116: 544–551 [1990]; F. Proulx et al., "Randomized, controlled trial of antibiotic therapy for *Escherichia coli* O157:H7 enteritis," J. Pediatr. 121: 299–303 [1992]; and A. L. Carter et al., "A severe outbreak of *Escherichia coli* O157:H7-associated hemorrhagic colitis in a nursing home," New Eng. J. Med., 317: 1496–1500 [1987]).

The mechanisms by which antibiotics increase the risk of infection or related complications might involve enhancement of toxin production, release of toxins from killed organisms, or alteration of normal competing intestinal flora allowing for pathogen overgrowth (M. A. Karmali, "Infection by Verocytotoxin-producing *Escherichia coli*," Clin. Microbiol. Rev., 2: 15–38 [1989]). A further concern in the use of antibiotics is the potential acquisition of antimicrobial resistance by *E. coli* O157:H7 (C. R. Dorn, "Review of foodborne outbreak of *Escherichia coli* O157:H7 infection in the western United States," JAVMA 203: 1583–1587 [1993]).

In addition, by the time symptoms are serious enough to attract medical attention, it is likely that verotoxins are already entering the systemic circulation or will do so shortly thereafter. Although antimicrobials may help to prevent pathology resulting from the action of toxin on the bowel lumen. However, by the time symptoms of HUS have developed, the patient has ceased shedding organisms. Thus, antimicrobial treatment during HUS disease is of less value, and often contraindicated, due to the increased risk of complications associated with administration of antimicrobials to patients susceptible to development of HUS. Importantly, there is currently no antitoxin commercially available for use in treating affected patients. What is needed is a means to block the progression of disease, without the complications associated with antimicrobial treatment.

DESCRIPTION OF THE FIGURES

FIG. 1 is an SDS-PAGE of rVT1 and rVT2.

Figure 3:
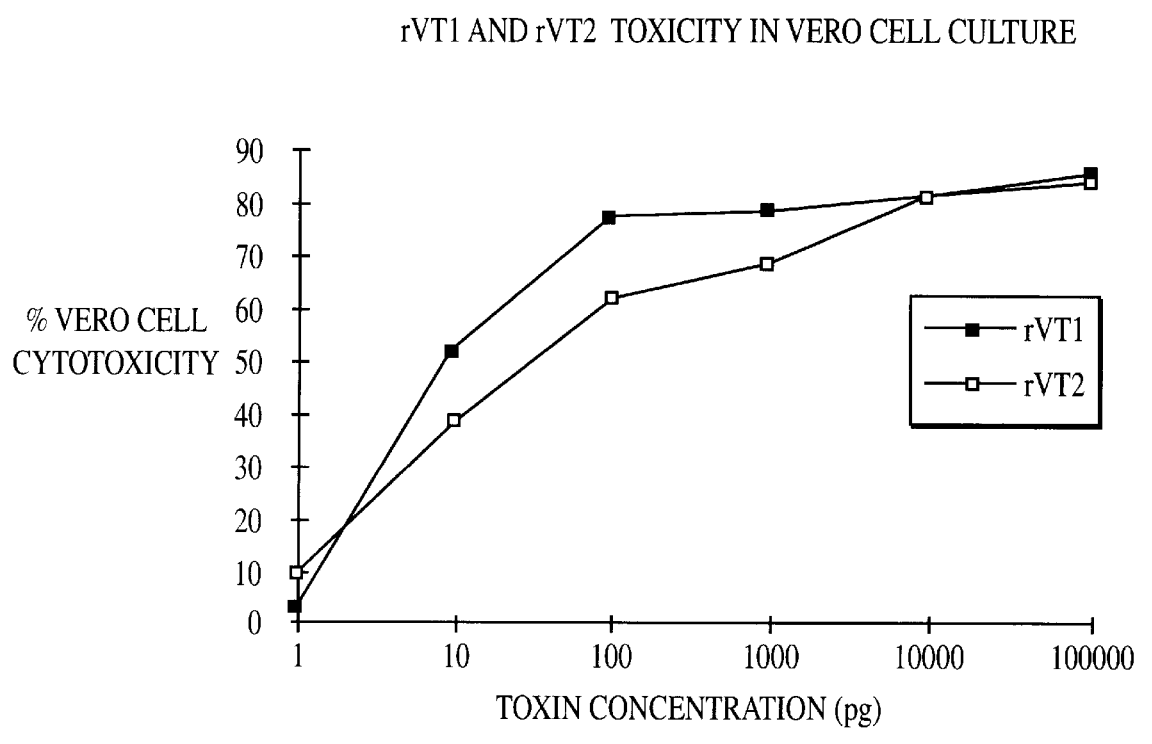

FIG. 3 shows rVT1 and rVT2 toxicity in Vero cell culture.

FIG. 6 shows Western Blot reactivity of rVT1 and rVT2 antibodies to rVTs:

Panel 6A contains preimmune IgY;

Panel 6B contains rVT1 IgY; and

Panel 6C contains rVT2 IgY.

Figure 7:
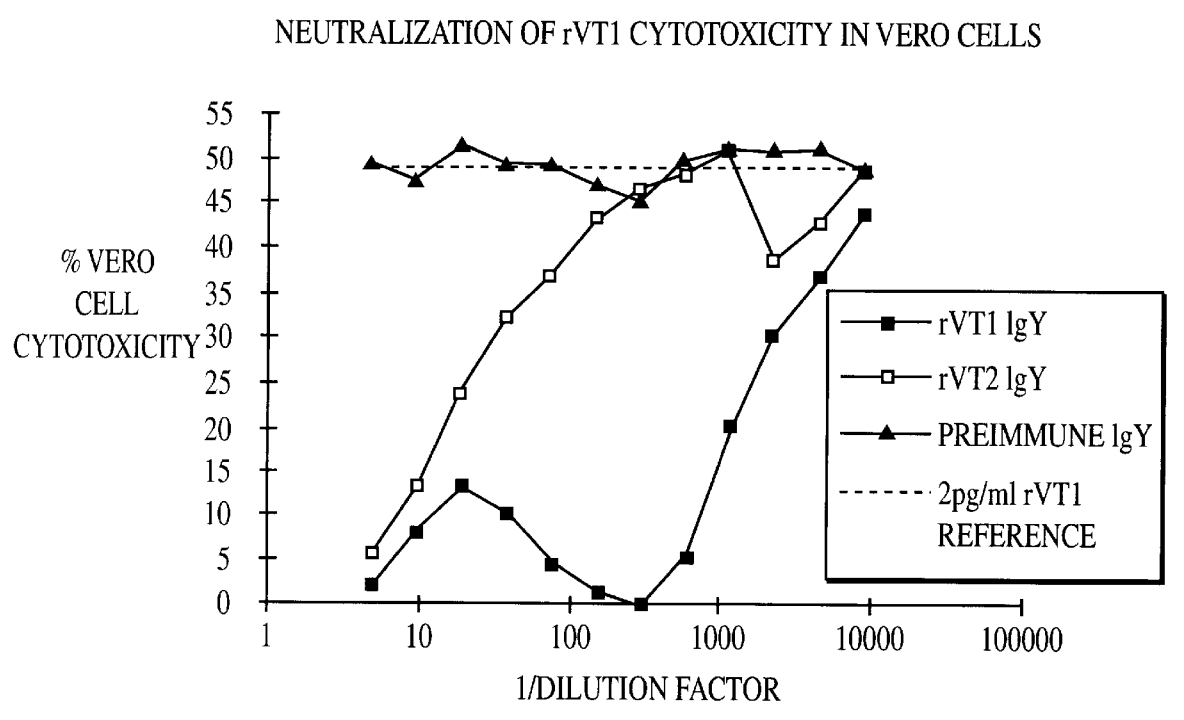

FIG. 7 shows neutralization of rVT1 cytotoxicity in Vero cells.

Figure 8:
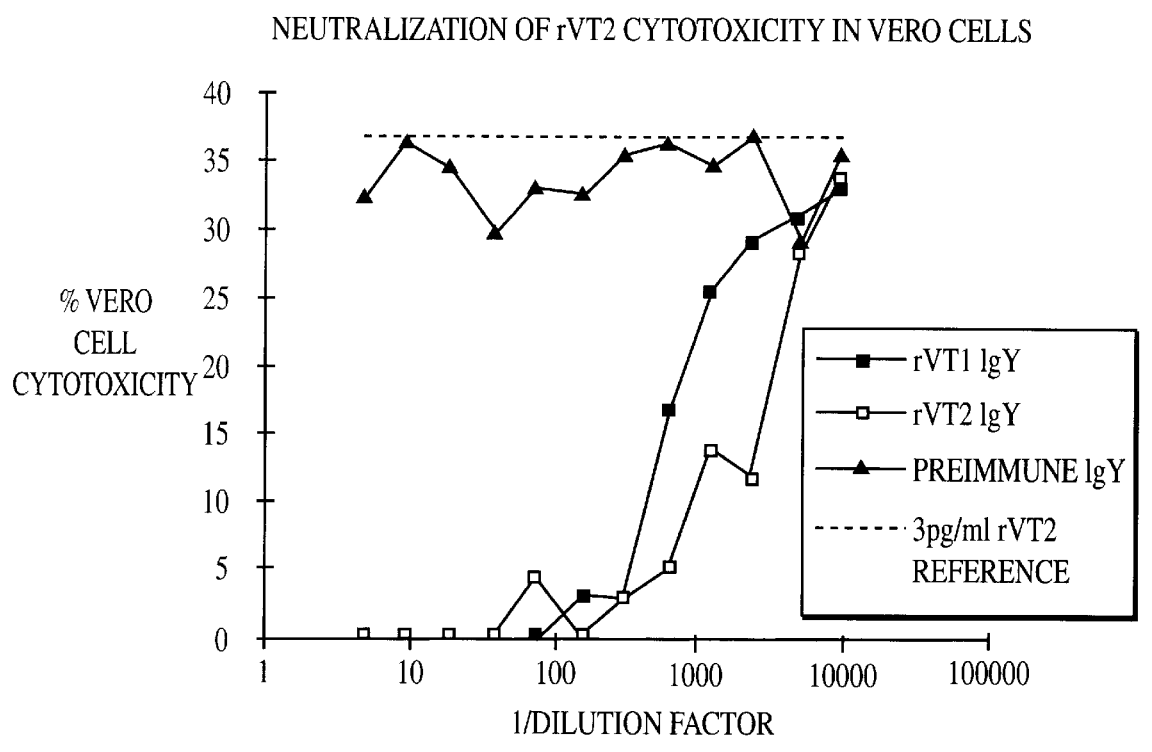

FIG. 8 shows neutralization of rVT2 cytotoxicity in Vero cells.

Figure 9:
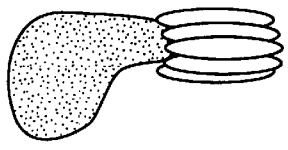
Figure 9:
Figure 9:
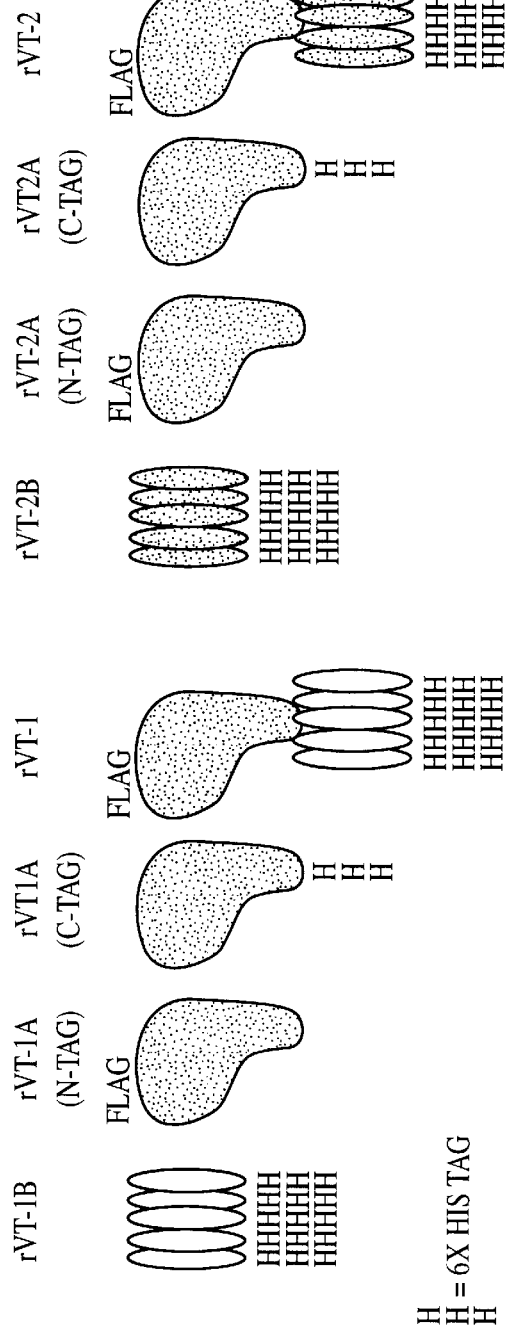

FIG. 9 shows the fusion constructs of VT components and affinity tags.

FIG. 10 shows the ELISA reactivity of VT1A IgY and VT2A IgY to rVT1.

FIG. 11 shows the ELISA reactivity of VT1A IgY and VT2A IgY to rVT2.

FIG. 12 shows the ELISA reactivity of VT1B IgY and VT2B IgY to rVT1.

FIG. 13 shows the ELISA reactivity of VT1B IgY and VT2 B IgY to rVT2.

DEFINITIONS

To facilitate understanding of the invention, a number of terms are defined below.

As used herein, the term "neutralizing" is used in reference to antitoxins, particularly antitoxins comprising antibodies, which have the ability to prevent the pathological actions of the toxin against which the antitoxin is directed. It is contemplated that neutralizing antibodies be utilized to prevent the action of toxins, in particular *E. coli* verotoxins and Shiga toxin. It is further contemplated that neutralizing antibodies be utilized to alleviate the effect(s) of toxins in an individual, in particular *E. coli* verotoxins and Shiga toxin.

As used herein, the term "immunogen" refers to a substance, compound, molecule, or other moiety which stimulates the production of an immune response. The term "antigen" refers to a substance, compound, molecule, or other moiety that is capable of reacting with products of the immune response. For example, verotoxin subunits may be used as immunogens to elicit an immune response in an animal to produce antibodies directed against the subunit used as an immunogen. The subunit may then be used as an antigen in an assay to detect the presence of anti-verotoxin subunit antibodies in the serum of the immunized animal.

As used herein, the term "overproducing" is used in reference to the production of toxin polypeptides in a host cell, and indicates that the host cell is producing more of the toxin by virtue of the introduction of nucleic acid sequences encoding the toxin polypeptide than would be expressed by the host cell absent the introduction of these nucleic acid sequences. To allow ease of purification of toxin polypeptides produced in a host cell it is preferred that the host cell express or overproduce the toxin polypeptide at a level greater than 1 mg/liter of host cell culture.

"A host cell capable of expressing a recombinant protein as a soluble protein at a level greater than or equal to 5% of the total soluble cellular protein" is a host cell in which the amount of soluble recombinant protein present represents at least 5% of the total soluble cellular protein. As used herein "total soluble cellular protein" refers to a clarified PEI lysate prepared as described in the Examples. Briefly, cells are harvested following induction of expression of recombinant protein (at a point of maximal expression). The cells are resuspended in cell resuspension buffer (CRB: 50 mM $NaPO_4$, 0.5 M NaCl, 40 mM imidazole, pH 6.8) to create a 20% cell suspension (wet weight of cells/volume of CRB) and clarified cell lysates are prepared as described in the Examples (ie., sonication or homogenization followed by centrifugation). The amount of purified recombinant protein (i.e., the eluted protein) is divided by the concentration of protein present in the clarified lysate (typically 8 mg/ml when using a 20% cell suspension as the starting material) and multiplied by 100 to determine what percentage of total soluble cellular protein is comprised of the soluble recombinant protein.

"A host cell capable of expressing a recombinant protein as a soluble protein at a level greater than or equal to X milligrams per 1 OD of cells per liter" is a host cell that produces X milligrams of recombinant protein per liter of culture medium containing a density of host cells equal to 1 $OD_{600}$. The amount of recombinant protein present per OD per liter is determined by quantitating the amount of recombinant protein recovered following affinity purification. For example as shown in Ex. 8, host cells containing the pET24hisVT1BL+ construct express the recombinant VT1B protein at a level ≧1 mg rVT1B/1 $OD_{600}$/liter. Host cells containing the pET24hisVT2BL+ construct express the recombinant VT2B protein at a level ≧10 mg rVT1B/1 $OD_{600}$/liter (See e.g., Example 8).

"A host cell capable of secreting a recombinant protein into the culture supernatant at a level greater than or equal to 10 mg recombinant protein per 1 OD of cells per liter" refers to a host cell that secretes a recombinant protein into the culture supernatant (i.e., the medium, such as L broth, used to grow the host cell) at a level greater than or equal to 10 mg recombinant protein per liter of medium containing a concentration (ie., density) of host cells equal to 1 $OD_{600}$. The host cells may be grown in shaker flasks (~1 liter culture medium) or in fermentation tank (~10 liters culture medium) and the amount of recombinant protein secreted into the culture supernatant may be determined using a quantitative ELISA assay as described in Example 12.

As used herein, the term "fusion protein" refers to a chimeric protein containing the protein of interest (i.e., an *E. coli* verotoxin and/or fragments thereof) joined to an exogenous protein fragment (the fusion partner which consists of a non-toxin protein). The fusion partner may enhance solubility of the *E. coli* protein as expressed in a host cell, may provide an "affinity tag" to allow purification of the recombinant fusion protein from the host cell or culture supernatant, or both. If desired, the fusion protein may be removed from the protein of interest (i.e., toxin protein or fragments thereof) prior to immunization by a variety of enzymatic or chemical means known to the art.

As used herein the term "non-toxin protein" or "non-toxin protein sequence" refers to that portion of a fusion protein which comprises a protein or protein sequence which is not derived from a bacterial toxin protein.

As used herein, the term "affinity tag" refers to such structures as a "polyhistidine tract" or "poly-histidine tag," or any other structure or compound which facilitates the purification of a recombinant fusion protein from a host cell, host cell culture supernatant, or both. As used herein, the term "flag tag" refers to short polypeptide marker sequence useful for recombinant protein identification and purification.

As used herein, the terms "poly-histidine tract" and "poly-histidine tag," when used in reference to a fusion protein refers to the presence of two to ten histidine residues at either the amino- or carboxy-terminus of a protein of interest. A poly-histidine tract of six to ten residues is preferred. The poly-histidine tract is also defined functionally as being a number of consecutive histidine residues added to the protein of interest which allows the affinity purification of the resulting fusion protein on a nickel-chelate or IDA column.

As used herein, the term "chimeric protein" refers to two or more coding sequences obtained from different genes, that have been cloned together and that, after translation, act as a single polypeptide sequence. Chimeric proteins are also referred to as "hybrid proteins." As used herein, the term "chimeric protein" refers to coding sequences that are obtained from different species of organisms, as well as coding sequences that are obtained from the same species of organisms.

As used herein, the term "protein of interest" refers to the protein whose expression is desired within the fusion protein. In a fusion protein, the protein of interest will be joined or fused with another protein or protein domain, the fusion partner, to allow for enhanced stability of the protein of interest and/or ease of purification of the fusion protein.

As used herein, the term "maltose binding protein" and "MBP" refers to the maltose binding protein of *E. coli.* A portion of the maltose binding protein may be added to a protein of interest to generate a fusion protein; a portion of the maltose binding protein may merely enhance the solubility of the resulting fusion protein when expressed in a bacterial host. On the other hand, a portion of the maltose binding protein may allow affinity purification of the fusion protein on an amylose resin.

As used herein, the term "purified" or "to purify" refers to the removal of contaminants from a sample. For example, antitoxins are purified by removal of contaminating non-immunoglobulin proteins; they are also purified by the removal of substantially all immunoglobulin that does not bind toxin. The removal of non-immunoglobulin proteins and/or the removal of immunoglobulins that do not bind toxin results in an increase in the percent of toxin-reactive immunoglobulins in the sample. In another example, recombinant toxin polypeptides are expressed in bacterial host cells and the toxin polypeptides are purified by the removal of host cell proteins; the percent of recombinant toxin polypeptides is thereby increased in the sample.

As used herein, the term "periplasmic" refers to the space around the plasma membrane, or more specifically, the space between the plasma membrane and the cell wall of a bacterium.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein refers to a protein which is isolated from a natural source as opposed to the production of a protein by recombinant means.

The terms "native gene" or "native gene sequences" are used to indicate DNA sequences encoding a particular gene which contain the same DNA sequences as found in the gene as isolated from nature. In contrast, "synthetic gene sequences" are DNA sequences which are used to replace the naturally occurring DNA sequences when the naturally occurring sequences cause expression problems in a given host cell. For example, naturally-occurring DNA sequences encoding codons which are rarely used in a host cell may be replaced (e.g., by site-directed mutagenesis) such that the synthetic DNA sequence represents a more frequently used codon. The native DNA sequence and the synthetic DNA sequence will preferably encode the same amino acid sequence.

As used herein the term "portion" when in reference to a protein (as in "a portion of a given protein") refers to fragments of that protein. The fragments may range in size from four amino acid residues to the entire amino acid sequence minus one amino acid.

As used herein "soluble" when in reference to a protein produced by recombinant DNA technology in a host cell, is a protein which exists in solution in the cytoplasm of the host cell; if the protein contains a signal sequence, the soluble protein is exported to the periplasmic space in bacterial hosts and is secreted into the culture medium of eukaryotic cells capable of secretion or by bacterial hosts possessing the appropriate genes. In contrast, an insoluble protein is one which exists in denatured form inside cytoplasmic granules (i.e., inclusion bodies) in the host cell. High level expression (i.e., greater than 1 mg recombinant protein/liter of bacterial culture) of recombinant proteins often results in the expressed protein being found in inclusion bodies in the bacterial host cells. A soluble protein is a protein which is not found in an inclusion body inside the host cell or is found both in the cytoplasm and in inclusion bodies and in this case the protein may be present at high or low levels in the cytoplasm.

A distinction is drawn between a soluble protein (i.e., a protein which when expressed in a host cell is produced in a soluble form) and a "solubilized" protein. An insoluble recombinant protein found inside an inclusion body may be solubilized (i.e., rendered into a soluble form) by treating purified inclusion bodies with denaturants such as guanidine hydrochloride, urea or sodium dodecyl sulfate (SDS). These denaturants must then be removed from the solubilized protein preparation to allow the recovered protein to renature (refold). Not all proteins will refold into an active conformation after solubilization in a denaturant and removal of the denaturant. Many proteins precipitate upon removal of the denaturant. SDS may be used to solubilize inclusion bodies and will maintain the proteins in solution at low concentration. However, dialysis will not always remove all of the SDS (SDS can form micelles which do not dialyze out); therefore, SDS-solubilized inclusion body protein is soluble but not refolded.

A distinction is drawn between proteins which are soluble (i.e., dissolved) in a solution devoid of significant amounts of ionic detergents (e.g., SDS) or denaturants (e.g., urea, guanidine hydrochloride) and proteins which exist as a suspension of insoluble protein molecules dispersed within the solution. A soluble protein will not be removed from a solution containing the protein by centrifugation using conditions sufficient to remove bacteria present in a liquid medium (i.e., centrifugation at 12,000 x g for 4–5 minutes). For example, to test whether two proteins, protein A and protein B, are soluble in solution, the two proteins are placed into a solution selected from the group consisting of PBS-NaCl (PBS containing 0.5 M NaCl), PBS-NaCl containing 0.2% Tween 20, PBS, PBS containing 0.2% Tween 20, PBS-C (PBS containing 2 mM $CaCl_2$), PBS-C containing either 0.1 or 0.5% Tween 20, PBS-C containing either 0.1 or 0.5% NP-40, PBS-C containing either 0.1 or 0.5% Triton X-100, PBS-C containing 0.1% sodium deoxycholate. The mixture containing proteins A and B is then centrifuged at 5000 x g for 5 minutes. The supernatant and pellet formed by centrifugation are then assayed for the presence of protein A and B. If protein A is found in the supernatant and not in the pellet [except for minor amounts (i.e., less than 10%) as a result of trapping], protein is said to be soluble in the solution tested. If the majority of protein B is found in the pellet (I.e., greater than 90%), then protein B is said to exist as a suspension in the solution tested.

As used herein, the term "reporter reagent" or "reporter molecule" is used in reference to compounds which are capable of detecting the presence of antibody bound to antigen. For example, a reporter reagent may be a colorimetric substance which is attached to an enzymatic substrate. Upon binding of antibody and antigen, the enzyme acts on its substrate and causes the production of a color. Other reporter reagents include, but are not limited to fluorogenic and radioactive compounds or molecules.

As used herein the term "signal" is used in reference to the production of a sign that a reaction has occurred, for example, binding of antibody to antigen. It is contemplated that signals in the form of radioactivity, fluorogenic reactions, and enzymatic reactions will be used with the present invention. The signal may be assessed quantitatively as well as qualitatively.

As used herein, the term "therapeutic amount" refers to that amount of antitoxin required to neutralize the pathologic effects of *E. coli* toxin in a subject.

As used herein, the term "acute intoxication" is used in reference to cases of *E. coli* infection in which the patient is currently suffering from the effects of toxin (e.g., *E. coli* verotoxins or enterotoxins). Signs and symptoms of intoxication with the toxin may be immediately apparent. Or, the determination of intoxication may require additional testing, such as detection of toxin present in the patient's fecal material.

As used herein, the term "at risk" is used in references to individuals who have been exposed to *E. coli* and may suffer the symptoms associated with infection or disease with these organisms, especially due to the effects of verotoxins.

The term "pyrogen" as used herein refers to a fever-producing substance. Pyrogens may be endogenous to the host (e.g., prostaglandins) or may be exogenous compounds (e.g., bacterial endo- and exotoxins, non-bacterial compounds such as antigens and certain steroid compounds, etc.). The presence of pyrogen in a pharmaceutical solution may be detected using the U.S. Pharmacopeia (USP) rabbit fever test (United States Pharmacopeia, Vol. XXII (1990) United States Pharmacopeial Convention, Rockville, Md., p. 151).

The term "endotoxin" as used herein refers to the high molecular weight complexes associated with the outer membrane of gram-negative bacteria. Unpurified endotoxin contains lipids, proteins and carbohydrates. Highly purified endotoxin does not contain protein and is referred to as lipopolysaccharide (LPS). Because unpurified endotoxin is of concern in the production of pharmaceutical compounds (e.g., proteins produced in E. coli using recombinant DNA technology), the term endotoxin as used herein refers to unpurified endotoxin. Bacterial endotoxin is a well known pyrogen.

As used herein, the term "endotoxin-free" when used in reference to a composition to be administered parenterally (with the exception of intrathecal administration) to a host means that the dose to be delivered contains less than 5 EU/kg body weight (FDA Guidelines for Parenteral Drugs [December 1987]). Assuming a weight of 70 kg for an adult human, the dose must contain less than 350 EU to meet FDA Guidelines for parenteral administration. Endotoxin levels are measured herein using the Limulus Amebocyte Lysate (LAL) test (Limulus Amebocyte Lysate Pyrochrome™, Associates of Cape Cod, Inc. Woods Hole, Mass.). To measure endotoxin levels in preparations of recombinant proteins, 0.5 ml of a solution comprising 0.5 mg of purified recombinant protein in 50 mM $NaPO_4$, pH 7.0, 0.3 M NaCl and 10% glycerol is used in the LAL assay according to the manufacturer's instructions for the endpoint chromogenic without diazo-coupling method [the specific components of the buffer containing recombinant protein to be analyzed in the LAL test are not important; any buffer having a neutral pH may be employed. Compositions containing less than or equal to than 250 endotoxin units (EU)/mg of purified recombinant protein are herein defined as "substantially endotoxin-free." Preferably the composition contains less than or equal to 100, and most preferably less than or equal to 60, (EU)/mg of purified recombinant protein. Typically, administration of bacterial toxins or toxoids to adult humans for the purpose of vaccination involves doses of about 10–500 µg protein/dose. Therefore, administration of 10–500 µg of a purified recombinant protein to a 70 kg human, wherein said purified recombinant protein preparation contains 60 EU/mg protein, results in the introduction of only 0.6 to 30 EU (i.e., 0.2 to 8.6% of the maximum allowable endotoxin burden per parenteral dose). Administration of 10–500 µg of a purified recombinant protein to a 70 kg human, wherein said purified recombinant protein preparation contains 250 EU/mg protein, results in the introduction of only 2.5 to 125 EU (i.e., 0.7 to 36% of the maximum allowable endotoxin burden per parenteral dose).

The LAL test is accepted by the U.S. FDA as a means of detecting bacterial endotoxins (21 C.F.R. §§ 660.100–105). Studies have shown that the LAL test is equivalent or superior to the USP rabbit pyrogen test for the detection of endotoxin and thus the LAL test can be used as a surrogate for pyrogenicity studies in animals (F. C. Perason, *Pyrogens: endotoxins, LAL Testing and Depyrogenation*, Marcel Dekker, N.Y. [1985], pp.150–155). The FDA Bureau of Biologics accepts the LAL assay in place of the USP rabbit pyrogen test so long as the LAL assay utilized is shown to be as sensitive as, or more sensitive as the rabbit test (Fed. Reg., 38, 26130 (1980]).

The term "monovalent" when used in reference to a verotoxin vaccine refers to a vaccine which is capable of provoking an immune response in a host animal directed against a single type of verotoxin. For example, if immunization of a host with E. coli VT1 toxin vaccine induces antibodies in the immunized host which protect against a challenge with VT1, but not against challenge with other toxins (e.g., VT2), then the VT1 vaccine is said to be monovalent. In contrast, a "multivalent" vaccine provokes an immune response in a host animal directed against more than one verotoxin. For example, if immunization of a host with a vaccine comprising VT1 and VT2 verotoxins induces the production of antibodies which protect (i.e., "protective antibody") the host against a challenge with both VT1 and VT2, the vaccine is said to be multivalent (in particular, this hypothetical vaccine is bivalent). It is intended that multivalent vaccines of the present invention encompass numerous embodiments. For example, it is also contemplated that recombinant E. coli verotoxin proteins be used in conjunction with either native toxins or toxoids from other organisms as antigens in a multivalent vaccine preparation. It is further contemplated that multivalent vaccines of the present invention will stimulate an immune response against various E. coli serotypes, including, but not limited to E. coli O157:H7, O216:H11, O113:H21, O91:H21, and O111:NM, in humans and/or other animals.

As used herein the term "immunogenically-effective amount" refers to that amount of an immunogen required to invoke the production of protective levels of antibodies in a host upon vaccination.

The term "protective level", when used in reference to the level of antibodies induced upon immunization of the host with an immunogen which comprises a bacterial toxin, means a level of circulating antibodies sufficient to protect the host from challenge with a lethal or an detrimental dose of the toxin.

As used herein the terms "protein" and "polypeptide" refer to compounds comprising amino acids joined via peptide bonds and are used interchangeably.

The terms "toxin" when used in reference to toxins produced by members (i.e., species and strains) of the genera Escherichia and Shigella are used interchangeably and refer to verotoxins, Shigatoxin, or Shiga-like toxins The term "receptor-binding domain" when used in reference to verotoxin refers to the area of the B subunit presumed to be responsible for the binding of the holotoxin to the receptor on the target eukaryotic cell. The receptor for VT1 and VT2 is a globotriaosyl ceramide containing a galactose α-(1-4)-galactose-β-(1-4) glucose ceramide (Gb3). The present invention contemplates fusion proteins comprising the receptor-binding domain of verotoxins (e.g., VT1 and VT2) from E. coli, including the variants found among different strains within a given serotype, in particular E. coli O157:H7. Fusion proteins containing an analogous region from a strain other than the prototype strain are encompassed by the present invention.

Fusion proteins comprising the receptor binding domain (i.e., the B subunit) of botulinal toxins may include amino acid residues located beyond the termini of the domains defined above.

SUMMARY OF THE INVETION

The present invention relates to antitoxin therapy for humans and other animals. Antitoxins which neutralize the pathologic effects of E. coli toxins are generated by immunization of avian hosts with recombinant toxin fragments. In one embodiment, the present invention contemplates a method of treatment administering at least one antitoxin directed against at least a portion of an *Escherichia coli* verotoxin in an aqueous solution in therapeutic amount that is administrable to an intoxicated subject. It is contemplated that the intoxicated subject will be either an adult or a child.

In a preferred embodiment, the *E. coli* verotoxin is recombinant. In one embodiment, the antitoxin is an avian antitoxin. In an alternative embodiment, the recombinant *E. coli* verotoxin is a fusion protein comprising a non-verotoxin protein sequence and a portion of the *Escherichia coli* verotoxin VT1 sequence. In one embodiment of the *E. coli* fusion protein, the fusion protein comprises a non-verotoxin protein sequence and a portion of the *Escherichia coli* verotoxin VT2 sequence.

Various routes of administration, are contemplated for providing the *E. coli* antitoxin(s) to an affected individual, including but not limited to, parenteral as well as oral routes of administration. In a particularly preferred embodiment, the route of administration is parenteral.

The present invention also includes the embodiment of a method of prophylactic treatment in which an antitoxin directed against at least one *E. coli* verotoxin in an aqueous solution in therapeutic amount that is parenterally administrable, and is administered to at least one subject at risk of diarrheal disease. It one embodiment, the antitoxin is parenterally administered.

In one embodiment, the subject is at risk of developing extra-intestinal complications of *E. coli* infections, including but not limited to, hemolytic uremic syndrome, thrombotic thrombocytopenic purpura, etc.

The present invention also includes the embodiment of a composition which comprises neutralizing antitoxin directed against at least one *E. coli* verotoxin in an aqueous solution in therapeutic amounts. In one particularly preferred embodiment, the *E. coli* verotoxin is a recombinant toxin. In an alternative embodiment, the recombinant *E. coli* verotoxin is a fusion protein comprising a non-verotoxin protein sequence and a portion of the *E. coli* verotoxin VT1 sequence. In another embodiment, the recombinant *E. coli* verotoxin is a fusion protein comprising a non-verotoxin protein sequence and a portion of the *E. coli* verotoxin VT2 sequence. In yet another embodiment, the composition of the antitoxin is directed against a portion of at least one *Escherichia coli* verotoxin. In one embodiment, the portion of *Escherichia coli* is selected from the group consisting of subunit A and subunit B of VT1. In an alternative embodiment, the portion of *Escherichia coli* is selected from the group consisting of subunit A and subunit B of VT2. Indeed, the invention contemplates an antitoxin that is directed against a portion of at least one *Escherichia coli* verotoxin. In one embodiment, the antitoxin is an avian antitoxin.

The present invention also comprises a method of treatment of enteric bacterial infections comprising administering an avian antitoxin directed against at least one verotoxin produced by *E. coli* in an aqueous solution in therapeutic amount, to at least one infected subject. In one preferred embodiment, the avian antitoxin is administered parenterally.

In another embodiment, the *E. coli* is selected from the group consisting of *Escherichia coli* serotypes O157:H7, O1:NM; O2:H5; O2:H7; O4:NM; O4:H10; O5:NM; O5:H16; O6:H1; O18:NM; O18:H7; O25:NM; O26:NM; O26:H11; O26:H32; O38:H21; O39:H4; O45:H2; O50:H7; O55:H7; O55:H10; O82:H8; O84:H2; O91:NM; O91:H21; O103:H2; O111:NM; O111:H8; O111:H30; O111:H34; O113:H7; O113:H21; O114:H48; O115:H10; O117:H4; O118:H12; O118:H30; O121:NM; O121:H19; O125:NM; O125:H8; O126:NM; O126:H8; O128:NM; O128:H2; O128:H8; O128:H12; O128:H25; O145:NM; O125:H25; O146:H21; O153:H25; O157:NM; O163:H19; O165:NM; O165:19; and O165:H25. In one embodiment, the antitoxin comprises antitoxin directed against at least one *Escherichia coli* verotoxin. In another embodiment, the antitoxin is cross-reacts with at least one *Escherichia coli* verotoxin. In yet another embodiment, the antitoxin is reactive against toxins produced by members of the genus Shigella, including *S. dysenteriae*.

The present invention also contemplates uses for the toxin fragments in vaccines and diagnostic assays. The fragments may be used separately as purified, soluble antigens or, alternatively, in mixtures or "cocktails." The present invention thus comprises a method for detecting *Escherichia coli* verotoxin in a sample in which a sample, an antitoxin raised against *Escherichia coli* verotoxin, and a reporter reagent capable of binding the antitoxin are provided. The antitoxin is added to the sample, so that the antitoxin binds to the *E. coli* verotoxin in the sample. In one embodiment, the antitoxin is an avian antitoxin. In an alternative embodiment, the method further comprises the steps of washing unbound antitoxin from the sample, adding at least one reporter reagent to the sample, so that the reporter reagent binds to any antitoxin that is bound, washing the unbound reporter reagent from the sample and detecting the reporter reagent bound to the antitoxin bound to the *Escherichia coli* verotoxin, so that the verotoxin is detected. In one embodiment, the detecting is accomplished through any means, such as enzyme immunoassay, radioimmunoassay, fluorescence immunoassay, flocculation, particle agglutination, and in situ chromogenic assay. In one preferred embodiment, the sample is a biological sample. In an alternative preferred embodiment, the sample is an environmental sample.

The present invention also provides a recombinant expression vector, in which the vector encodes an affinity tag and protein comprising at least a portion of bacterial toxin selected from the group consisting of *Escherichia coli* type 1 verotoxin and *Escherichia coli* type 2 verotoxin. In preferred embodiments, the vector comprises nucleic acid encoding at least a portion of an amino acid sequence selected from the group consisting of SEQ ID NOS: 4, 8, 21, 23, 25, 27, 47, and 49. In particularly preferred embodiments, the affinity tag comprises a polyhistidine tract or the maltose binding protein.

In one embodiment, the recombinant expression vector contains a portion of *Escherichia coli* type 1 verotoxin selected from the group consisting of *Escherichia coli* type 1 verotoxin subunit A, *Escherichia coli* type 1 verotoxin subunit B, *Escherichia coli* type 2 verotoxin subunit A, and *Escherichia coli* type 2 verotoxin subunit B. In preferred embodiments, the affinity tag is selected from the group consisting of a polyhistidine tract and maltose binding protein.

In yet another embodiment, the present invention provides a host cell capable of expressing a recombinant verotoxin protein as a soluble protein at a level of at least 1 milligram per 1 OD of the host cells per liter. In an alternative embodiment, the recombinant verotoxin protein is expressed as a soluble protein at a level of at least 10 milligrams per 1 OD of the host cells per liter.

In an alternative embodiment, the present invention provides a host cell containing a recombinant expression vector, the vector encoding an affinity tag and protein comprising at least a portion of bacterial toxin, the toxin selected from the group consisting of *Escherichia coli* type 1 verotoxin, *Escherichia coli* type 2 verotoxin, and Shiga toxin. In preferred embodiments, the host cell contains an expression vector selected from the group consisting of pET24hisVT2BL+, pET24hisVT1BL+, and pET23hisVT2AL−.

In yet another embodiment, the present invention provides a host cell expressing toxin portion that is selected from the group consisting of *Escherichia coli* type 1 verotoxin subunit A, *Escherichia coli* type 1 verotoxin subunit B, *Escherichia coli* type 2 verotoxin subunit A, and *Escherichia coli* type 2 verotoxin subunit B.

In preferred embodiments, the host cell is a bacterial cell. In particularly preferred embodiments, the host cell is an *Escherichia coli* cell, in another embodiment, the host cell is a Shigella cell.

In alternatively preferred embodiments, the host cell of the present invention is an eukaryotic cell. In preferred embodiments, the host cell is an insect, yeast, or mammalian cell.

The present invention also provides a host cell containing a recombinant expression vector, in which the vector encodes a fusion protein comprising a non-toxin protein sequence and at least a portion of a bacterial toxin, wherein the toxin selected from the group consisting of *Escherichia coli* type 1 verotoxin, *Escherichia coli* type 2 verotoxin, and Shiga toxin.

In alternative embodiments, the host cell contains *Escherichia coli* verotoxin portion is selected from the group consisting of *Escherichia coli* type 1 verotoxin subunit A, *Escherichia coli* type 1 verotoxin subunit B, *Escherichia coli* type 2 verotoxin subunit A, and *Escherichia coli* type 2 verotoxin subunit B. In particularly preferred embodiments, the non-toxin protein sequence is selected from the group comprising a poly-histidine tract and the maltose binding protein.

The present invention also provides methods of generating neutralizing antibody directed against *Escherichia coli* verotoxin comprising: providing in any order: an antigen comprising a fusion protein comprising a non-toxin protein sequence and at least a portion of a *Escherichia coli* verotoxin, the toxin selected from the group consisting of type 1 toxin and type 2 toxin, a host; and immunizing the host with the antigen so as to generate a neutralizing antibody.

In preferred embodiments of the method, the antigen further comprises a fusion protein comprising a non-toxin protein sequence and at least a portion of *Escherichia coli* verotoxin selected from the group comprising *Escherichia coli* type 1 verotoxin and *Escherichia coli* type 2 verotoxin. In alternatively preferred embodiments, the antigen is cross-linked. In particularly preferred embodiments, the non-toxin protein sequence comprises a poly-histidine tract or the maltose binding protein. In preferred embodiments of the method, the host is a chicken, mammal (including humans).

In yet another preferred embodiment, the methods further comprise the step of collecting antibodies from the host. In yet another alternative embodiment, the methods further comprise the step of purifying the antibodies to provide an antibody preparation. In particularly preferred embodiments of the method, the purifing comprises affinity purification. In alternatively preferred embodiments, the purified antibody preparation contains 0.2 to 1% specific antibody.

The present invention also provides the antibody prepared according to the methods described above. In particular embodiments, the antibody raised according to the methods wherein the produced antibody is an avian antibody. In alternatively preferred embodiments, the antibody raised according to the methods, wherein the antibody is protective.

The present invention also provides methods of treatment comprising: providing: neutralizing antitoxin directed against at least a portion of an *Escherichia coli* recombinant verotoxin in an aqueous solution in therapeutic amount that is administrable, and an intoxicated subject; and administering the antitoxin to the subject. In preferred embodiments, the antitoxin is an avian antitoxin, while in alternative preferred embodiments, the antitoxin is a mammalian antitoxin.

In alternative embodiments of the methods, the recombinant *Escherichia coli* verotoxin is a fusion protein comprising a non-verotoxin protein sequence and a portion of *Escherichia coli* verotoxin VT1 sequence. In alternatively preferred embodiments, the recombinant *Escherichia coli* verotoxin is a fusion protein comprising a non-verotoxin protein sequence and a portion of *Escherichia coli* verotoxin VT sequence selected from the group comprising the VT1 subunit A sequence, the VT1subunit B sequence, VT2 subunit A sequence, and VT2 subunit B sequence. In alternative preferred embodiments, the recombinant *Escherichia coli* verotoxin is a fusion protein is cross-linked.

It is contemplated that the subject of the methods be either an adult or a child. It is further contemplated that the administering be accomplished by various methods, including but not limited to parenteral or oral.

The present invention also provides methods of prophylactic treatment comprising: providing: a neutralizing antitoxin directed against at least one *Escherichia coli* recombinant verotoxin in an aqueous solution in therapeutic amount that is parenterally administrable, and at least one subject is at risk of diarrheal disease; and parenterally administering the antitoxin to the subject.

In preferred embodiments of the methods, the antitoxin directed against *Escherichia coli* recombinant verotoxin is directed against *Escherichia coli* verotoxin type 1, or type 2. In particularly preferred embodiments, the antitoxin is directed against *Escherichia coli* recombinant verotoxin is directed against *Escherichia coli* verotoxin type 1 subunit B or verotoxin type 2 subunit B.

In alternatively preferred embodiments, the subject is at risk of developing extra-intestinal complications of *Escherichia coli* infection. It is also contemplated that the subject be at risk of or experiencing extra-intestinal complication is hemolytic uremic syndrome.

The present invention also provides vaccines comprising a fusion protein, the fusion protein comprising a non-toxin protein sequence and at least a portion of a bacterial toxin, the verotoxin selected from the group consisting of *Escherichia coli* type 1 verotoxin, *Escherichia coli* type 2 verotoxin, and Shiga toxin.

In preferred embodiments, the vaccine further comprises a fusion protein comprising a non-toxin protein sequence and at least a portion of *Escherichia coli* verotoxin type 1 verotoxin. In alternative preferred embodiments, the vaccine further comprises a fusion protein comprising a non-toxin protein sequence and at least a portion of *Escherichia coli* verotoxin type 2 verotoxin. In yet other alternative embodiments, the vaccine comprises non-toxin protein sequence selected from the group consisting of poly-histidine tract and maltose binding protein. In yet other alternative embodiments, vaccine substantially endotoxin-free. In further alternative embodiments, the bacterial toxin is cross-linked.

DESCRIPTION OF THE INVENTION

The present invention contemplates preventing or treating humans and other animals intoxicated with at least one bacterial toxin. It is contemplated that administration of antitoxin will be used to treat patients effected by or at risk of symptoms due to the action of bacterial toxins. It is also contemplated that the antitoxin will be used in a diagnostic assay to detect the presence of toxins in samples. The present invention further provides methods for preparation and utilization of immunogens and antigens. In preferred embodiments, these preparations are obtained using recombinant methodologies. The immunogens, organisms, toxins and individual steps of the present invention are described separately below.

I. Production of Immunogens/Antigens

In preferred embodiments, the present invention provides methods for the over-expression of VT1 and VT2 subunits. Cloning of the VT1 and VT2 gene clusters on high copy number plasmids (e.g., pUC19 or pBS; Stratagene) has been used to overexpress the toxins in E. coli. In some instances, periplasmic extracts were utilized for biochemical purification of the toxins. However, this approach of coordinate expression of toxin subunits has disadvantages, such as the inherent toxicity of the toxins on the cell lines, which necessitates the use of specialized facilities for growth of organisms and purification of the toxins.

A and B chains of VT1 and VT2 have also individually expressed in E. coli, utilizing recombinant DNA methodologies. However, the present invention provides methods for the expression of toxin subunits from high copy number plasmids or expression vectors, periplasmic secretion, and ready purification of folded protein. The location of expression in the periplasmic space is very desirable, as the A and B subunits contain disulfide bonds that cannot be formed intracellularly due to the reducing environment. In addition, in order to be conformationally correct, the B subunit must be able to associate into pentamers.

In the present invention, the pET vector derived verotoxin expression constructs were transformed into E. coli strain BL21(DE3). A listing of several plasmid constructs can be found in Table 10, below. Each plasmid containing a his-tagged subunit was tested for its effect on the viability of the host strain (i.e., BL21[DE3]). In general, constructs that did not tightly repress the expression of the recombinant subunit through the use of the T7lac promoter/LacIq gene were lethal to the strain. Plasmids that were not stable in BL21 (DE3) were also tested in strains harboring plysS or plysE. These plasmids contain the gene for T7 lysozyme, a natural inhibitor of T7 RNA polymerase. Co-expression of the lysS or lysE gene typically prevented cell death caused by the subunit.

In the present invention, protein expression in cultures utilizing recombinant plasmids in the BL21(DE3) derived E. coli strains was induced by addition of IPTG. For optimal protein expression, cultures were grown at 30–32° C. overnight, induced when the cell density reached >2 $OD_{600}$. Induced protein was then allowed to accumulate for 2–4 hrs after induction. Induction at lower $OD_{600}$ readings (e.g., 0.50–1.0) resulted in accumulation of lower overall levels of verotoxin subunits, since induction of subunit expression halted E. coli cell growth and final cell pellets were therefore dramatically smaller. In the case of VT1 B and VT2 B-expressing constructs, the verotoxin subunits were insoluble if grown and induced at 37° C.

Although high level expression of the VT1 B subunit has been attainable in either E. coli or V. cholerae, prior to the present invention, biochemical purification procedures have resulted in suboptimal recovery of the subunit from periplasmic extracts. The present invention addresses these problems known in the art, in order to recover relatively high levels of expressed subunit from small and large-scale cultures.

In regards to VT2, very low level expression of the A subunit have been previously reported, while expression levels of soluble affinity purifiable GST-B subunit fusion were reported to be on the order of 1 mg/liter. Since this expression is intracellular, the purified proteins produced are unlikely to be conformationally correct.

Several expression constructs to overexpress the VT2 B subunits either periplasmically or cytoplasmically have been reported (Acheson et al, Infect. Immun. 63, 301–308 [1995]). In these constructs the VT2 B subunit was overexpressed in E. coli under the control of the T7 or tac promoter. However, the VT2 B subunits expressed utilizing these systems appeared to form unstable multimers, indicating that coassembly with the A subunit is necessary to form stable pentamers. Although high level expression was reported, only low yields of purified protein were recovered (i.e., 1 mg from a 10 liter fermentation).

The present invention provides methods for the periplasmic expression of individual verotoxin subunits in E. coli that are apparently conformationally correct, and can be assembled in vivo with purified A subunit holotoxin to produce holotoxin that is conformationally and functionally identical to purified native holotoxin. Intracellular expression of subunits, while potentially yielding higher levels of expression, might require refolding strategies to obtain native conformation. The development of large scale purification methods of the present invention, such as those in some embodiments, that utilize the incorporation of an affinity tag to facilitate single step affinity purification of subunits from periplasmic extracts, greatly enhances and simplifies the prior purification schemes based on biochemical (Donohue-Rolfe, [1991]), immunoaffinity chromatography (Donohue-Rolfe et al., supra [1984]), or ligand binding (Donohue-Rolfe et al., supra [1989]) strategies.

Affinity tagging VT-1 and VT-2.

To maintain protein conformation of the B subunits, the incorporated affinity tag must not interfere with subunit folding or pentamer formation. During the development of the present invention, molecular dissections of the VT1 B and VT2 B subunits, as well as X-ray crystallography data, indicated that C-terminally tagged B chains may be functionally and conformationally unaltered. The crystal structure of VT1 B chain pentamers (Stein et al., supra [1992]) and Shiga holotoxin (Fraser et al., supra [1994]) have been solved. Based on these structures and mutagenesis of the B chain of VT1 and VT2, purification of recombinant B chains using a C-terminal epitope tag was accomplished.

In addition, neutralizing epitopes are present at both the N- and C terminal regions of Shiga toxin B, since polyclonal antibodies raised against peptides from these regions (i.e, aa5–18, 13–26, 7–26 from the N terminal, and aa54–67 and 57–67) show partial neutralization of Shiga toxin (Harari, [1990]; Harari, [1988]). It was contemplated that alteration of the N or C terminal by addition of an affinity tag may alter these epitopes. Indeed, it has been reported that deletion of the last 5 amino acids of Shiga toxin B (Jackson et al., supra [1990]) or 4 amino acids of VT2 B (Perera et al., supra) eliminate toxin activity, while deletion of the last 2 aa of VT2 B subunit reduced cytotoxicity (Perera et al., supra). However, the addition of an 18 or 21 aa extension to the C terminus of the VT2 B chain was presumably conformationally correct and facilitated pentamer and holotoxin assembly since these proteins assembled cytotoxic holotoxin (Perera et al., supra). These C terminal extensions did not alter binding of a monoclonal antibody reactive to the C terminal of the B chain (Perera et al., supra). These results indicated that addition of a small affinity tag to the C terminal of the VT2, and perhaps VT1, B chain may not alter conformation or pentamer assembly.

Although a large variety of expression systems have been designed to facilitate expression of affinity tagged fusion proteins in E. coli, most systems utilize relatively large affinity tags, such as maltose binding protein, protein A, B-galactosidase, Glutathione S-transferase or thioredoxin, in which the affinity tag represents 12→100 kd in size. In view of the fact that the VT1 and VT2 B chains are only approximately 8 kd in size, utilization of such a large affinity tag was viewed during the development of the present invention, as being likely to compromise the activity of the subunit. Instead, the present invention provides a small (<1 kd) 6X histidine sequence (i.e., His-His-His-His-His-His) as an affinity tag as. This sequence was found to bind to immobilized metal ions at an affinity as high as 1013 (for Ni ions). This allows the simple one step purification of fusion proteins containing this tag from cell lysates by immobilized metal affinity chromatography (IMAC) of the present invention. Such purifications are scaleable to facilitate purification of gram quantities of protein, and, due to the absence of a polyhistidine tag on E. coli proteins, provides yields of highly pure protein preparations. Furthermore, the poly-his tag is non-immunogenic, such that most antibodies raised against poly-his containing proteins will be specific to the fusion partner. In most cases this alleviates the need to cleave the fusion peptide from this tag before immunization.

However, it is contemplated that for expression of VT1 A and VT2 A chains, a number of N or C terminal affinity tags may be utilized, since this subunit does not form multimers, and downstream assembly of A and B chains to form holotoxin will not be performed.

The present invention provides methods for the expression and purification of large quantities (e.g., 40 mg/l) of the VT2 B subunit. However, it was observed that due to the toxicity of the VT2 B subunit, strict uninduced promoter control is necessary to permit cell viability. In one embodiment, this is accomplished by coexpression with the plysE plasmid (for the pET23hisVT2BL+ plasmid), or the presence of the lacIq gene and the T7 lac promoter (for the pET24hisVT2BL+ and L– plasmids).

Due to the need for disulfide bond formation and pentamer assembly, the vectors that allow periplasmic secretion of the protein (L+) are preferable, since intracellular E. coli is a reducing environment. Due to scale-up and plasmid stability concerns, in preferred embodiments, the pET24 construct is preferable to the pET 23 construct.

The present invention also provides methods for the expression and purification of moderate quantities (5 mg/l) of the VT1 B subunit. The VT1 B subunit is less toxic than the VT2 B subunit, allowing less stringent control of uninduced verotoxin expression. Nonetheless, due to the need for disulfide bond formation and pentamer assembly, in preferred embodiments, the vectors that allow periplasmic secretion of the protein (L+) are preferable, since intracellular E. coli is a reducing environment. Due to scale-up and plasmid stability concerns, the pET24 construct is preferable to the pET 23 construct.

Due to the poor recovery of his-tagged VT1 A and VT2 A protein, expression of MBP fused VT1 A and VT2 A subunits was undertaken. Cultures of pMalVT1A, pMalVT2A and pMalVT2A (BamHI) were grown in the Bl21 plysS strain, induced with IPTG, and the soluble protein fractions were isolated. Soluble extracts were bound to an amylose resin column, washed and eluted with maltose. In these embodiments, protein yields were 22 mg/l (pMalVT1A), 13.5 mg/l (pMalVT2A) or 12.5 mg/l (pMalVT2A[BamHI]).

The identity of the predicted full length VT1 A and VT2 A proteins was confirmed by Western blot analysis. Verotoxin protein was identified utilizing a chicken anti-VT1 holotoxin antiserum. This analysis confirmed that the full length proteins detected by Coomassie gel analysis were immunoreactive with the anti-VT1 antibody preparation. The reactivity of the VT2 A protein with the VT1 antiserum was predicted, since in early experiments undertaken during the development of the present invention, the VT1 antiserum was demonstrated to cross-react with the VT2 protein.

From Coomassie gel staining it was estimated that 50% of the pMalVT1A elution and 10% of the pMalVT2A(BamHI) elution is full length fusion protein. This corresponds to 11 mg/liter (VT1 A) or 1.25 mg/l (VT2 A) yields of full length verotoxin subunit using these expression systems and embodiments.

II. Antibodies Directed Against E. coli and Associated Toxins

A preferred embodiment of the method of the present invention is directed toward obtaining antibodies against various E. coli serotypes, their toxins, enzymes or other metabolic by-products, cell wall components, or synthetic or recombinant versions of any of these compounds. It is contemplated that these antibodies will be produced by immunization of humans or other animals. It is not intended that the present invention be limited to any particular toxin or any species of organism. In one embodiment, toxins from all E. coli serotypes are contemplated as immunogens. Examples of these toxins include the verotoxins VT1 and VT2.

A. Antibodies Against the A and B Subunits

As the N-terminal of both the A and B subunits are exposed, it was contemplated that these structures may be targets for neutralizing immune responses. Boyd et al. (Boyd et al., Infect. Immun., 59:750–757 [1991]) reported that polyclonal antibodies raised against the B chain of VT-1/Shiga toxin neutralized cytotoxicity or lethality in animal models. However, success has not been consistently achieved. While polyclonal antibodies against synthetic peptides of intervals 28–40 of the B subunit of VT1 neutralized cytotoxicity, while polyclonal antibodies directed against intervals 1–25 and 53–69 recognized only denatured forms of the B chain and failed to neutralize cytotoxicity (Boyd et al., Infect. Immun. 59, 750–757 [1991]). In general, neutralization of toxicity and in vivo protection have been observed with antibodies directed against both the A and B chains of shiga toxin or VT1. However, most analysis has implicated the B chain as the best target for the generation of neutralizing antibodies and, in general, neutralizing titers are highest when conformationally correct B subunit is used as immunogen, rather than linear peptides (Boyd et al, 1991, Infect. Immun. 59, 750–757). Although an understanding of precise mechanisms is not necessary for the successful practice of the present invention, it is contemplated that in order to obtain maximally neutralizing antibodies, raising and testing (e.g., neutralization) polyclonal antibodies specific to both the A and B chain, relative to antibodies raised against holotoxin. Furthermore, in order to generate a high titer of neutralizing antibodies, the recombinant A and B chains should be conformationally correct.

In one embodiment of the present invention, laying Leghorn hens were immunized with the recombinant verotoxin subunits hisVT1B, hisVT2B, pMalVT1A and pMalVT2A (BamHI). Following three or more immunizations, IgY was purified from egg yolks by PEG fractionation. Specific antibody response was detected by ELISA, using microtiter plates coated with VT1 or VT2 holotoxin, IgY as primary antibody and alkaline phosphatase: anti-IgY as the secondary antibody. The validity of each ELISA assay was demonstrated with a positive control using rVT IgY and negative controls using Preimmune (PI) IgY.

These results for this embodiment showed relatively strong binding of VT1A-G IgY and VT1A-Q IgY to the homologous toxin rVT1, with titers of 1:6000 and 1:1200 respectively. However, there was essentially no cross reactivity of VT2A-G IgY and VT2A-Q IgY to VT1 holotoxin. VT1A-G IgY and VT1A-Q IgY cross reacted strongly to rVT2; both gave a titer of 1:6000 against rVT2. However, the signal from VT1A-Q IgY was much stronger at the higher concentrations. In contrast, homologous VT2A-Q IgY reactivity to rVT2 gave a much weaker response with a titer of 1:250 and VT2A-G IgY did not react over PI levels.

For VT1B, significant binding of, VT1B-Q IgY and VT1B-G to VT1 holotoxin with titers of 1:2500 and 1:500, respectively was observed. The binding of VT1B-G IgY and VT1B-Q IgY to rVT1 was similar with titers of 1:500 each. Heterologous VT2B-G IgY bound poorly with a titer of 1:100 while VT2B-Q IgY had a high titer of 1:1:2500 to rVT1. There was moderate cross-reactivity of VT1B-G IgY and VT1 B-Q IgY to VT2, with both giving titers of 1:500 and 2500, respectively. In addition, strong reactivity with a titer of 2500 was seen using homologous VT2B-Q IgY to VT2, while VT2B-G IgY showed no significant binding at 1:100.

Overall, these results indicated that the anti-VT1A, anti-VT1B and anti-VT2B of the present invention react with both VT1 and VT2 (i.e., they cross react). However, anti-VT2A reacts only with VT2 holotoxin.

B. Use of Antibodies

It is not intended that antibodies produced against one toxin will only be used against that toxin. It is contemplated that antibodies directed against one toxin may be used as an effective therapeutic against one or more toxin(s) produced by other *E. coli* serotypes, or other toxin producing organisms (e.g., Shigella, *Bacillus cereus, Staphylococcus aureus, Streptococcus mutans, Acinetobacter calcoaceticus, Pseudomonas aeruginosa,* other *Pseudomonas species, Vibrio species, Clostridium species,* etc.). It is further contemplated that antibodies directed against the portion of the toxin which binds to mammalian membranes can also be used against other organisms. It is contemplated that these membrane binding domains are produced synthetically and used as immunogens.

III. Obtaining Antibodies From Non-Mammals

A preferred embodiment of the method of the present invention for obtaining antibodies involves immunization. However, it is also contemplated that antibodies may be obtained from non-mammals without immunization. In the case where no immunization is contemplated, the present invention may use non-mammals with preexisting antibodies to toxins as well as non-mammals that have antibodies to whole organisms by virtue of reactions with the administered antigen. An example of the latter involves immunization with synthetic peptides or recombinant proteins sharing epitopes with whole organism components.

In a preferred embodiment, the method of the present invention contemplates immunizing non-mammals with bacterial toxin(s). It is not intended that the present invention be limited to any particular toxin. In one embodiment, toxins from all *E. coli* serotypes are contemplated as immunogens.

A particularly preferred embodiment involves the use of bacterial toxin protein or fragments of toxin proteins produced by molecular biological means (i.e., recombinant toxin proteins). In a preferred embodiment, the immunogen comprises recombinant VT1 and/or VT2.

When immunization is used, the preferred non-mammal is from the class Aves. All birds are contemplated (e.g., duck, ostrich, emu, turkey, etc.). A preferred bird is a chicken. Importantly, chicken antibody does not fix mammalian complement (See H. N. Benson et al., J. Immunol. 87:616 [1961]). Thus, chicken antibody will normally not cause a complement-dependent reaction (A. A. Benedict and K. Yamaga, "Immunoglobulins and Antibody Production in Avian Species," in *Comparative Immunology* (J. J. Marchaloni, ed.), pp. 335–375, Blackwell, Oxford [1966]). Thus, the preferred antitoxins of the present invention will not exhibit complement-related side effects observed with antitoxins presently known.

When birds are used, it is contemplated that the antibody will be obtained from either the bird serum or the egg. A preferred embodiment involves collection of the antibody from the egg. Laying hens transport immunoglobulin to the egg yolk ("IgY") in concentrations equal to or exceeding that found in serum (See R. Patterson et al., J. Immunol. 89:272 (1962); and S. B. Carroll and B. D. Stollar, J. Biol. Chem. 258:24 [1983]). In addition, the large volume of egg yolk produced vastly exceeds the volume of serum that can be safely obtained from the bird over any given time period. Finally, the antibody from eggs is more pure and more homogeneous; there is far less non-immunoglobulin protein (as compared to serum) and only one class of immunoglobulin is transported to the yolk.

When considering immunization with toxins, one may consider modification of the toxins to reduce the toxicity. In this regard, it is not intended that the present invention be limited by immunization with modified toxin. Unmodified ("native") toxin is also contemplated as an immunogen.

It is also not intended that the present invention be limited by the type of modification—if modification is used. The present invention contemplates all types of toxin modification, including chemical and heat treatment of the toxin. In one embodiment, glutaraldehyde treatment of the toxin is contemplated. In an alternative embodiment, formaldehyde treatment of the toxin is contemplated.

It is not intended that the present invention be limited to a particular mode of immunization; the present invention contemplates all modes of immunization, including subcutaneous, intramuscular, intraperitoneal, and intravenous or intravascular injection, as well as per os administration of immunogen.

The present invention further contemplates immunization with or without adjuvant. As used herein, the term "adjuvant" is defined as a substance known to increase the immune response to other antigens when administered with other antigens. If adjuvant is used, it is not intended that the present invention be limited to any particular type of adjuvant—or that the same adjuvant, once used, be used all the time. While the present invention contemplates all types of adjuvant, whether used separately or in combinations, the preferred use of adjuvant is the use of Complete Freund's Adjuvant followed sometime later with Incomplete Freund's Adjuvant. The invention also contemplates the use of fowl adjuvant commercially available from RIBI, as well as Quil A adjuvant commercially available from Accurate Chemical and Scientific Corporation, and Gerbu adjuvant also commercially available (GmDP; C.C. Biotech Corp.).

When immunization is used, the present invention contemplates a wide variety of immunization schedules. In one embodiment, a chicken is administered toxin(s) on day zero and subsequently receives toxin(s) in intervals thereafter. It is not intended that the present invention be limited by the particular intervals or doses. Similarly, it is not intended that the present invention be limited to any particular schedule for collecting antibody. The preferred collection time is sometime after day 35.

Where birds are used and collection of antibody is performed by collecting eggs, the eggs may be stored prior to processing for antibody. It is preferred that eggs be stored at 4° C. for less than one year.

It is contemplated that chicken antibody produced in this manner can be buffer-extracted and used analytically. While unpurified, this preparation can serve as a reference for activity of the antibody prior to further manipulations (e.g., immunoaffinity purification).

IV. Increasing The Effectiveness Of Antibodies

When purification is used, the present invention contemplates purifying to increase the effectiveness of both non-mammalian antitoxins and mammalian antitoxins. Specifically, the present invention contemplates increasing the percent of toxin-reactive immunoglobulin. The preferred purification approach for avian antibody is polyethylene glycol (PEG) separation.

The present invention contemplates that avian antibody be initially purified using simple, inexpensive procedures. In one embodiment, chicken antibody from eggs is purified by extraction and precipitation with PEG. PEG purification exploits the differential solubility of lipids (which are abundant in egg yolks) and yolk proteins in high concentrations of PEG 8000 (Polson et al., Immunol. Comm. 9:495 [1980]). The technique is rapid, simple, and relatively inexpensive and yields an immunoglobulin fraction that is significantly more pure, in terms of contaminating non-immunoglobulin proteins than the comparable ammonium sulfate fractions of mammalian sera and horse antibodies. The majority of the PEG is removed from the precipitated chicken immunoglobulin by treatment with ethanol. Indeed, PEG-purified antibody is sufficiently pure that the present invention contemplates the use of PEG-purified antitoxins in the passive immunization of intoxicated humans and animals.

V. Treatment

The present invention contemplates antitoxin therapy for humans and other animals intoxicated by bacterial toxins. A preferred method of treatment is by parenteral administration of antitoxin. In particularly preferred embodiments, IgY of the present invention, capable of neutralizing both VT1 and VT2 is used.

A. Dosage Of Antitoxin

It was noted by way of background that a balance must be struck when administering currently available antitoxin which is usually produced in large animals such as horses; sufficient antitoxin must be administered to neutralize the toxin, but not so much antitoxin as to increase the risk of untoward side effects. These side effects are caused by: i) patient sensitivity to foreign (e.g, horse) proteins; ii) anaphylactic or immunogenic properties of non-immunoglobulin proteins; iii) the complement fixing properties of mammalian antibodies; and/or iv) the overall burden of foreign protein administered. It is extremely difficult to strike this balance when, as noted above, the degree of intoxication (and hence the level of antitoxin therapy needed) can only be approximated.

The present invention contemplates significantly reducing side effects so that this balance is more easily achieved. Treatment according to the present invention contemplates reducing side effects by using PEG-purified antitoxin from birds.

In one embodiment, the treatment of the present invention contemplates the use of PEG-purified antitoxin from birds. The use of yolk-derived, PEG-purified antibody as antitoxin allows for the administration of: 1) non (mammalian)-complement-fixing, avian antibody; 2) a less heterogeneous mixture of non-immunoglobulin proteins; and 3) less total protein to deliver the equivalent weight of active antibody present in currently available antitoxins. The non-mammalian source of the antitoxin makes it useful for treating patients who are sensitive to horse or other mammalian sera.

As is true in cases of botulism, the degree of an individual's exposure to $E.\ coli$ toxin and the prognosis are often difficult to assess, and depend upon a number of factors (e.g., the quantity of contaminated food ingested, the toxigenicity and serotype of $E.\ coli$ strain ingested, etc.). Thus, the clinical presentation of a patient is usually a more important consideration than a quantitative diagnostic test, for determination of dosage in antitoxin administration. Indeed, for many toxin-associated diseases (e.g., botulism, tetanus, diphtheria, etc.), there is no rapid, quantitative test to detect the presence of the toxin or organism. Rather, these toxin-associated diseases are medical emergencies which mandate immediate treatment. Confirmation of the etiologic agent must not delay the institution of therapy, as the condition of an affected patient may rapidly deteriorate. In addition to the initial treatment with antitoxin, subsequent doses may be indicated, as the patient's disease progresses. The dosage and timing of these subsequent doses is dependent upon the signs and symptoms of disease in each individual patient.

It is contemplated that the administration of antitoxin to an affected individual would involve an initial injection of an approximately 10 ml dose of immune globulin (with less than approximately 1 gram of total protein). In one preferred embodiment, it is contemplated that at least 50% of the initial injection comprises immune globulin. It is also contemplated that more purified immune globulin be used for treatment, wherein approximately 90% of the initial injection comprises immune globulin. When more purified immune globulin is used, it is contemplated that the total protein will be less than approximately 100 milligrams. It is also contemplated that additional doses be given, depending upon the signs and symptoms associated with $E.\ coli$ verotoxin disease progression.

B. Delivery Of Antitoxin

Although it is not intended to limit the route of delivery, the present invention contemplates a method for antitoxin treatment of bacterial intoxication in which delivery of antitoxin is parenteral or oral.

In one embodiment, antitoxin is parenterally administered to a subject in an aqueous solution. It is not intended that the parenteral administration be limited to a particular route. Indeed, it is contemplated that all routes of parenteral administration will be used. In one embodiment, parenteral administration is accomplished via intramuscular injection. In an alternative embodiment, parenteral administration is accomplished via intravenous injection.

In another embodiment, antitoxin is delivered in a solid form (e.g., tablets). In an alternative embodiment antitoxin is delivered in an aqueous solution. When an aqueous solution is used, the solution has sufficient ionic strength to solubilize antibody protein, yet is made palatable for oral administration. The delivery solution may also be buffered (e.g., carbonate buffer, pH 9.5) which can neutralize stomach acids and stabilize the antibodies when the antibodies are administered orally. In one embodiment the delivery solution is an aqueous solution. In another embodiment the delivery solution is a nutritional formula. Preferably, the delivery solution is infant or a dietary supplement formula (e.g., Similac®, Ensure®, and Enfamil®). Yet another embodiment contemplates the delivery of lyophilized antibody encapsulated or microencapsulated inside acid-resistant compounds.

Methods of applying enteric coatings to pharmaceutical compounds are well known to the art (companies specializing in the coating of pharmaceutical compounds are available; for example, The Coating Place [Verona, Wis.] and AAI [Wilmington, N.C.]). Enteric coatings which are resistant to gastric fluid and whose release (i.e., dissolution of the coating to release the pharmaceutical compound) is pH dependent are commercially available (for example, the polymethacrylates Eudragit® L and Eudragit® S [Rohm Tech Inc., Malden, Mass.]). Eudragit® S is soluble in intestinal fluid from pH 7.0; this coating can be used to microencapsulate lyophilized antitoxin antibodies and the particles are suspended in a solution having a pH above or below pH 7.0 for oral administration. The microparticles will remain intact and undissolved until they reached the intestines where the intestinal pH would cause them to dissolve thereby releasing the antitoxin.

The invention contemplates a method of treatment which can be administered for treatment of acute intoxication. In one embodiment, antitoxin is administered orally in either a delivery solution or in tablet form, in therapeutic dosage, to a subject intoxicated by the bacterial toxin which served as immunogen for the antitoxin. In another embodiment of treatment of acute intoxication, a therapeutic dosage of the antitoxin in a delivery solution, is parenterally administered.

The invention also contemplates a method of treatment which can be administered prophylactically. In one embodiment, antitoxin is administered orally, in a delivery solution, in therapeutic dosage, to a subject, to prevent intoxication of the subject by the bacterial toxin which served as immunogen for the production of antitoxin. In another embodiment, antitoxin is administered orally in solid form such as tablets or as microencapsulated particles. Microencapsulation of lyophilized antibody using compounds such as Eudragit® (Rohm GmbH) or polyethylene glycol, which dissolve at a wide range of pH units, allows the oral administration of solid antitoxin in a liquid form (i.e., a suspension) to recipients unable to tolerate administration of tablets (e.g., children or patients on feeding tubes). In one preferred embodiment the subject is a child. In another embodiment, antibody raised against whole bacterial organism is administered orally to a subject, in a delivery solution, in therapeutic dosage. In yet another preferred embodiment of prophylactic treatment, a therapeutic dosage of the antitoxin in a delivery solution, is parenterally administered.

VI. Multivalent Vaccines Against *E. coli* Strains

The invention contemplates the generation of multivalent vaccines for the protection of an organism (particularly humans) against several *E. coli* strains. Of particular interest is a vaccine which stimulates the production of a humoral immune response to *E. coli* O157:H7, O26:H11, O113:H21, O91:H21, and O111:NM, in humans. The antigens comprising the vaccine preparation may be native or recombinantly produced toxin proteins from the *E. coli* serotypes listed above. When native toxin proteins are used as immunogens they are generally modified to reduce the toxicity. It is contemplated that glutaraldehyde-modified toxin proteins will be used. In an alternative embodiment, is formaldehyde-modified toxin proteins will be used.

The invention contemplates that recombinant *E. coli* verotoxin proteins be used in conjunction with either native toxins or toxoids from other organisms as antigens in a multivalent vaccine preparation. It is also contemplated that recombinant *E. coli* toxin proteins be used in the multivalent vaccine preparation.

VII. Detection Of Toxin

The invention contemplates detecting bacterial toxin in a sample. The term "sample" in the present specification and claims is used in its broadest sense. On the one hand it is meant to include a specimen or culture (e.g., microbiological cultures). On the other hand, it is meant to include both biological and environmental samples.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of common domestic animals, including but not limited, to bovines (e.g, cattle), ovines (e.g., sheep), caprines (e.g., goats), porcines (e.g., swine), equines (e.g., horses), canines (e.g., dogs), felines (e.g., cats), lagamorphs (e.g., rabbits), aves (e.g., chickens, ducks, geese, etc.), and rodents (e.g., mice), etc. It is also intended that samples may be obtained from feral or wild animals, including, but not limited to, such animals as ungulates (e.g., deer), bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The invention contemplates detecting bacterial toxin by a competitive immunoassay method that utilizes recombinant toxin VT1 and toxin VT2 proteins, antibodies raised against recombinant bacterial toxin proteins. A fixed amount of the recombinant toxin proteins are immobilized to a solid support (e.g., a microtiter plate) followed by the addition of a biological sample suspected of containing a bacterial toxin. The biological sample is first mixed with affinity-purified or PEG fractionated antibodies directed against the recombinant toxin protein. A reporter reagent is then added which is capable of detecting the presence of antibody bound to the immobilized toxin protein. The reporter substance may comprise an antibody with binding specificity for the antitoxin attached to a molecule which is used to identify the presence of the reporter substance. If toxin is present in the sample, this toxin will compete with the immobilized recombinant toxin protein for binding to the anti-recombinant antibody thereby reducing the signal obtained following the addition of the reporter reagent. A control is employed where the antibody is not mixed with the sample. This gives the highest (or reference) signal.

The invention also contemplates detecting bacterial toxin by a "sandwich" immunoassay method that utilizes antibodies directed against recombinant bacterial toxin proteins. Affinity-purified antibodies directed against recombinant bacterial toxin proteins are immobilized to a solid support (e.g., microtiter plates). Biological samples suspected of containing bacterial toxins are then added followed by a washing step to remove substantially all unbound antitoxin. The biological sample is next exposed to the reporter substance, which binds to antitoxin and is then washed free of substantially all unbound reporter substance. The reporter substance may comprise an antibody with binding specificity for the antitoxin attached to a molecule which is used to identify the presence of the reporter substance. Identification of the reporter substance in the biological tissue indicates the presence of the bacterial toxin.

It is also contemplated that bacterial toxin be detected by pouring liquids (e.g., soups and other fluid foods and feeds including nutritional supplements for humans and other animals) over immobilized antibody which is directed against the bacterial toxin. It is contemplated that the immobilized antibody will be present in or on such supports as cartridges, columns, beads, or any other solid support medium. In one embodiment, following the exposure of the liquid to the immobilized antibody, unbound toxin is substantially removed by washing. The liquid is then exposed to a reporter substance which detects the presence of bound toxin. In a preferred embodiment the reporter substance is an enzyme, fluorescent dye, or radioactive compound attached to an antibody which is directed against the toxin (i.e., in a "sandwich" immunoassay). It is also contemplated that the detection system will be developed as necessary (e.g., the addition of enzyme substrate in enzyme systems; observation using fluorescent light for fluorescent dye systems; and quantitation of radioactivity for radioactive systems).

EXPERIMENTAL

The following examples serve to illustrate certain preferred embodiments and aspects of the present invention and are not to be construed as limiting the scope thereof.

In the disclosure which follows, the following abbreviations apply: rVT (recombinant verotoxin); °C. (degrees Centigrade); rpm (revolutions per minute); BSA (bovine serum albumin); ELISA (enzyme-linked immunosorbent assay); Ig (immunoglobulin); IgG (immunoglobulin G); IgY (immunoglobulin Y); IP (intraperitoneal); SC (subcutaneous); $H_2O$ (water); HCl (hydrochloric acid); $LD_{100}$ (lethal dose for 100% of experimental animals); $LD_{50}$ (lethal dose for 50% of experimental animals); EU (endotoxin unit); aa (amino acid); HPLC (high performance liquid chromatography); Kda and kd (kilodaltons); gm and g (grams); $\mu$g (micrograms); mg (milligrams); ng (nanograms); $\mu$l (microliters); ml (milliliters); l (liter); mm (millimeters); nm (nanometers); $\mu$m (micrometer); xg and x g (times gravity); M (molar); mM (millimolar); MW (molecular weight); sec (seconds); min(s) (minute/minutes); hr(s) (hour/hours); $MgCl_2$ (magnesium chloride); NaCl (sodium chloride); $Na_2CO_3$ (sodium carbonate); $OD_{280}$ (optical density at 280 nm); $OD_{600}$ (optical density at 600 nm); PAGE (polyacrylamide gel electrophoresis); SDS-PAGE (sodium dodecyl sulfate polyacrylamide gel electrophoresis); plysS and plysE (genes encoding T7 lysozyme); IDA (iminodiacetic acid) resin; PBS (phosphate buffered saline [150 mM NaCl, 10 mM sodium phosphate buffer, pH 7.2]); PEG (polyethylene glycol); SDS (sodium dodecyl sulfate); Tris (tris(hydroxymethyl)aminomethane); w/v (weight to volume); v/v (volume to volume); Amicon (Amicon, Inc., Beverly, Mass.); Amresco (Amresco, Inc., Solon, Ohio); ATCC (American Type Culture Collection, Rockville, Md.); BBL (Baltimore Biologics Laboratory, (a division of Becton Dickinson), Cockeysville, Md.); Becton Dickinson (Becton Dickinson Labware, Lincoln Park, N.J.); BioRad (BioRad, Richmond, Calif.); Biotech (C-C Biotech Corp., Poway, Calif.); Charles River (Charles River Laboratories, Wilmington, Mass.); Falcon (e.g., Baxter Healthcare Corp., McGaw Park, Ill. and Becton Dickinson); Fisher Biotech (Fisher Biotech, Springfield, N.J.); GIBCO (Grand Island Biologic Company/BRL, Grand Island, N.Y.); Mallinckrodt (a division of Baxter Healthcare Corp., McGaw Park, Ill.); Millipore (Millipore Corp., Marlborough, Mass.); New England Biolabs (New England Biolabs, Inc., Beverly, Mass.); Novagen (Novagen, Inc., Madison, Wis.); Pharmacia (Pharmacia, Inc., Piscataway, N.J.); Qiagen (Qiagen, Chatsworth, Calif.); Showdex (Showa Denko America, Inc., New York, N.Y.); Sigma (Sigma Chemical Co., St. Louis, Mo.); RIBI (RIBI Immunochemical Research Inc., Hamilton, Mont.); Accurate Chemical and Scientific Corp. (Accurate Chemical and Scientific Corp., Hicksville, N.Y.); Kodak (Eastman-Kodak, Rochester, N.Y.); and Sterogene (Sterogene Bioseparations, Inc., Carlsbad, Calif.); and Stratagene (Stratagene, La Jolla, Calif.).

When a recombinant protein is described in the specification it is referred to in a short-hand manner by the amino acids in the toxin sequence present in the recombinant protein rounded to the nearest 10. The specification gives detailed construction details for all recombinant proteins such that one skilled in the art will know precisely which amino acids are present in a given recombinant protein.

The first set of Examples (Examples 1–5) was designed to develop an antidote to E. coli O157:H7 verotoxins and evaluate its effectiveness in vitro and in vivo. In the first experiments, high titer verotoxin antibodies were generated in laying hens hyperimmunized with chemically detoxified and/or native verotoxins. These Laying hens were immunized with either recombinant E. coli O157:H7 VT1 or VT2 (rVT1 and rVT2) treated with glutaraldehyde and mixed with adjuvant.

Next, toxin-reactive polyclonal antibodies were isolated by bulk fractionation from egg yolks pooled from hyperimmunized hens. Large quantities of polyclonal antibodies (IgY) were harvested from resulting eggs using a two-step polyethylene glycol fractionation procedure.

Third, the immunoreactivity and yields of VT IgY were analyzed by analytical immunochemical methods (e.g., enzyme immunoassay (EIA) and Western blotting). EIA and Western blot analysis showed that the resulting egg preparations contained high titer IgY that reacted with both the immunizing and the heterologous toxins (i.e., rVT1 IgY reacted against both rVT1 and rVT2, and vice versa).

Fourth, VT neutralization potency was analyzed in vitro using a Vero cytotoxicity assay. Vero cytotoxicity of rVT1 and rVT2 could be completely inhibited by VT IgY. These antibodies also demonstrated substantial verotoxin cross-neutralization.

Fifth, the efficacy of passively administered avian verotoxin antibodies in preventing the lethal effects of verotoxin poisoning was assessed in a mouse disease model. Toxin neutralizing antibodies were administered by parenteral dosing regimens to assess the most effective strategy for therapeutic intervention. Efficacy of verotoxin antibodies was demonstrated using multiple murine disease models. In these experiments, antibodies prevented both the morbidity and lethality of homologous and heterologous toxins using a toxin/antitoxin premix format; mice infected orally with a lethal dose of viable *E. coli* O157:H7 were protected from both morbidity and lethality when treated parenterally four hours post-infection with either rVT1 or rVT2 antibodies; and mice given a lethal dose of *E. coli* O91:H21 (a particularly virulent strain which only produces VT2c, a VT2 structural variant) and treated parenterally up to 10 hours later with rVT1 IgY administered parenterally were protected from both morbidity and lethality.

Sixth, verotoxin clones were constructed and expressed, including His-tagged and MBP fusions, as well as vectors for expression of VT1B and VT2B subunits without His-tags. Next, fermentation cultures (i.e., large scale preparations) of the expressed VT2B protein were produced. The expressed verotoxin subunits were used as immunogens in hens and rabbits, the titers determined by quantitative ELISA methods developed as described in the following examples. Finally, the protective ability of the rabbit and chicken IgY antisera were tested in in vivo challenges in mice.

EXAMPLE 1

Toxin Analysis and Immunization

Purified recombinant *E. coli* O157:H7 verotoxins, rVT1 and rVT2, were obtained from Denka Sieken Co., Ltd. (Tokyo, Japan). Recombinant proteins were then purified by ammonium sulfate precipitation, ion exchange chromatography on DEAE Sephacryl and hydroxyapatite, and gel filtration chromatography by the supplier. Toxin genes were isolated, inserted into expression plasmids, and expressed in *E. coli.* Upon receipt, toxins were analyzed to verify identity, purity and toxicity, as described below.

A. Sodium Dodecyl Sulfate Polyacrylamide Gel Electrophoresis (SDS-PAGE).

Samples of each toxin (2 μg) were heat-denatured in a buffer containing SDS and β-mercaptoethanol followed by electrophoresis on 4–20% gradient gels (Bio-Rad, Richmond, Calif.). Resolved polypeptide bands were visualized using the silver stain procedure of C. R. Merril, et al., "Ultrasensitive stain for proteins in polyacrylamide gels shows regional variation in cerebrospinal fluid proteins," Science 211: 1437–1438 (1981).

VT1 and VT2 are each composed of subunit A and multiple copies of subunit B. Subunit A is often nicked into fragments A1 and A2 which are linked by a disulfide bridge. As shown in FIG. 1, when separated by SDS-PAGE in the presence of β-mercaptoethanol, rVT1 resolved into 3 bands that corresponded to subunit A (~31 Kda), fragment A1 (~27 Kda) and a mixture of subunit B and fragment A2 (4 Kda). Similarly, rVT2 resolved into subunit A (~33 Kda), fragment A1 (~27 Kda) and a mixture of subunit B and fragment A2 (~8 Kda) (FIG. 1). In this Figure, rVT1 is in lane 1, and rVT2 is in lane 2; the positions of molecular weight markers (Kda) are shown at the left. rVT component polypeptides are identified at the right.

These results are consistent with previous reports of VT1 and VT2 purified from naturally occurring toxigenic strains (V. V. Padhye et al., "Purification and Physicochemical Properties of a Unique Vero Cell Cytotoxin From *Escherichia coli* O157:H7," Biochem. Biophys. Res. Commun., 139: 424–430 [1986]; and F. B. Kittel et al., "Characterization and inactivation of verotoxin 1 produced by *Escherichia coli* O157:H7," J. Agr. Food Chem., 39: 141–145 [1991]).

B. High Performance Liquid Chromatography (HPLC).

Chromatography was performed at room temperature (RT) under isocratic conditions using a Waters 510 HPLC pump. Eluted protein was measured using a Waters 490E programmable multi-wavelength detector (Millipore Corp., Milford, Mass.). The VT's were separated on an 8×300 mm (ID) Shodex KW803 column, using 10 mM sodium phosphate, 0.15 M NaCl, pH 7.4 (PBS) as the mobile phase at a flow rate of 1 ml/min.

The purity of non-denatured rVT's was assessed by HPLC. As shown in the chromatographs in FIG. 2, each toxin eluted at approximately 10 min. as a single absorbance peak at 280 nm. In this Figure, Panel A shows the HPLC results for rVT1, and Panel B shows the HPLC results for rVT2. By integration of the area under each peak, the rVT's were shown to be >99% pure.

C. Vero Cell Cytotoxicity Assay.

Cytotoxic activity of rVT1 and rVT2 was assessed using modified procedures of Padhye, et al. (V. V. Padhye et al., "Purification and Physicochemical Properties of a Unique Vero Cell Cytotoxin From *Escherichia coli* O157:H7," Biochem. Biophys. Res. Commun., 139: 424–430 [1986]), and McGee, et al., (Z. A. McGee, et al., "Local induction of tumor necrosis factor as molecular mechanism of mucosal damage by gonococci," Microbial Pathogenesis 12: 333–341 [1992]). Microtiter plates (96 well, Falcon, Microtest III) were inoculated with approximately $1\times10^4$ Vero cells (ATCC, CCL81) per well (100 μl) and incubated overnight at 37° C. in the presence of 5% $CO_2$ to form Vero cell monolayers. rVT1 and rVT2 solutions were serially diluted in Medium 199 supplemented with 5% fetal bovine serum (Life Technologies, Grand Island, N.Y.), added to each well of the microtiter plates and incubated at 37° C. for 18–24 hrs. Adherent (viable) cells were stained with 0.2% crystal violet (Mallinckrodt) in 2% ethanol. Excess stain was rinsed away and the stained cells were solubilized by adding 100 μl of 1% SDS to each well. Absorbance of each well was measured at 570 nm, and the percent cytotoxicity of each test sample was calculated using the following formula:

$$\%\ \text{Vero Cytotoxicity}=[1-(\text{Absorbance Sample}/\text{Absorbance Control})]\times 100$$

To determine whether the rVT's possessed potency equivalent to published cytotoxicity values, a Vero cell cytotoxicity assay was performed (FIG. 3). Between 0.01–10,000 pg of either rVT1 or rVT2 was added to Vero cells. The amounts of rVT causing 50% cell death ($CD_{50}$), as calculated by second degree polynomial curve fitting were 0.97 pg and 1.5 pg, for rVT1 and rVT2, respectively. These results are consistent with $CD_{50}$ values reported previously for naturally occurring VT1 and VT2 in the range 1–35 pg and 1–25 pg, respectively (M. Petric et al., Purification and biological properties of *Escherichia coli* verocytotoxin," FEMS Microbiol. Lett., 41: 63–68 [1987]; V. L. Tesh, et al., "Comparison of relative toxicities of Shiga-Like toxins Type I and Type II for mice," Infect. Immun., 61: 3392–3402 [1993]; N. Dickie et al., "Purification of an *Escherichia coli* Serogroup O157:H7 verotoxin and its detection in North American hemorrhagic colitis isolates," J. Clin. Microbiol., 27: 1973–1978 [1989]; and U. Kongmuang, et al., "A simple method for purification of Shiga or Shiga-Like toxin from *Shigella dysenteriae* and *Escherichia coli* O157:H7 by immunoaffinity chromatography," FEMS Microbiol. Lett., 48: 379–383 [1987]). It has been observed that toxicity is lost with storage, explaining why higher amounts of toxin were used in the neutralization assays described below.

D. Mouse Lethal Dose Determination.

To verify rVT1 and rVT2 toxicity, male (20–22 g) CD-1 mice were injected intraperitoneally with varying amounts of rVT1 or rVT2 in 200 µL phosphate buffer. Doses were selected based on published $LD_{50}$ values for VT1 and VT2 in CD-1 mice. To minimize the sacrifice of live animals, a full statistical toxin $LD_{50}$ was not determined. Mice were observed for morbidity and mortality over 7-day period.

Further confirmation of rVT toxicity was obtained from mouse lethality experiments (Tables 2 and 3). Mice were injected intraperitoneally with varying amounts of either rVT1 or rVT2 and observed 7 days for mortality. Within 72–120 hrs. post-injection, all of the mice died from 100 ng of rVT1 or 10 ng of rVT2, respectively. This lethality study served as a verification of expected toxicity but not as a statistical determination of $LD_{50}$. Nonetheless, these results were consistent with toxicity studies which reported $LD_{50}$ values in CD-1 mice of 0.4–2.0 µg for purified VT1 and 0.001–1.0 µg for purified VT2 (V. L. Tesh, et al., "Comparison of relative toxicities of Shiga-Like toxins Type I and Type II for mice," Infect. Immun., 61: 3392–3402 [1993]; and A. D. O'Brien, and G. D. LaVeck, "Purification and characterization of *Shigella dysenteriae* 1-like toxin produced by *Escherichia coli*," Infect. Immun. 40: 675–683 [1983]).

TABLE 2

Lethality of rVT1 in CD-1 Mice

| ng VT1 Injected | Survivors/Total | Hours Post-Injection |
| --- | --- | --- |
| 100 | 7/7 | 24 ± 2 |
|  | 5/7 | 48 ± 2 |
|  | 0/7 | 72 ± 2 |
| 10 | 7/7 | 24 ± 2 |
|  | 7/7 | 48 ± 2 |
|  | 7/7 | 72 ± 2 |
| 1.0 | 6/6 | 24 ± 2 |
|  | 6/6 | 48 ± 2 |
|  | 6/6 | 72 ± 2 |

TABLE 3

Lethality of rVT2 in CD-1 Mice

| ng VT2 Injected | Survivors/Total | Hours Post-Injection |
| --- | --- | --- |
| 10 | 3/6 | 48 ± 2 |
|  | 2/6 | 72 ± 2 |
|  | 0/6 | 120 ± 2 |
| 1.0 | 5/6 | 48 ± 2 |
|  | 4/6 | 72 ± 2 |
|  | 0/6 | 120 ± 2 |
| 0.1 | 6/6 | 48 ± 2 |
|  | 6/6 | 72 ± 2 |
|  | 6/6 | 120 ± 2 |

The recombinant toxins used in these studies thus appeared to contain protein components and toxicities consistent with literature reports for native toxins. Based on these structural and functional analyses, the rVT's were considered suitable as antigens to generate specific avian antibodies.

E. Antigen Preparation.

Lyophilized samples, rVT1 and rVT2 were received and each was reconstituted with 2.5 mL of deionized water to a final concentration of 100 µg/ml in phosphate buffer. To form a toxoid, the solutions were then treated with 0.4% glutaraldehyde (Mallinckrodt) at 4° C. overnight and stored at −20° C. thereafter. When needed, toxoid was thawed and mixed 5:1 (volume:volume) with 5 µg GERBU adjuvant (C. C. Biotech Corporation, Poway, Calif.). White Leghorn laying hens were injected subcutaneously with 25 µg of either rVT1 or rVT2 toxoid in adjuvant at 2–3 week intervals.

EXAMPLE 2

PEG Extraction of Egg Yolk Antibody

Hyperimmune eggs were collected after 3 immunizations with toxoid. Egg yolks were separated from whites, pooled according to their immunogen group and blended with 4 volumes of 10 mM sodium phosphate, 150 mM NaCl, pH 7.4 (PBS). Polyethylene glycol 8000 (PEG) (Amresco, Solon, Ohio) was then added to a final concentration of 3.5% and the mixture centrifuged at 10,000 x g for 10 min. to remove the precipitated lipid fraction. IgY-rich supernatant was filtered through cheesecloth and PEG was again added to a final concentration of 12%. The solution was centrifuged as above and the resulting supernatant discarded. The IgY pellet was then dissolved in PBS to either the original (1X PEG IgY) or ¼ of the original (4X PEG IgY) yolk volume, filtered through a 0.45µ membrane and stored at 4° C.

EXAMPLE 3

Antitoxin Immunoassays

A. Enzyme Immunoassay (EIA).

EIA was used to monitor antibody responses during the immunization course. Wells of 96-well Pro-Bind microtiter plates (Falcon, through Scientific Products, McGaw Park, Ill.) were each coated overnight with 100 µl of PBS containing 1 µg/ml rVT's (not toxoid) at 2–8° C. Wells were washed 3 times with PBS containing 0.05% Tween-20 (PBS-T) to remove unbound antigen, and the remaining protein binding sites were blocked with PBS containing 5 mg/ml BSA for 60 min. at 37° C. IgY, diluted in PBS containing 1 mg/ml BSA and 0.05% Tween-20 was then added to the wells and incubated for 1 hr. at 37° C. Wells were washed as before to remove unbound primary antibody and incubated for 1 hr. at 37° C. with alkaline phosphatase-conjugated rabbit-anti-chicken IgG (Sigma Chemical Company, St. Louis, Mo.) diluted 1:1000 in PBS-T. Wells were again washed and 1 mg/ml p-nitrophenyl phosphate (Sigma Chemical Company, St. Louis, Mo.) in 50 mM $Na_2CO_3$, 10 mM $MgCl_2$, pH 9.5 was added and allowed to incubate at RT. Phosphatase activity was detected by absorbance at 410 nm using a Dynatech MR700 microtiter plate reader.

Figure 2A:
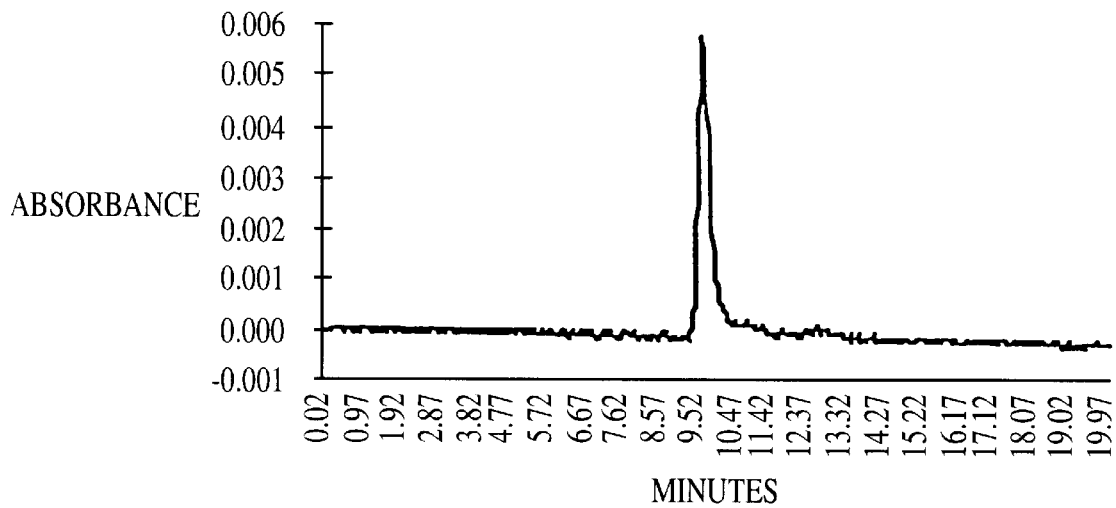
FIG. 2 shows HPLC results for rVT1 and rVT2.
Figure 2B:
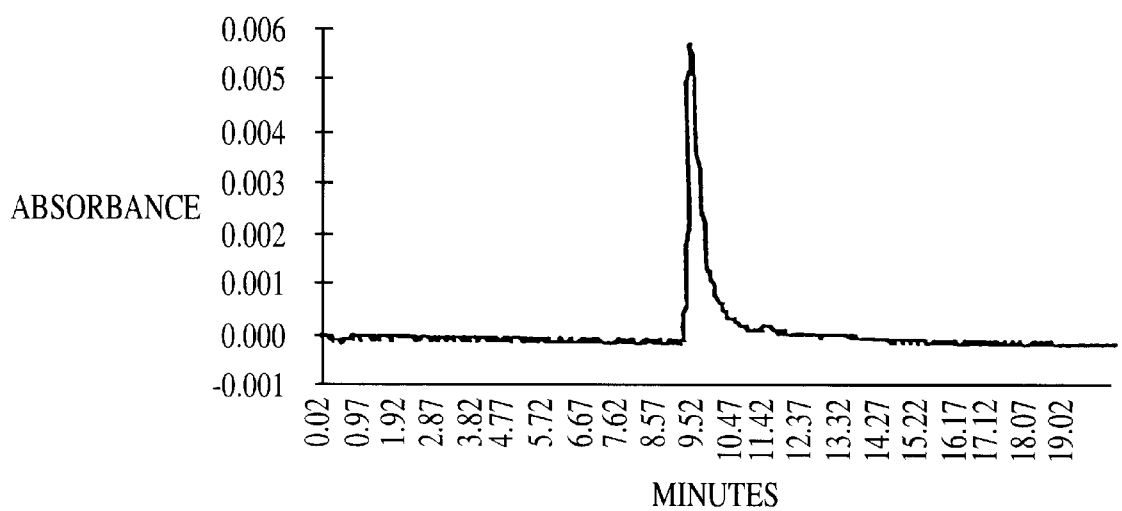
Figure 4:
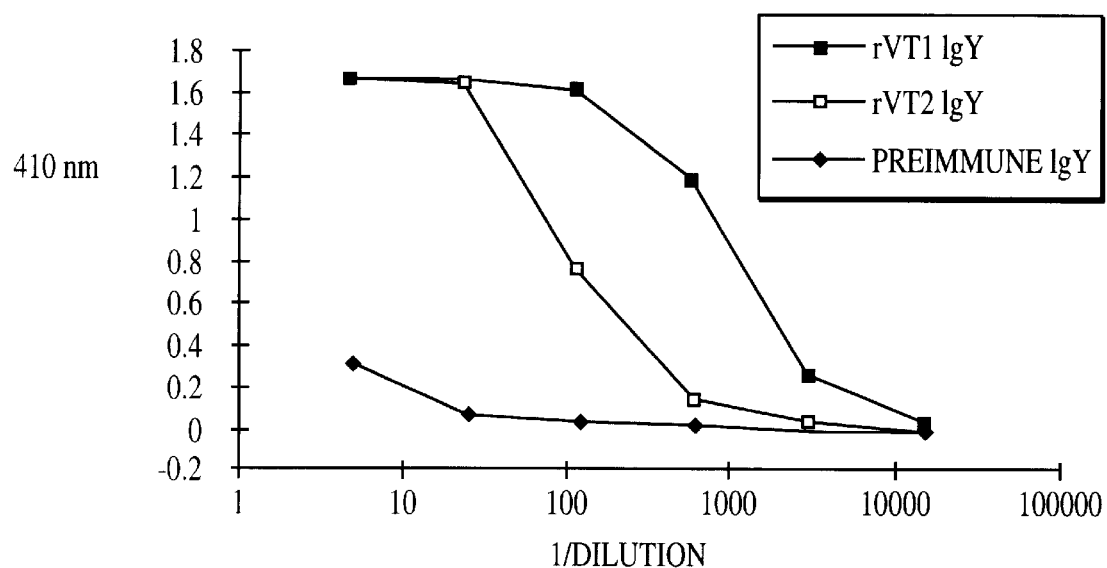
FIG. 4 shows ELISA reactivity of rVT1 and rVT2 antibodies to rVT1.
Figure 5:
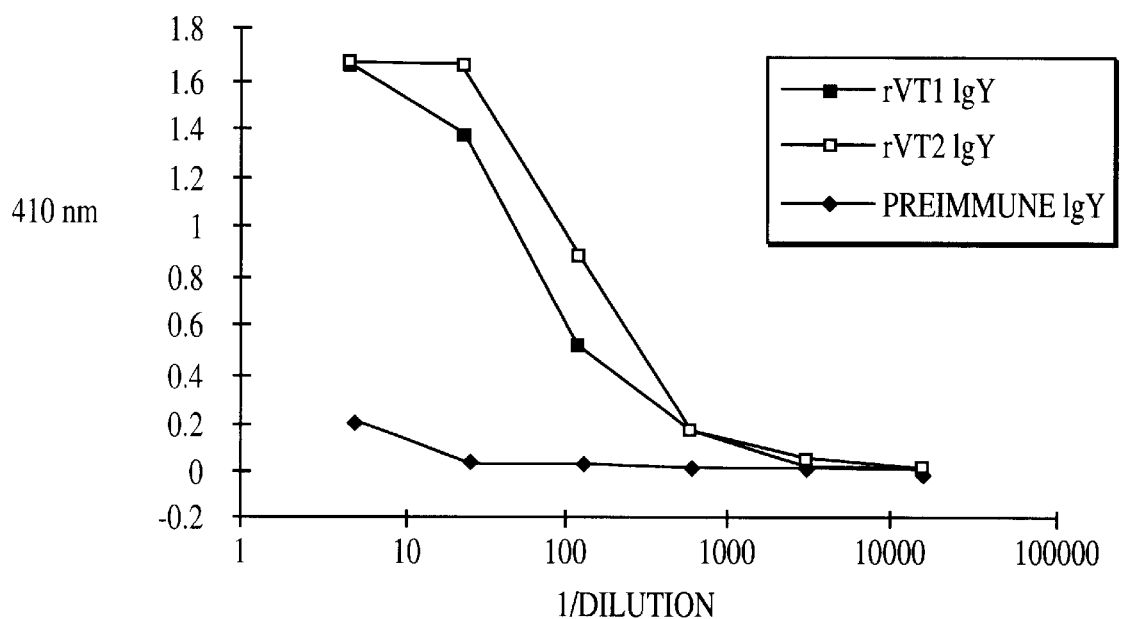
FIG. 5 shows ELISA reactivity of rVT1 and rVT2 Antibodies to rVT2.

Laying Leghorn hens were immunized as described above (Example 1, part E), using glutaraldehyde-treated rVT's. Following several immunizations, eggs were collected and IgY harvested by PEG fractionation. FIGS. 4 and 5 show rVT1 or rVT2 specific antibody responses detected using EIA at dilutions of the original yolk IgY concentration of 1:30,000 and 1:6,000, respectively. IgY fractionated similarly from unimmunized hens (i.e., preimmune antibody) did not react with either antigen at test dilutions above 1:50. Although these EIA results indicate significant antibody responses, prior experience with other toxin antigens has shown that optimization of immunization regimens, including increasing the amount of antigen, can yield titers in excess of 1:100,000 (B. S. Thalley, et al.,"Development of an Avian Antitoxin to Type A Botulinum Neurotoxin," in *Botulinum and Tetanus Neurotoxins: Neurotransmission and Biomedical Aspects*, B. R. DasGupta, (ed.) [Plenum Press, New York, 1993] pp. 467–472). As may be expected due to their structural homology and consistent with previous reports (e.g., V. V. Padhye et al., "Production and characterization of monoclonal antibodies to verotoxins 1 and 2 from *Escherichia coli* O157:H7," *J. Agr. Food Chem.*, 39: 141–145 [1989]; S. C. Head et al., "Purification and characterization of verocytotoxin 2," FEMS Microbiol. Lett., 51: 211–216 [1988]; and N. C. Strockbine et al., "Characterization of Monoclonal Antibodies against Shiga-Like Toxin from *Escherichia coli*," Infect. Immun., 50: 695–700 [1985]), FIGS. 4 and 5 also demonstrate that antibodies generated against one toxin cross-reacted in vitro with the other toxin.

B. Western Blot Analysis.

Western blots (FIG. 6) performed to determine the reactivity of rVT antibodies against constituent VT polypeptides showed that rVT1 and rVT2 antibodies reacted with subunit A and fragment A1 of either toxin, and with subunit B and fragment A2 of rVT1 only. In this Figure, Panel A contains preimmune IgY, Panel B contains rVT1 IgY, and Panel C contains rVT2 IgY. Lane 1 in each panel contains rVT1 (2 $\mu$g) and lane 2 contains rVT2 (2 $\mu$g). Preimmune IgY was largely nonreactive to either rVT. Both rVT IgY preparations, however, failed to react with subunit B and fragment of rVT2. Some explanations for this lack of measurable reactivity might include poor immunogenicity, denaturation of the immunogen during glutaraldehyde treatment, loss of conformational epitopes due to detergent or reducing agent, or poor transfer to nitrocellulose.

To resolve the high and low molecular weight components, 2 $\mu$g each of rVT1 and rVT2 were separated by SDS-PAGE (described above) and then transferred to nitrocellulose paper using the Milliblot-SDE system (Millipore, Medford, Mass.) according to the manufacturer's instructions. Nitrocellulose strips were stained temporarily with Ponceau S (Sigma Chemical Company, St. Louis, Mo.) to visualize the polypeptides and then blocked overnight in PBS containing 5% dry milk. Each strip was agitated gently in IgY diluted in PBS-T for 2 hrs. at RT. Strips were each washed with three changes of PBS-T to remove unbound primary antibody and incubated for 2 hrs. at RT with goat anti-chicken alkaline phosphatase (Kirkegaard and Perry, Gaithersburg, Md.) diluted 1:500 in PBS-T containing 1 mg/ml BSA. The blots were washed as before and rinsed in 50 mM $Na_2CO_3$, pH 9.5. Strips were submerged in alkaline-phosphatase substrate (5-bromo-4-chloro-3-indolyl-phosphate/nitroblue tetrazolium (Kirkegaard and Perry) until sufficient signal was observed. Color development was stopped by flooding the blots with water.

EXAMPLE 4

In Vitro Toxin Neutralization

Vero Cell Assay

IgY neutralization of rVT1 and rVT2 was assessed using the modified Vero cytotoxicity assay described above (Example 1, part C). Various concentrations of IgY, diluted in Medium 199 supplemented with 5% fetal bovine serum (GIBCO), were mixed with sufficient toxin to cause 50% cell death and allowed to incubate at 37° C. for 60 minutes. These toxin/antibody mixtures were then added to Vero cell-coated microtiter plate wells according to the procedure described above (Example 1, part C).

The toxin neutralization capacity of the rVT antibodies was analyzed first using a Vero cell toxicity assay. The results in FIG. 7 show that rVT1 IgY neutralized completely the cytotoxic activity of rVT1 at an endpoint dilution of 1/320. Furthermore, rVT2 IgY neutralized the heterologous rVT1 toxin, but at a higher endpoint concentration.

In a similar experiment (see FIG. 8), rVT1 and rVT2 antibodies were each able to neutralize rVT2 at equivalent endpoint dilutions. This strong cross-neutralization correlates with the observed strong cross-reactivity of VT1 IgY with VT2 A seen on Western blots (FIG. 6). These results show that IgY antibodies are able to neutralize effectively VT cytotoxicity and that the antibodies can cross-neutralize structurally-related heterologous toxins.

EXAMPLE 5

Toxin Neutralization

Mouse Assays

A. Toxin Challenge Model.

IgY in PBS was premixed with a lethal dose of toxin (as determined above) and injected intraperitoneally into male CD-1 (20–22 gm) mice. Mice were observed for a 7-day period for signs of intoxication such as ruffled fur, huddling and disinclination to move, followed by hind leg paralysis, rapid breathing and death. Untreated, infected mice usually died within 12 hrs. after signs of severe illness (i.e., within 48–72 hrs. post-injection).

Once it was demonstrated that rVT antibodies were able to neutralize rVT cytotoxicity in vitro, protection experiments were next performed in mice. First, animals were challenged with rVT premixed with rVT IgY to determine whether toxin lethality could be neutralized under conditions optimal for antigen/antibody reaction. Tables 4 and 5 show that antibodies premixed with the homologous toxin (e.g., rVT1 with rVT1 IgY) prevented lethality of rVT. Preimmune IgY was unable to neutralize either toxin in these studies.

TABLE 4

Neutralization of rVT1 Using rVT IgY

| 100 ng rVT1 Premixed* | Survivors/Total | p |
|---|---|---|
| Preimmune Antibody | 0/12 | |
| rVT1 Antibody | 12/12 | <0.001 |
| rVT2 Antibody | 12/12 | <0.001 |

*Toxin was pre-mixed with IgY and incubated for 1 hour at room temperature prior to administration.

TABLE 5

Neutralization of rVT2 Using rVT IgY

| 10 ng rVT2 Premixed* | Survivors/Total | p |
|---|---|---|
| Preimmune Antibody | 0/12 | |
| rVT1 Antibody | 12/12 | <0.001 |
| rVT2 Antibody | 12/12 | <0.001 |

*Toxin was pre-mixed with IgY and incubated for 1 hour at room temperature prior to administration.

As shown in Tables 4 and 5, antibodies premixed with the heterologous toxin (e.g., rVT2 with rVT1 IgY) also prevented lethality in vivo. These data are in contrast to previous observations where rabbit polyclonal antibodies generated against either toxin were cross-reactive with the heterologous toxin by EIA and Western blot, but were unable to neutralize the heterologous toxin in either Vero cell cytotoxicity and mouse lethality assays (S. C. Head, et al., "Serological differences between verocytotoxin 2 and Shiga-like toxin II," Lancet ii: 751 [1988]; S. C. Head et al., "Purification and characterization of verocytotoxin 2," FEMS Microbiol. Lett., 51: 211–216 [1988]; N. C. Strockbine et al., "Characterization of Monoclonal Antibodies against Shiga-Like Toxin from *Escherichia coli*," Infect. Immun., 50: 695–700 [1985]; and V. V. Padhye et al., "Purification and Physicochemical Properties of a Unique Vero Cell Cytotoxin From *Escherichia coli* O157:H7," Biochem. Biophys. Res. Commun., 139: 424–430 [1986]).

However, Head et al., showed that VT2 B-subunit specific monoclonal antibodies neutralized VT1 weakly in a Vero cytotoxicity assay (S. C. Head, et al., "Serological differences between verocytotoxin 2 and Shiga-like toxin II," Lancet ii: 751 [1988]). In a report by Donohue-Rolfe, et al., a VT2 B subunit-specific monoclonal antibody neutralized both VT1 and VT2 completely in a Hela cytotoxicity assay (A. Donohue-Rolfe et al., "Purification of Shiga toxin and Shiga-like toxins I and II by receptor analog affinity chromatography with immobilized P1 glycoprotein and production of cross reactive monoclonal antibodies," Infect. Immun., 57: 3888–3893 [1989]).

These results showed for the first time complete cross-neutralization in Vero cell cytotoxicity and mouse lethality assays, revealing that VT1 and VT2 do indeed share common neutralizing epitopes. These results may indicate that hens generate different antibody specificities as compared to mammals, and/or that differences in immunization methods might have maintained the immunogenicity of conformational epitopes necessary for cross-neutralization. Nonetheless, this cross-neutralization suggests that IgY antibodies may contain the range of reactivities essential for an effective antitoxin.

B. Viable organism infection model.

Streptomycin-resistant *E. coli* O157:H7 (strain 933 cu-rev) or *E. coli* O91:H21 (strain B2F1) (both kindly provided by Dr. Alison O'Brien, Dept. of Microbiology and Immunology, Uniformed Services University of the Health Sciences, Bethesda, Md.) were used in a murine infection model described by Wadolkowski, et al. (E. A. Wadolkowski et al., "Mouse model for colonization and disease caused by enterohemorrhagic *Escherichia coli* O157:H7," Infect. Immun., 58: 2438–2445 [1990]). Organisms were grown in Luria broth and incubated overnight at 37° C. in an Environ Shaker (Lab Line, Melrose Park, Ill.) (T. Maniatis et al., *Molecular Cloning: a Laboratory Manual,* Cold Spring Harbor Laboratory, Cold Spring Harbor, N.Y., [1982]). Bacterial suspensions were centrifuged at 6700 x g for 5 minutes. The resulting pellet was then washed twice with sterile PBS and resuspended in sterile 20% (w/v) sucrose. Five to 8 week-old male CD-1 mice were provided drinking water containing 5 mg/ml streptomycin sulfate ad libitum for 24 hrs. Food and water were then withheld for another 16–18 hrs, after which mice were challenged orally with $10^{10}$ streptomycin-resistant *E. coli* O157:H7 or O91:H21. Mice were housed individually and permitted food and water containing 5 mg/ml streptomycin sulfate. IgY was injected intraperitoneally at varying times post-infection and animals observed for both morbidity and mortality for 10 days.

To monitor bacterial colonization in animals, 1 gram of feces was collected, homogenized, and plated onto MacConkey agar medium (Difco Laboratories, Detroit, Mich.) containing 100 μg/ml streptomycin and incubated at 37° C. as described by Wadolkowski, et al. (E. A. Wadolkowski et al., "Mouse model for colonization and disease caused by enterohemorrhagic *Escherichia coli* O157:H7," Infect. Immun., 58: 2438–2445 [1990]). The serotype of *E. coli* O157:H7, 933 cu-rev excreted in feces was confirmed by slide agglutination with O- and H-specific antisera (Difco Laboratories, Detroit, Mich.).

Kidneys were removed from experimental animals and fixed in 10% buffered neutral formalin. Sections of parafilm-embedded tissue were stained with hematoxylin and eosin (General Medical Laboratories, Madison, Wis.) and examined by light microscopy. All tissue sections were coded to avoid bias before microscopic examination to determine renal pathology.

The toxin neutralization ability of rVT IgY was further studied using a streptomycin-treated CD-1 mouse infection model. This model was chosen because it produces definitive systemic pathology and reproducible mortality.

In contrast to previous studies by Wadolkowski, et al. (E. A. Wadolkowski et al., "Acute renal tubular necrosis and death of mice orally infected with *Escherichia coli* strains that produce Shiga-like toxin Type II," Infect. Immun., 58: 3959–3965 [1990]), where mice were given subunit-specific monoclonal antibodies prior to infection, the mice in this study were inoculated orally with $2 \times 10^{10}$ viable *E. coli* O157:H7 (strain 933 cu-rev) and treated with rVT IgY 4 hrs. following inoculation. Fecal cultures showed that $10^7$–$10^8$ challenge organisms per gram of feces were shed throughout the course of the experiment, thus confirming that infection was established. Tables 6 and 7 show that animals treated with either rVT1 or rVT2 IgY were protected from lethality caused by infection (p<0.01 and p<0.001, respectively) and that preimmune IgY failed to provide protection to the mice.

TABLE 6

Protection of Mice From *E. coli* O157:H7 With rVT1 IgY

| IgY Treatment | Survivors/Total | p | Morbidity/Total |
|---|---|---|---|
| Preimmune Antibody | 0/5 | | 5/5 |
| rVT1 Antibody | 9/10 | <0.01 | 1/10 |

*IgY was administered intraperitoneally 4 hours following infection, and once daily for 10 days thereafter.

TABLE 7

Protection of Mice From *E. coli* O157:H7 With rVT2 IgY

| IgY Treatment | Survivors/Total | p | Morbidity/Total |
|---|---|---|---|
| Preimmune Antibody | 0/6 | | 6/6 |
| rVT2 Antibody | 10/10 | <0.005 | 0/10 |

*IgY was administered intraperitoneally 4 hours following infection, and once daily for 10 days thereafter.

Renal histopathology of the control (preimmune IgY) animals showed dilation, degeneration and renal tubular necrosis with no glomerular damage. This is consistent with previous reports showing that renal tubular involvement occurs predominantly in this streptomycin-treated mouse infection model (E. A. Wadolkowski et al., "Acute renal tubular necrosis and death of mice orally infected with *Escherichia coli* strains that produce Shiga-like toxin Type II," Infect. Immun., 58: 3959–3965 [1990]). Importantly, none of the survivors exhibited similar signs of morbidity though treated with IgY 4 hrs. after infection.

Furthermore, avian antibodies generated against rVT1 were able to prevent both mortality and morbidity in a mouse model where VT2 alone is implicated in the pathogenesis and lethality of *E. coli* O157:H7 strain 933 cu-rev (E. A. Wadolkowski et al., "Acute renal tubular necrosis and death of mice orally infected with *Escherichia coli* strains that produce Shiga-like toxin Type II," Infect. Immun., 58: 3959–3965 [1990]).

To assess the broader utility of the IgY verotoxin antibodies in treating VTEC-associated disease, the mouse infection study was performed using a more virulent VTEC serotype known to produce VT2c—a structural variant of VT2—but not VT1 (S. W. Lindgren et al., "Virulence of enterohemorrhagic *Escherichia coli* O91:H21 clinical isolates in an orally infected mouse model," Infect. Immun., 61: 3832–3842 [1993]).

Mice were inoculated orally with $5\times10^9$ *E. coli* O91:H21 (strain B2F1) and treated subsequently with IgY. Notably, the heterologous rVT1 IgY protected strongly against the lethal effects of the VT2c structural variant, even when administered as long as 10 hrs. following infection (Table 8). Ten hours was the longest treatment window tested in this study. Only 1 of the 8 animals treated with rVT1 IgY died ($p<0.02$), and those that survived showed no signs of renal pathology (i.e., acute bilateral tubular necrosis). It can thus be concluded that rVT1 IgY completely neutralized toxicity of VT2c, indicating its potential as a therapeutic for at least one other pathogenic VTEC.

TABLE 8

Protection of Mice From *E. coli* O91:H21 With rVT1 IgY

| IgY Treatment | Survivors/Total | p | Morbidity/Total |
|---|---|---|---|
| Preimmune Antibody | 0/7 | | 7/7 |
| rVT1 Antibody | 7/8 | <0.02 | 1/8 |

*IgY was administered intraperitoneally 10 hours following infection, and once daily for 8 days thereafter.

These Examples highlight several important findings supporting the feasibility of using verotoxin antitoxin. First, polyclonal IgY generated against either VT1 or VT2 from *E. coli* O157:H7, cross-reacted with and fully cross-neutralized the toxicity of the non-immunizing toxin both in vitro and in vivo. Second, recombinant toxins fully neutralized the toxicity of naturally-occurring toxins produced by *E. coli* O157:H7 during the course of infection. Third, antibodies generated against rVT1 from *E. coli* O157:H7 could prevent morbidity and mortality in mice infected orally with lethal doses of *E. coli* O91:H21, a particularly virulent strain which only produces VT2c, suggesting their utility in preventing systemic sequelae. Because VT1 is virtually identical to Shiga-toxin (A. D. O'Brien et al., "Shiga and Shiga-like toxins". Microbial Rev., 51: 206–220 [1987]), VT antibodies may also be useful in preventing complications stemming from *Shigella dysenteriae* infection. Finally, animals treated with VT IgY were protected against both death and kidney damage when treated as long as 10 hrs. after infection, supporting the hypothesis that a window for antitoxin intervention exists.

These studies strongly support the use of parenterally-administered, toxin-specific IgY as a antitoxin to prevent life-threatening complications associated with *E. coli* O157:H7 and other VTEC infections. It is contemplated that this approach would be useful in preventing HUS and other complications when administered after the onset of bloody diarrhea and before the presentation of systemic disease.

The VT IgY developed in these studies were shown to react with and neutralize both recombinant and naturally-occurring VT. The antibody titers as measured by EIA are indicative of reasonable antibody production in the hen, however much higher production levels can be obtained with larger immunizing doses.

The results from these Examples clearly demonstrate the feasibility and provide the experimental basis for development of an avian antidote for *E. coli* O157:H7 verotoxins suitable for use in humans. In contrast to previous reports showing that rabbit polyclonal VT1 and VT2 antibodies cross-reacted, but did not cross-neutralize the heterologous toxin in Vero cytotoxicity or in mouse lethality studies (e.g., V. V. Padhye et al., "Production and characterization of monoclonal antibodies to verotoxins 1 and 2 from *Escherichia coli* O157:H7," J. Agr. Food Chem., 39: 141–145 [1989]; S. C. Head et al., "Purification and characterization of verocytotoxin 2," FEMS Microbiol. Lett., 51: 211–216 [1988]; and N. C. Strockbine et al., "Characterization of monoclonal antibodies against Shiga-like toxin from *Escherichia coli*," Infect. Immun., 50: 695–700 [1985]), these data provide the first demonstration of cross-neutralization in vivo. Antibodies against one toxin neutralized completely the heterologous toxin in both Vero cytotoxicity and mouse lethality assays. Both rVT1 and rVT2 antibodies also prevented morbidity (as assessed by renal histopathology) and mortality in mice infected with lethal doses of *E. coli* O157:H7—the etiologic agent in 90% of the documented cases of hemolytic uremic syndrome (HUS) in the U.S. (P. M. Griffin and R. V. Tauxe, "The epidemiology of infections caused by *Escherichia coli* O157:H7, other enterohemorrhagic *E. coli*, and the associated hemolytic uremic syndrome," Epidemiol. Rev., 13: 60 [1991]). With at least two other VTEC serotypes known to cause HUS, the finding that rVT1 antibodies neutralized a VT2 variant produced by *E. coli* O91:H21 suggests that avian polyclonal antibodies may provide an effective antidote against other verotoxin-producing *E. coli*. These data also show for the first time, that antibodies may be administered after infection and still protect against morbidity and mortality.

EXAMPLE 6

Expression of Toxin Genes

The previous Examples clearly showed that avian polyclonal antibodies to recombinant toxins protected animals infected with verotoxigenic *E. coli*. This Example includes expression of toxin genes (A and B subunits alone and together as whole toxins) in suitable prokaryotic expression systems to achieve high levels of VT antigen production.

The sequence of both toxin genes (VT1 and VT2) has been determined (see e.g., M. P. Jackson et al., "Nucleotide sequence analysis and comparison of the structural genes for Shiga-like toxin I and Shiga-like toxin II encoded by bacteriophages from *Escherichia coli* 933," FEMS Microbiol. Lett., 44:109 [1987]; and Jackson et al., Microb. Pathogen., 2:147–153 [1987]). The genes show similar organization, such that the A and B chains of each toxin are juxtaposed in the same 5' to 3' orientation.

The coding regions of the A and B subunits of VT-1 are listed in SEQ ID NOS:1 and 3, respectively. The corresponding amino acid sequence of the A and B subunits of the VT-1 toxin are listed in SEQ ID NOS:2 and 4, respectively.

The coding regions of the A and B subunits of VT-2 are listed in SEQ ID NOS:5 and 7, respectively. The corresponding amino acid sequence of the A and B subunits of the VT-2 toxin are listed in SEQ ID NOS:6 and 8, respectively. In addition, SEQ ID NOS:9 and 10 list the sequences which direct the expression of a poly-cistronic RNA capable of directing the translation of both the A and B subunits from the VT-1 and VT-2 genes, respectively.

In choosing a strategy for recombinant VT antigen production, there are three primary technical factors to consider. First, the appropriate VT antigen components representing the spectrum of toxin epitopes encountered in nature must be utilized. Second, the protein antigens must be expressed at sufficient levels and purity to enable immunization and large-scale antibody purification. Third, the neutralizing epitopes must be preserved in the immnunogen and immunoabsorbant. Approaches that offer the greatest promise for high level expression of periplasmically localized proteins were developed. FIG. 10 shows the fusion constructs of VT components and affinity tags.

A. Expression of affinity-tagged C-terminal constructs.

The VT1 and VT2 A and B subunits (SEQ ID NOS:1, 3, 5 and 7) are cloned into the pET-23b vector (Novagen). This vector is designed to allow expression of native proteins containing C-terminal poly-His tags. The vector utilizes a strong T7 polymerase promoter to drive high level expression of target proteins. The methionine initiation codon is engineered to contain a unique NdeI restriction enzyme site (CATATG). The VT1 and VT2 genes are engineered to convert the signal sequence methionine codon into a NdeI site utilizing PCR mutagenesis. PCR primers were designed which contain the sequence GCCAT fused to the first 20–24 bases of the genes (starting at the ATG start codon of the signal tag; SEQ ID NOS:12–19, see Table below). Upon PCR amplification, the 5' start codon of each gene is converted to an NdeI site, compatible with the pET-23 vector-encoded NdeI site, allowing cloning of the amplified genes into the vector without the addition of vector-encoded amino acids.

Primers containing the C-terminal 7 codons of each gene (21 bases) fused to the sequence CTCGAGCC were synthesized, in order to add a C-terminal poly-His tag to each gene. The underlined bases are an XhoI site, that is compatible with the XhoI site of the pET-23 vector. These primers precisely delete the native stop codons, and when cloned into the pET-23 vector, add a C-terminal extension of "LeuGluHisHisHisHisHisHis" (SEQ ID NO: 11). The following table lists the primer pairs that are utilized to create PCR fragments containing the A and B subunits derived from VT-1 and VT-2 toxin genes suitable for insertion into the pET-23b vector.

TABLE 9

| Toxin Gene and Subunit | Primers | |
| --- | --- | --- |
|  | N-terminal Primer | C-terminal Primer |
| VT-1 Subunit A | SEQ ID NO:12 | SEQ ID NO:13 |
| VT-1 Subunit B | SEQ ID NO:14 | SEQ ID NO:15 |
| VT-2 Subunit A | SEQ ID NO:16 | SEQ ID NO:17 |
| VT-2 Subunit B | SEQ ID NO:18 | SEQ ID NO:19 |
| VT-1 Subunits A and B | SEQ ID NO:12 | SEQ ID NO:15 |
| VT-2 Subunits A and B | SEQ ID NO:16 | SEQ ID NO:19 |

Thus, utilizing PCR amplification with the above modified N- and C-terminal primers, the A and B subunits of VT1 and VT2 are expressed as proteins containing an 8 amino acid C-terminal extension bearing an poly-histidine affinity tag. The amino acid sequence of the histidine-tagged VT-1 A subunit produced by expression from the pET-23b vector is listed in SEQ ID NO:21 (the associated DNA sequence is listed in SEQ ID NO:20); the amino acid sequence of the histidine-tagged VT-1 B subunit is listed in SEQ ID NO:23 (the associated DNA sequence is listed in SEQ ID NO:22); the amino acid sequence of the histidine-tagged VT-2 A subunit is listed in SEQ ID NO:25 (the associated DNA sequence is listed in SEQ ID NO:24); the amino acid sequence of the histidine-tagged VT-2 B subunit is listed in SEQ ID NO:27 (the associated DNA sequence is listed in SEQ ID NO:26).

Both subunits may be expressed from a single expression constructs by utilizing SEQ ID NOS:12 and 15 to prime synthesis of the VT-1 toxin gene and SEQ ID NOS:16 and 19 to prime synthesis of the VT-2 toxin gene. The resulting PCR products are cleaved with NdeI and XhoI, as described for the cloning of the subunit genes into the pET-23b vector. Expression of the A and B subunits from such an expression vector, results in the expression of a native A subunit and a his-tagged B subunit. As the A and B subunits assemble into a complex, the presence of the his-tag on only the B subunit is sufficient to allow purification of the holotoxin on metal chelate columns as described below.

The proofreading Pfu polymerase (Stratagene) is utilized for PCR amplification to reduce the error rate during amplification. Genomic DNA from an *E. coli* O157:H7 strain is utilized as template DNA. Following the PCR, the amplification products are digested with NdeI and XhoI and cloned into the pCR-Script SK cloning vehicle (Stratagene) to permit DNA sequence analysis of the amplified products. The DNA sequence analysis is performed to ensure that no base changes are introduced during amplification. Once the desired clones are identified by DNA sequencing, the inserts are then excised utilizing NdeI and XhoI, and cloned into a similarly cut pET-23b vector to create the expression constructs. According to the published sequences, neither the VT1 nor VT2 genes contain either of these restriction sites.

The poly-His-tagged proteins produced by expression of the VT-1 and VT-2 gene sequences in the pET-23b constructs are then purified by IMAC. This method uses metal-chelate affinity chromatography to purify native or denatured proteins which have histidine tails (see e.g., K. J. Petty, "Metal-Chelate Affinity Chromatography," in Current Protocols in Molecular Biology, Supplement 24, Unit 10.11B [1993]).

B. Expression of Toxin Containing N-terminal Affinity Tags

Two expression systems, pMal-p2 and pFLAG-1 are utilized to attach an N-terminal affinity tag to the A subunits from the VT-1 and VT-2 toxins.

MBP-tagged constructs.

To construct A chains containing the maltose binding protein (MBP) at the N-terminus of the A subunit, PCR amplified gene products are cloned into the pMal-p2 vector (New England Biolabs) as C-terminal fusions to a periplasmically-secreted version of the MBP. The MBP selectively binds to amylose resins and serves as an affinity tag on the MBP/A subunit fusion protein. The pMal-p2 vector contains an engineered factor Xa cleavage site, which permits the removal of the affinity tag (i.e., MBP) from the fusion protein after purification.

The MBP/A subunit fusions are generated as follows. The VT1 and VT2 A subunits are PCR-amplified utilizing the following DNA primers. SEQ ID NOS:28–31; SEQ ID NOS:28 and 29 comprise the 5' and 3' primers, respectively, for the amplification of the VT1 A subunit; SEQ ID NOS:30 and 31 comprise the 5' and 3' primers, respectively, for the amplification of the VT2 A subunit. In both cases, the 5' or N-terminal primer contains the sequence CGGAATTC fused to the first codon of the mature polypeptide (rather than the start of the signal peptide, since the MBP signal peptide is utilized). These 5' primers contain an engineered EcoRI site that is not contained internally in either gene, that is compatible with the EcoRI site of the pMal-p2 vector. The 3' or C-terminal primers incorporate an XhoI site as described above for the generation of the His-tagged toxins, but in this case, the 3' primer is designed to include the natural termination codon of the A subunits.

The genes are amplified, cloned into pCR-Script SK, and sequenced as described above. The inserts are then excised with EcoRI and XhoI, and cloned into EcoRI/SalI-cleaved pMal-p2 vector (SalI and XhoI sites are compatible). This construct allows expression and secretion of the VT1 and VT2 A subunit genes as C-terminal fusions with MBP. The amino acid sequence of the MBP/VT-1A fusion protein is listed in SEQ ID NO:33 (the associated DNA sequence is listed in SEQ ID NO:32). The amino acid sequence of the MBP/VT-2A fusion protein is listed in SEQ ID NO:35 (the associated DNA sequence is listed in SEQ ID NO:34).

The resulting fusion proteins are then affinity purified on an amylose column and the bound fusion protein is eluted under mild conditions by competition with maltose. The MBP N-terminal-tagged A subunits are cleaved with factor Xa and the MBP is removed by chromatography on an amylose column. The resulting A subunits which contain a 4 amino acid N-terminal extension are then used as immunogens.

Flag tag constructs.

In an alternative embodiment, the VT1 and VT2 A subunit genes are engineered to contain the "flag tag" through the use of the pFLAG-1 vector system. The flag tag is located between the OmpA secretion signal sequence and the authentic N-terminus of the target protein in the pFlag-1 vector. To construct N-terminal flag-tagged A chains, the EcoRI/XhoI A subunit PCR fragments (generated as described above for the MBP fusion proteins) are cloned into identically cleaved pFlag-1 vector (Eastman-Kodak), to produce an expression construct utilizing the OmpA signal peptide for secretion of A subunit fusion proteins containing the flag peptide at the N-terminus. After secretion, the periplasmic protein contains the N-terminal 8 amino acid flag tag, followed by 4 vector-encoded amino acids fused to the recombinant A subunit. The amino acid sequence of the flag tag/VT-1 A subunit fusion protein is listed in SEQ ID NO:37 (the associated DNA sequence is listed in SEQ ID NO:36). The amino acid sequence of the flag tag/VT-2 A subunit fusion protein is listed in SEQ ID NO:39 (the associated DNA sequence is listed in SEQ ID NO:38).

The flag tag fusion proteins are then purified by immunoaffinity chromatography utilizing a calcium-dependent monoclonal antibody (Antiflag M1; Eastman-Kodak). Mild elution of purified protein is achieved by chelating the calcium in the column buffer with ethylenediamine tetraacetic acid (EDTA).

C. Evaluation of fusion construct expression.

The fusion constructs described above are expressed in *E. coli* strain BL21, or T7 polymerase-containing derivatives [e.g., BL21(DE3), BL21(DE3) pLysS, BL21(DE3)pLysE] (Novagen) for pET plasmids, and periplasmically-secreted recombinant protein purified by affinity chromatography.

Recombinant proteins are analyzed for correct conformation by testing the following parameters:

a) It is believed that the B subunit must associate into pentamers to be conformationally correct. This is assessed by reducing and native SDS-PAGE analyses of native and chemically-cross-linked proteins and sizing HPLC;

b) It is believed that a properly folded A subunit is expected to retain its native enzymatic activity. This is tested by its capacity to inhibit protein synthesis in an in vitro toxicity assay;

c) It is believed that in vitro toxicity of assembled recombinant holotoxin can be assessed by comparison to commercially available holotoxins to determine whether recombinant A and B subunits can assemble into functional holotoxin. The purified N-terminal-tagged A subunits (after cleavage and purification from MBP or untreated flag-tagged proteins) are combined in vitro with the corresponding B chains, and their toxicity evaluated utilizing a quantitative microtiter cytotoxicity assay, such as that described by M. K. Gentry and M. Dalrymple, "Quantitative Microtiter Cytotoxicity Assay for Shigella Toxin," J. Clin. Microbiol., 12:361–366 (1980).

EXAMPLE 7

Verotoxin Clone Construction

In this Example, vectors expressing VT1A and B, and VT2A and B subunits with a C-terminal his-tag were constructed, as well as vectors expressing VT1A and VT2A as a fusion with the MBP. In addition, vectors capable of expressing the native VT1A and VT2A subunits (i.e., without an affinity tag) were also generated. Table 10 provides a summary of VT constructs and provides information concerning the parent vector, the affinity tag (if present) and the antibiotic selection employed for growth of the plasmid construct. In Table 10, the term "L+" indicates that the expression vector encodes the preprotein form of the verotoxin subunit (i.e., the plasmid utilizes the naturally occurring signal sequence for secretion of the verotoxin subunit into the periplasm of the host cell). "L−" indicates that the expression vector encodes the mature form of the verotoxin subunit (i.e., sequences encoding the naturally occuring signal sequence of the verotoxin subunit are not present and therefore the protein will remain intracellular).

The predicted amino acid sequences of the subunit proteins expressed by the plasmids listed in Table 10 are as follows: pET23hisVT1A L+ and pET24hisVT1A L+ (SEQ ID NO:21); pET23hisVT1 A L− (amino acid residues 23–323 of SEQ ID NO:21); pET23hisVT2A L+ and pET24hisVT2A L+ (SEQ ID NO:25); pET23hisVT2A L− (amino acid residues 23–326 of SEQ ID NO:25); pET23hisVT1B L+ and pET24hisVT1B (SEQ ID NO:23); pEThisVT1B L− (amino acid residues 20–97 of SEQ ID NO:23); pET24VT1B and pET24T7VT1B (SEQ ID NO:4); pET23hisVT2B L+ and pET24hisVT2B L+ (SEQ ID NO:27); pET24VT2B, pET24T7VT2B and pET24T7VT2B lacIq− (SEQ ID NO:8); pET24hisVT2B L− (amino acid residues 20–97 of SEQ ID NO:27); pMalVT1A (SEQ ID NO:47; the nucleotide sequence encoding the MBP/VT1A fusion protein is provided in SEQ ID NO:46); pMalVT2 A (SEQ ID NO:49; the nucleotide sequence encoding the MBP/VT2A fusion protein is provided in SEQ ID NO:48).

TABLE 10

Plasmid Constructs

| Plasmid | VT Subunit | Parent Vector | Transcriptional Control | Affinity Tag | Selection |
|---|---|---|---|---|---|
| pET23hisVT1 A L+ | VT1A(L+) | pET23 | T7 | 6X HIS | Amp |
| pET24hisVT1 A L+ | VT1A(L+) | pET24 | T7lac | 6X HIS | Kan |
| pET23hisVT1 A L- | VT1A(L-) | pE23 | T7 | 6X HIS | Amp |
| pET23hisVT2 A L+ | VT2A(L+) | pET23 | T7 | 6X HIS | Amp |
| pET24hisVT2 A L+ | VT2A(L+) | pET24 | T7lac | 6X HIS | Kan |
| pET23hisVT2 A L- | VT2A(L-) | pET23 | T7 | 6X HIS | Amp |
| pET23hisVT1 B L+ | VT1B(L+) | pET23 | T7 | 6X HIS | Amp |
| pET24hisVT1 B L+ | VT1B(L+) | pET24 | T7lac | 6X HIS | Kan |
| pET23hisVT1 B L- | VT1B(L-) | pET23 | T7 | 6X HIS | Amp |
| pET24VT1 B | VT1B(L+) | pET24 | T7lac | NONE | Kan |
| pET24T7VT1 B | VT1B(L+) | pET24VT1B | T7 | NONE | Kan |
| pET23hisVT2 B L+ | VT2B(L+) | pET23 | T7 | 6X HIS | Amp |
| pET24hisVT2 B L+ | VT2B(L+) | pET24 | T7lac | 6X HIS | Kan |
| pET24VT2 B | VT2B(L+) | pET24 | T7lac | NONE | Kan |
| pET24T7VT2 B | VT2B(L+) | pET24VT2B | T7 | NONE | Kan |
| pET24T7VT2 B lacIq- | VT2B(L+) | pET24VT2B | T7lac | NONE | Kan |
| pET24hisVT2 B L- | VT2B(L-) | pET24 | T7lac | 6X HIS | Kan |
| pMalVT1 A | VT1A(L-) | pMAL-p2 | ptac | MPB | Amp |
| pMalVT2 A | VT2A(L-) | pMAL-p2 | ptac | MPB | Amp |
| pMalVT2 A (BamHI) | VT2A(L-) | pMalVT2 A | ptac | MPB | Amp |

A. His-Tagged Constructs

The pET vectors (Novagen, Madison, Wis.) were used to produce his-tagged recombinant subunits. These vectors were designed to express each subunit with a C terminal 6X his-tag (i.e., a tag comprised of six histidine residues) to facilitate affinity purification using immobilized metal chelate columns. The coding regions for each subunit were cloned using PCR amplification from *E. coli* 933 genomic DNA. The subunits were amplified from genomic DNA using the L+ and L– primers. L+ indicates a 5' primer that contains the native periplasmic secretion signal, L– indicates a 5' primer that is designed to delete the native secretion signal and produces the recombinant protein intracellularly. Table 11 lists the primers used to make the his-tagged constructs.

TABLE 11

Primers Used for Amplification of Genomic *E. coli* 933 DNA

| Subunit Primer | Primer Sequence | SEQ ID NO: |
|---|---|---|
| VT1A 5' L+ | GC<u>CATATG</u>AAAATAATTATTTTTAGAGTG (*Nde*I site underlined) | SEQ ID NO:12 |
| VT1 A 5' L- | GC<u>CATATG</u>AAGGAATTTACCTTAGAC (*Nde*I site underlined) | SEQ ID NO:40 |

TABLE 11-continued

Primers Used for Amplification of Genomic *E. coli* 933 DNA

| Subunit Primer | Primer Sequence | SEQ ID NO: |
|---|---|---|
| VT1 A 3' | GG<u>CTCGAG</u>ACTGCTAATAGTTCTGCGCAT (*Xho*I site underlined) | SEQ ID NO:13 |
| VT2 A 5' L+ | GC<u>CATATG</u>AAGTGTATATTTAAATGG (*Nde*I site underlined) | SEQ ID NO:16 |
| VT2 A 5' L- | GC<u>CATATG</u>CGGGAGTTTACGATAGAC (*Nde*I site underlined) | SEQ ID NO:41 |
| VT2 A 3' | GG<u>CTCGAG</u>TTTACCCGTTGTATATAAAAAC (*Xho*I site underlined) | SEQ ID NO:17 |
| VT1 B 5' L+ | GC<u>CATATG</u>AAAAAAACATTATTAATAGC (*Nde*I site underlined) | SEQ ID NO:14 |
| VT1 B 5' L- | GC<u>CATATG</u>ACGCCTGATTGTGTAACT (*Nde*I site underlined) | SEQ ID NO:42 |
| VT1 B 3' | GG<u>CTCGAG</u>ACGAAAAATAACTTCGCTGAA (*Xho*I site underlined) | SEQ ID NO:15 |
| VT2 B 5' L+ | CG<u>CATATG</u>AAGAAGATGTTTATGGCG (*Nde*I site underlined) | SEQ ID NO:18 |
| VT2 B 5' L- | GC<u>CATATG</u>GCGGATTGTGCTAAAGG (*Nde*I site underlined), | SEQ ID NO:43 |
| VT2 B 3' | GG<u>CTCGAG</u>GTCATTATTAAACTGCACTTC (*Xho*I site underlined) | SEQ ID NO:19 |

The *E. coli* O157:H7 933 strain was obtained from Dr. O'Brien (See, Example 5), and grown in L broth (Maniatis et al). High molecular-weight *E. coli* genomic DNA was isolated essentially as described by Wren and Tabaqchali, "Restriction endonuclease DNA analysis of *Clostridium difficile*," J. Clin. Microbiol., 25:2402–2404 [1987]), with the exceptions being that proteinase K and sodium dodecyl sulfate (SDS) were used to disrupt the bacteria, and methods for CTAB precipitation as described in another reference (Ausubel et al., (eds.), in Current Protocols in Molecular Biology pages 2.4.1–2.4.2 [1995]) were used to remove carbohydrates from the cleared lysate. The integrity and yield of genomic DNA was assessed by comparison with a serial dilution of uncut lambda DNA after electrophoresis on an agarose gel.

The gene fragments were cloned by PCR, utilizing a proofreading thermostable DNA polymerase (native Pfu polymerase; Stratagene). This polymerase was chosen as its high fidelity of this polymerase reduces the mutation problems associated with amplification by error prone polymerases (e.g. Taq polymerase). PCR amplification was performed using the indicated PCR primer pairs with two amplifications conducted for each subunit (i.e., 5' L+ primer/3' primer and 5' L– primer/3' primer) in 50 µl reactions containing 10 mM Tris-HCl (pH 8.3), 50 mM KCl, 1.5 mM $MgCl_2$, 200 µM of each dNTP, 0.2 µM of each primer, and 50 ng *E. coli* genomic DNA. Reactions were overlayed with 100 µl mineral oil, heated to 94° C. 4 min, 0.5 µl native Pfu polymerase (Stratagene) were added, and the reaction cycled for thirty times (94° C. for 1 min, 50° C. for 2 min, 72° C. for 4 min), followed by 10 min at 72° C.). Then, 10 µl aliquots of amplified DNA were resolved on agarose gels, and amplified DNA gel purified using the Prep-A-Gene kit (Biorad), and ligated to pCRScript vector DNA (Stratagene). Recombinant clones were isolated and confirmed by restriction digestion, or sequencing (VT1B and VT2B clones) using standard recombinant molecular biology techniques (Sambrook et al., 1989).

Expression plasmids were constructed as follows, and manipulations were identically performed for L+ and L− clones. The subunit clones in the PCRscript vector were cleaved with NdeI/XhoI, and gel purified subunit fragments were cloned into gel purified NdeI/XhoI-digested pET23b vector. The resulting clones, designated as pET23hisVT1AL+, pET23hisVT1AL−, pET23hisVT1BL+, pET23hisVT1BL−, pET23hisVT2AL+, pET23hisVT2AL−, and pET23hisVT2BL+, were ampicillin resistant and expressed the subunits utilizing the T7 promoter. All clones were confirmed by restriction mapping.

In addition, T7lac, kan, LacIq L+ or L− clones were also constructed as described above, substituting NdeI/XhoI-cleaved pET24 vector for pET23 vector. These 5 clones, designated as pET24hisVT1AL+, pET24hisVT1BL+, pET24VT2AL+, pET24VT2BL+, and pET24VT2BL−, were confirmed by restriction digestion.

B. Construction of Vectors Without Affinity Tags

Vectors lacking affinity tags were also produced. These vectors were designed to express the VT1B and VT2B subunits periplasmically, without any additional amino acids. The subunits are contemplated to have a native sequence, since the coding region of the expression constructs were unaltered from the original genes.

The subunits were PCR-amplified from *E. coli* O157:H7 933 genomic DNA, the amplified bands were gel purified and then cloned into the pCRScript vector as described above. The amplifications were performed utilizing the VT1B or VT2B 5' L+ primers described above (i.e., SEQ ID NO:14 or 18), and the following 3' primers. The VT1B native 3' primer had the sequence 5'-GGCTCGAGTCAACGAAAAATAACTTCGCTGAA-3' (XhoI site underlined) (SEQ ID NO:44); and the VT2 B native 3' primer had the sequence 5'-GGCTCGAGTCAGTCATTATTAAACTGCACTTC-3' (XhoI site underlined) (SEQ ID NO:45).

The initial expression constructs were constructed by cloning the NdeI/XhoI fragments from the pCRScript clones into NdeI/XhoI-cleaved pET24a vector. The clones were designated pET24VT1B or pET24VT2B, and were confirmed by complete sequencing of the inserts. These clones contained the lacIq gene, and verotoxin subunits expression was driven by the T7lac promoter. To increase expression yields, pET24-derived plasmids in which the T7 promoter was substituted for the T7lac promoter were constructed. The insert containing xbaI/XhoI fragments of pET24VT1B and pET24VT2B were cloned into XbaI/XhoI released vector from the pHisBotE kan lacIq T7 vector (described in co-pending U.S. patent application Ser. No. 08/704,159, herein incorporated by reference). A equivalent vector backbone can be generated as follows. pET24 is digested with XbaI and SapI and the ~2.6 kb band containing the kan$^R$ gene, fl origin and plasmid origin is isolated and ligated to the 996 bp XbaI/SapI fragment from pET23. The resulting plasmid contains the T7 promoter but lacks the lacIq gene. The resulting plasmid is then digested with BglII and SapI and the large fragment is isolated and ligated to the ~2.7 BglII/SapI fragment from pET24. The final construct contains the kan$^R$ gene, the T7 promoter and the lacIq gene. The resultant clones, pET24T7VT1B and pET24T7VT2B, were confirmed by sequencing.

Finally, a VT2B expressing construct that was kanamycin resistant, contained the T7lac promoter but had deleted the lacIq gene was constructed, by insertion of the insert containing XhoI/BglII fragment from pET24VT2B into the XhoI/BglII vector backbone released from the pHisBotA kan plasmid (described in co-pending U.S. patent application Ser. No. 08/704,159, supra). An equivalent vector backbone can be generated as follows. pET24 is digested with BglII and SapI and the ~2.6 kb band containing the T7lac promoter, kanR gene, fl origin and the plasmid origin is isolated. pET23 is digested with BglII and SapI and the 996 bp fragment is isolated and ligated to the ~2.6 kb fragment form pET24. The resulting plasmid contains the kan$^R$ gene and the T7lac promoter but lacks the lacIq gene (referred to as a lacIq− derivative of pET24).

C. MBP Fusions

In this experiment, alternative methods for tagging the proteins were used with the pMal vector/expression system New England Biolabs). These vectors were designed to express the recombinant subunits with maltose binding protein (30 kd), in order to allow affinity purification of the recombinant subunits on amylose resins. In this experiment, pMalVT1A and pMalVT2A plasmids were constructed.

For pMalVT1A, the insert from a pCRScript L+ clone containing the amplified VT1A gene in the appropriate orientation was excised with BamHI/XhoI and cloned into BamHI/SalI-cleaved pMAL-c2 (New England Biolabs). The resultant clone was confirmed by restriction digestion.

For pMalVT2A, the insert from a pCRScript L+ clone containing the amplified VT2A gene in the appropriate orientation was excised with BamHI/XhoI and cloned into BamHI/SalI-cleaved pMAL-p2. The resultant clone was confirmed by restriction digestion. As discussed below, the VT2A PCR amplification product in this pCRScript L+ clone appeared to have deleted a nucleotide at the 5' end that resulted in a shift (−1) in the reading frame of the VT2A subunit. Therefore, a derivative clone pMalVT2A(BamHI) was also constructed that inserted 4 bp and induced a +1 frameshift relative to the parent vector by digesting pMalVT2A with BamHI, filling in the BamHI site using the Klenow enxzyme and all 4 dNTPs followed by circularization of the plasmid. The nucleotide sequence encoding the MBP/VT2A subunit expressed by pMalVT2 A(BamHI) is listed in SEQ ID NO:48; the amino acid sequence of this fusion protein is provided in SEQ ID NO:49.

EXAMPLE 8

Expression of Verotoxin His-Tagged Clones

In this Example, methods used for the expression of his-tagged clones was developed. In this Example, the pET vector derived verotoxin expression constructs were transformed into BL21(DE3) containing *E. coli* cell lines for expression. However, several expression constructs were found to be toxic in these cell lines. The viability of the various cell lines is summarized in the following Table.

TABLE 12

Growth and Viability of Verotoxin-Expression Constructs in *E. coli* Cell Lines

| Plasmid | BL21 (DE3) | BL21(DE3)plysS | BL21(DE3)plysE |
|---|---|---|---|
| pET23hisVT1AL+ | Negative | Positive | Positive |
| pET23hisVT2AL+ | Negative | Positive | Positive |
| pET23hisVT1BL+ | Negative | Positive | Positive |
| pET23hisVT2BL+ | NA | Negative | Positive |
| pET23hisVT1AL− | Positive | Positive | NA |

TABLE 12-continued

| Growth and Viability of Verotoxin-Expression Constructs in *E. coli* Cell Lines | | | |
|---|---|---|---|
| Plasmid | BL21 (DE3) | BL21(DE3)plysS | BL21(DE3)plysE |
| pET23hisVT2AL− | Negative | Slow growth | NA |
| pET23hisVT1BL− | Negative | Slow growth | NA |
| pET24hisVT2BL− | Positive | NA | NA |
| pET24hisVT1AL+ | Positive | NA | NA |
| pET24hisVT2AL+ | Positive | NA | NA |
| pET24hisVT1BL+ | Positive | Positive | NA |
| pET24hisVT2BL+ | Positive | Positive | NA |
| pET24VT1B | Positive | NA | NA |
| pET24T7VT1B | Positive | NA | NA |
| pET24VT2B | Positive | NA | NA |
| pET24T7VT2B | Negative | NA | NA |
| pET24VT2BlacIq− | Negative | NA | NA |

From these results, it appeared that expression of any of the verotoxin subunits is toxic to *E. coli*, and that the only clones that are viable in the BL21(DE3) cell line are those in which subunit expression is tightly repressed in uninduced cells, either by use of a T7lac promoter or the lacIq gene or both.

Protein expression was induced in 1 liter shaker flask cultures utilizing recombinant plasmids in the BL21(DE3)-derived *E. coli* strains. Procedures for protein induction, SDS-PAGE, and Western blot analysis were described in detail in Williams et al (Williams et al., in Glover and Hames (eds.), *DNA Cloning* 2: *Expression Systems, A Practical Approach,* 2d ed., IRL Press [1995], pages 15–57).

In brief, 1 liter 2XYT+0.2% glucose+either 40 μg/ml kanamycin (pET24 plasmids) or 100 μg/ml ampicillin (pET23 plasmids) cultures of bacteria were induced to express recombinant protein by addition of IPTG to 1 mM. For optimal results, cultures were grown at 30–32° C., overnight and induced when the cell density reached >2 $OD_{600}$. Induced protein was allowed to accumulate for 2–4 hrs after induction. Induction at lower $OD_{600}$ readings (e.g., 0.5–1.0) resulted in the accumulation of lower overall levels of verotoxin subunits, since induction of subunit expression halted *E. coli* cell growth and final cell pellets were therefore dramatically smaller. In the case of VT1B and VT2B expressing constructs, the verotoxin subunits were insoluble if grown and induced at 37° C.

The cells were harvested by centrifugation 10 min at 5000 rpm in a JA10 rotor at 4° C. The pellets were resuspended in a total volume of 40 mls 1X binding buffer (5 mM imidazole, 0.5 M NaCl, 50 mM $NaPO_4$, pH 8.0)+1 mg/ml lysozyme (if lysS or lysE plasmid was not present), transferred to two 50 ml Oakridge tubes and frozen at −70° C., for at least 1 hr. The tubes were thawed and the cells lysed by sonication (4×20 second bursts) on ice. The suspension was clarified by centrifugation 20–30 min at 9,000 rpm (10,000 xg) in a JA-17 rotor. The soluble lysate was batch-absorbed to 7 mls of a 1:1 slurry of NiNTA resin: binding buffer by stirring 2–4 hr at 4° C. The slurry was centrifuged 1 min at 500 xg in a 50 ml tube (Falcon), resuspended in 5 mls binding buffer and poured into a 2.5 cm diameter column (Biorad). The column was attached to an UV monitor (Isco), and washed with binding buffer, then binding buffer +20–40 mM imidazole until baseline was established. Bound protein was eluted in elution buffer (50 mM $NaPO_4$, 0.3 M NaCl, 20% glycerol, 250 mM imidazole, pH 8.0) and stored at +4 or −20° C.

Samples of total, soluble, flow through and eluted protein were then resolved by SDS-PAGE. Protein samples were prepared by mixing 1 μl total (T), soluble (S) or flow through (A) protein with 4 μl PBS and 5 μl 2X SDS-PAGE sample buffer, or 5 μl eluted (E) protein and 5 μl 2X SDS-PAGE sample buffer (See, co-pending U.S. patent application Ser. No. 08/704,159). The samples were heated to 95° C. for 5 min, cooled, and 5 or 10 μls were loaded on 12.5% SDS-PAGE gels. Broad range molecular weight protein markers (BioRad) were also loaded to allow the MW of the identified fusion proteins to be estimated. After electrophoresis, protein was detected either generally by staining gels with Coomassie blue. A representative Coomassie stained 20% SDS-PAGE gel demonstrating purification of his-tagged VT1B and VT2B proteins is shown in FIG. 11.

The result of electrophoresis (not shown) indicate that the VT1B protein is smaller than the VT2B protein. In fact, the VT2BL+ and VT2BL− proteins were of identical size, indicating that the VT2BL+ protein has the leader peptide cleaved off and is thus likely to be periplasmically secreted.

Purification yields and purity from 1 l shaker flask cultures, for several his-tagged plasmid/host cell combinations, are shown in Table 13 (purity was estimated by visual inspection of the Coomassie-stained SDS-PAGE gels). In Table 13, the protein concentration was estimated using 1 mg/ml solution=2 $OD_{280}$/ml.

TABLE 13

| Purification of His-Tagged Verotoxin Proteins | | | |
|---|---|---|---|
| Plasmid | Host strain | Wash buffer imidazole conc. | Yield & Purity |
| pET24hiSVT1BL+ | BL21(DE3) | 40 mM imidazole | 2.5–5 mg/l >50% purity |
| pET24hisVT2BL+ | BL21(DE3) | 40 mM imidazole | 60–70 mg/l >90% purity |
| pET24hisVT1AL+ | BL21(DE3) | 20 mM, then 40 mM imidazole | <1 mg/l <10% purity |
| pET24hisVT2AL+ | BL21(DE3) | 20 mM, then 40 mM imidazole | <1 mg/l <10% purity |
| pET23hisVT1BL+ | BL21(DE3)plysS | 40 mM imidazole | 2.5–5 mg/l >50% purity |
| pET23hisVT2BL+ | BL21(DE3)plysE | 40 mM imidazole | >30 mg/l >90% purity |
| pET23hisVT1AL+ | BL2I(DE3)plysS | 20 mM imidazole | <1 mg/l <10% purity |
| pET23hisVT2AL+ | BL21(DE3)plysS | 20 mM imidazole | <1 mg/l <10% purity |
| pET23hisVT1AL− | BL21(DE3) | 20 mM, then 40 mM imidazole | <1 mg/l <10% purity |
| pBT23hisVT2AL− | BL21(DE3)plysS | 20 mM, then 40 mM imidazole | <1 mg/l <10% purity |
| pET23hisVTIBL− | BL21(DE3)plysE | 20 mM, then 40 mM imidazole | <1 mg/l <10% purity |
| pET24hisVT2BL− | BL21(DE3) | 20 mM, then 40 mM imidazole | >40 mg/l >90% purity |

Expression and purification of large quantities (>40 mg/l) of the VT2B subunit was obtainable utilizing any of the described expression systems. However, due to toxicity of the VT2B subunit, strict uninduced promoter control was necessary to allow cell viability. This was accomplished by coexpression with the plysE plasmid in the case of the pET23hisVT2BL+ plasmid, or the presence of the lacIq gene and the T7lac promoter in the pET24hisVT2BL+ and L− plasmids. Due to the need for disulfide bond formation and pentamer assembly, the vectors that allowed periplasmic secretion of the protein (L+) were found to be preferable, since intracellular *E. coli* is a reducing environment. In addition, due to scaleup and plasmid stability concerns, the pET24 construct was found to be preferable to the pET 23 construct.

Expression and purification of moderate quantities (5 mg/l) of the VT1B subunit was also attainable utilizing any of the described expression systems. The VT1B subunit is less toxic than the VT2B subunit, allowing less stringent control of uninduced verotoxin expression. Due to the need for disulfide bond formation and pentamer assembly, the vectors that allow periplasmic secretion of the protein (L+) were found to be preferable. As with the VT2B subunit, due to scaleup and plasmid stability concerns, the pET24 construct was found to be preferable to the pET 23 construct.

In contrast to the VT1B yields, very poor yields of purified VT1A or VT2A subunits were obtained, utilizing either L+ or L− vectors.

EXAMPLE 9

VT1 Subunit A and VT2 Subunit A MBP Clone Expression

Due to the poor recovery of his-tagged VT1A and VT2A protein, expression of MBP fused VT1A and VT2A subunits was undertaken in this Example. Large scale (1 liter) cultures of pMalVT1A, pMalVT2A and pMalVT2A(BamHI) in the BL21 plysS strain were grown, induced, and soluble protein fractions were isolated. One liter cultures were grown at 30° C. in 2XYT broth containing 0.2% glucose and 100 μg/ml ampicillin. Recombinant protein expression was induced by addition of IPTG to 1.0 mM at approximately 1.0 $OD_{600}$ cell density. Cultures were induced for 2–3 hrs. The cells were collected by centrifugation in a JA10 rotor (Beckman) at 5000 rpm for 10 min. at 4° C. The cell pellet was resuspended in 40 ml PBS and frozen at −70° C. The samples were thawed in warm water and sonicated using a Branson Sonifier with the microtip (20 sec/pulse, 8 pulses total). The sonicated material was then and clarifed by centrifugation (Beckman JS13 rotor at 10,000 rpm at 4° C. for 20 min.). The supernatant (i.e., the soluble extract) was then decanted. Williams et al 1995, supra.

The soluble extracts were diluted to 200 mls with PBS, chromatographed over an amylose resin (New England Biolabs) column and the flow through material (i.e., proteins that did not bind to the resin) was collected. The column was then washed with PBS until a stable baseline was established, and eluted with PBS containing 10 mM maltose as described (Williams et al. [1995], supra). Protein yields were 22 mg (pMalVT1A), 13.5 mg (pMalVT2A) or 12.5 mg [pMalVT2A(BamHI)] from 1 liter starting volume for each recombinant (protein concentration estimated using 1 mg/ml=2 $OD_{280}$/ml). The results of electroporesis (not shown) indicate that significant amounts of predicted full length VT1A and VT2A proteins (arrows) were produced by the pMa1VTIA and pMa1VT2A(BamHI) plasmid, but not the pMa1VT2A plasmid.

Although it is not necessary to the practice of the present invention, it was assumed that the VT2A PCR amplification product contained within the pCRScript L+ clone containing the VT2A gene had deleted a nucleotide at the 5' end, as introduction of a frameshift by the addition of 4 bases in the filled BamHI site of the pMalVT2B(BamHI) vector resulted in accumulation of the predicted full length protein. The identity of the predicted full length VT1A and VT2A proteins was confirmed by Western blot analysis. Verotoxin protein was identified utilizing a chicken anti-VT1 IgY.

For Westerns, samples of the pMalVT1A, pMalVT2A and pMalVT2A(BamHI) elutions were resolved on SDS-PAGE gels as described above, the gels were blotted, and protein transfer confirmed by Ponceau S staining (See, Williams et al., [1995] supra). After blocking the blots for 1 hr at room temp in PBS +0.1% Tween-20 (PBST) containing 5% milk (Blocking Buffer), 10 ml of a ⅟₁₀₀₀ dilution of a anti-VT1 holotoxin IgY PEG preparation in Blocking Buffer was added and the blots were incubated a further 1 hr at room temperature. The blots were washed and developed with alkaline phosphatase, using a rabbit anti-chicken alkaline phosphatase conjugate as the secondary antibody (See, Williams et al., [1995], supra). This analysis confirmed that the full length proteins detected by Coomassie gel analysis in were immunoreactive with the anti-VT1 antibody preparation. The reactivity of the VT2A protein with the VT1 antiserum was predicted, as the VT1 antiserum was demonstrated to cross-react with the VT2 protein in previous Examples. From Coomassie gel staining, it was estimated that 50% of the pMalVT1A elution and 10% of the pMalVT2A(BamHI) elution was full-length fusion protein. This corresponds to 11 mg/l (VT1A) or 1.25 mg/l (VT2A) yields of full length verotoxin subunit using these expression systems.

EXAMPLE 10

Expression of Native Verotoxin B Subunit

In this Example, the pET24VT1B (T7 and T7lac) and pET24VT2B expression vectors were evaluated for their utility in expression of native VT1B and VT2B subunits. The pET24VT2B plasmid was selected for study, since this is the only VT2B expression vector that is viable in the BL21(DE3) cell line (see Table 12). Expression levels from pET24VT1B and pET24T7VT1B were evaluated by Western Blot analysis of total and soluble protein extracts from small scale culture.

A. Expression of VT1B

Fifty ml 2XYT+40 μg/ml kanamycin cultures of each plasmid in the BL21(DE3) strain were grown until $OD_{600}$>2.0, and verotoxin expression was induced for 3 hrs after addition of IPTG to 1 mM. A total of 10 $OD_{600}$ units of cells (e.g., 5 mls of cells at $OD_{600}$=2/ml) were removed before and after induction and pelleted 5 min at maximum rpm in a benchtop centrifuge. The pellets were resuspended in 1 ml of 50 mM $NaHPO_4$, 0.5 M NaCl, 40 mM imidazole buffer, pH 6.8, containing 1 mg/ml lysozyme. The samples were incubated 20 min. at room temp and stored overnight at −70° C. Samples were thawed completely at room temperature and sonicated 2×10 seconds with a Branson sonifier 450 microtip probe at # 3 power setting. The samples were centrifuged 5 min at maximum rpm in a microfuge. Twenty μl protein samples were removed to 20 μl 2X sample buffer, before or after centrifugation, for total and soluble protein extracts respectively. The samples were heated to 95° C. for 5 min, cooled and 5 (15 lane gels) or 10 (10 lane gels) μls loaded on 20% SDS-PAGE gels. High molecular weight protein markers (Biorad) were also loaded, to allow estimation of the molecular weight of identified fusion proteins. After electrophoresis, VT1B subunit protein was detected specifically, by blotting to nitrocellulose for Western blot detection utilizing a VT1B reactive monoclonal antibody. Western blot analysis was performed as described in Example 3, utilizing 1 μg/ml SLT13C4 (anti-VT1B monoclonal; Toxin Technology, Sarasota, Fla.) as primary, and ⅟₁₀₀₀ diluted anti-mouse alkaline phosphatase conjugate (Kirkegaard Perry Laboratories, Gaitherburg, Md.) as secondary antibodies. No immunoreactive protein was detected in uninduced cell extracts from either cell line, while a single immunoreactive band of the predicted molecular weight was detected in the induced cell extract from both cell lines. The induced verotoxin expression level was much higher with the pET24T7VT1B expression construct; this construct was selected for further study. This analysis demonstrated that both expression systems produce inducible verotoxin subunit proteins.

B. Collection of VT1B and VT2B Total, Soluble, Periplasmic, and Culture Broth

Cultures of VT1B and VT2B were grown and induced, and total, soluble, periplasmic and culture broth samples collected, to allow protein quantification and subcellular localization of expressed verotoxins to be determined. One liter 2XYT+0.2% glucose+40 µg/ml kanamycin cultures of pET24VT2B and pET24T7VT1B were grown at 30–32° C., until $OD_{600}$=1–2, and verotoxin expression induced by addition of IPTG to 1 mM, and the cultures grown 2.5–3 hrs. Total and soluble extracts were prepared from 10 $OD_{600}$ units of cells as described above. Samples of clarified culture broth were retained for detection of secreted verotoxin subunit. The 1 liter cultures were pelleted by centrifugation 10 min at 8000 x g. Osmotic shock and PMB-induced periplasmic extracts were then prepared. Half of the pellet was resuspended in 200 ml 30 mM Tris, 20% sucrose, pH 8.0 and used to prepare an osmotic shock solution exactly as described in Current Protocols in Molecular Biology (Current Protocols, 16.6.7 alternative protocol). PMB extraction was performed on the other half of the pelleted cultures by first washing with PBS, resuspending them in 80 ml PBS, with 3.2 ml 50 mg/ml PMB (Sigma) added, and the solution was incubated 10 min on ice. The PMB extracted cells were then centrifuged 20 min at 11,000 xg. The supernatant compriseds the PMB extracted periplasmic extract.

C. ELISA Quantification of VT1 B and V2 B Subunits

Expression levels of VT1B or VT2B subunits in each of the extracts prepared above were quantified utilizing a quantitative ELISA protocol. In this procedure, 96-well microtiter plates (Falcon, Pro-Bind Assay Plates) were coated by placing 100 µl volumes of either mouse anti-VT1B (SLT 13C4 monoclonal; Toxin Technology) or mouse anti-VT2B (SLT 2B12 monoclonal; Toxin Technology) at 10 µg/ml in 100 mM sodium bicarbonate, pH 9.0, in each well and incubating overnight at room temperature. The next morning, the coating suspensions were decanted, and 100 µl of 1.0% gelatin (Sigma) in PBS (blocking solution) was then added to each well, and the plates were incubated for 1 hr. at room temperature. The blocking solution was decanted, the wells washed 2X with PBS+0.1% Tween-20, and duplicate samples of 100 µl of sample added to the first well of a dilution series, and 100 µl of ⅕ diluted sample were added to each subsequent dilution well. To produce a standard curve, 100 µl of a 2 fold serial dilution from 1–50 ng/ml of purified VT1B or VT2B subunit (his-tagged subunit material purified in as described in Example 8, with 2 $OD_{280}$/ml estimated to be 1 mg/ml) was added in duplicate to dilution wells. All dilutions were in sample dilution buffer (PBS+ 0.1% Tween-80, 0.1% gelatin, 0.5% BSA, 20% glycerol, 0.05% NaAzide). The plates were incubated 1 hr at room temperature. The protein solutions were decanted and the plates were washed 4X with PBS+0.5% Tween-20. Next, 100 µl/well of either ¹⁄₁₀₀₀ diluted chicken anti-VT1B 4X PEG preparation (for VT1B ELISA) or 1.5 µg/ml affinity purified chicken anti-VT2B (for VT2B ELISA) diluted in conjugate dilution buffer (PBS+0.1% Triton X100, 0.2% gelatin and 0.05% NaAzide) was added. After 30 min incubation at room temperature, the wells were washed 4X with PBS+0.5% Tween-20, and 100 µl/well of ¹⁄₁₀₀₀ diluted anti-chicken alkaline phosphatase conjugate (Sigma) in conjugate dilution buffer was added. After ½ hr at room temperature, the wells were washed 2 X PBS+0.5% Tween-20, then 2X PBS.

The plates were developed by the addition of 100 µl of a solution containing 1 mg/ml para-nitro phenyl phosphate (Sigma) dissolved in 50 mM $Na_2CO_3$, 10 mM $MgCl_2$ (pH 9.5), to each well, and incubating the plates at room temperature in the dark for 5–30 min. The absorbency of each well was measured at 410 nm using a plate reader (Dynatech MR 700). The concentration of verotoxin subunit in each unknown sample was estimated by comparison with the absorbance of the reference standard solution (at an antigen concentration in which the reference standard absorbance increased 2-fold with a 2-fold increase in concentration). The ELISA assays were specific to the relevant subunits, since 0 µg/ml concentrations were obtained when VT2B soluble lysates were read in the VT1B assay, or when VT1B soluble lysates are read in the VT2B assay. The estimated concentrations of the subunits for each expression system are shown in Table 14. In this Table, the concentrations listed are either VT1B (for VT1B row) or VT2B (for VT2B row) verotoxin protein.

TABLE 14

Subcellular Localization and Concentration of Verotoxin Subunit Expression

| Plasmid | Total cellular | Soluble cellular | Periplasm (Osmotic) | Periplasm (PMB) | Culture Soup |
|---|---|---|---|---|---|
| pET24T7VT1B | 0.8–1.5 mg/l | 0.8–1.5 mg/l | 1.2 mg/l | 0.14 mg/l | 0.16 mg/l |
| pET24VT2B | 3.0–7.5 mg/l | 3.0–7.5 mg/l | 1.2 mg/l | 0.7–1.75 mg/l | 2.5 mg/l |

This analysis demonstrated that the bulk of the expressed VT1B subunit was periplasmically located, and quantitatively released by osmotic shock but not PMB extraction. The VT2B subunit is both cell associated (of which approximately ½ is periplasmically localized) and secreted into the culture supernatant. Thus, successful purification strategies for isolation of these subunits were periplasmic protein preparations for VT1B, and either periplasmic, whole cell, or culture broth protein preparations for VT2B.

EXAMPLE 11

Fermentation Culture of the pET24VT2B BL21 (DE3) Cell Line

In this Example, large scale purification of the VT2B protein using a 10 liter fermentation of BL21(DE3) cells containing the pET24VT2B plasmid was performed.

The pET24VT2B plasmid was transformed into the BL21 (DE3) strain, and glycerol stocks prepared for use as seed stocks for fermentation cultures. A culture of the transformed recombinant was set up and grown to late log phase ($OD_{600}$=1.0–1.2) in LB broth. The bacteria were aseptically transferred to centrifuge bottles and centrifuged to pellet. The cells were resuspended in ¹⁄₂₀ of the original culture volume of fresh LB broth. Another ¹⁄₂₀ volume of fresh LB+20% glycerol was added and the suspension mixed and aliquoted into multiple 2.0 ml cryotubes. The cultures were allowed to equilibrate in the glycerol solution for 30 minutes at room temperature, then frozen at −70° C., for long term storage.

The fermentation was performed as follows. A Bioflo IV fermenter was sterilized 120 min at 121° C., with $dH_2O$. The sterile water was removed, and fermentation media added as follows:

6 liters nitrogen source (100 g yeast extract (BBL) and 200 g tryptone/3 liters (BBL)

2 liters 5X fermentation salts
(48.5 g $K_2HPO_4$, 12 gm $NaH_2PO_4.H_2O$, 5 gm $NH_4Cl$, 2.5 gm NaCl/liter)

2 liters 2% glucose 20 mls 1 M $MgSO_4$ 50 mls 0.05 M $CaCl_2$ 2.5–3.5 mls macol P 400 antifoam (PPG Industries Inc., Gurnee, Ill.)

40 mls 10 mg/ml kanamycin 10 mls trace elements
(8 g $FeSO_4.7H_2O$, 2 g $MnSO_4.H_2O$, 2 g $AlCl_3.6H_2O$, 0.8 g $CoCl.6H_2O$, 0.4 g $ZnSO_4.7H_2O$, 0.4 g $Na_2MoO_4.2H_2O$, 0.2 g $CuCl_2.2H_2O$, 0.2 g $NiCl_2$, and 0.1 g $H_3BO_4$/200 mls 5 M HCl)

All solutions were sterilized by autoclaving, except the kanamycin stock which was filter sterilized.

Next, 250 µl of glycerol stock was added to the fermenter. After seed innoculation, the culture was fermented at 30° C., 125 rpm agitation, and 10 l/min air sparging. The $DO_2$ control was set to 20% PID, and dissolved oxygen levels were controled by increasing aggitation from 125–850 rpm under $DO_2$ control. $DO_2$ levels were maintained at greater than or equal to 20% throughout the entire fermentation. Culture growth was continued until endogenous carbon sources were depleted (approximately 12–15 hrs). At this point, a fed batch mode was initiated, in which a feed solution of 50% glucose was added at a rate of approximately 4 gm glucose/liter/hr. The pH was adjusted to 7.0 by the addition of either 25% $H_3PO_4$ or 4 M NaOH solution. Antifoam (a 1:1 dilution with filter sterilized 100% ethanol) was added as necessary throughout the fermentation to prevent foaming. Induction with IPTG (4 g) was initiated 2 hrs 40 min after initiation of glucose feed. At 4 hrs post induction, the cells were cooled in the fermentor to 14° C., and stored overnight at 4° C. At the time of induction and at hourly intervals post induction, 5–10 ml aliquots of cells were harvested.

Optical density readings were determined by measurement of absorbance at 600 nM of 10 µl culture in 990 µl PBS versus a PBS control. The density readings of the culture were 47.5, 56, 58, 59, and 61.5, at 0–4 hrs post induction, respectively. Cells from each timepoint were serially diluted in PBS (diln 1=1µ 51 cells/3 ml PBS, diln 2=15 µl diln ⅓ ml PBS, diln 3=6 µl diln ⅔ mls PBS) and 100 µl diln 3 plated on an LB plate and incubated at 37° C. overnight. Cell counts were 154, 33 (3), 11 (1), 14 and 25 at 0–4 hrs post induction (bracketed cell counts represent microcolonies). Morphologically detectable contaminant colonies were not detected on any plate. LB plates from the uninduced timepoint were replica plated onto LB+kan, LB+kan+1 mM IPTG and LB plates, in this order. The cultures were grown 6–8 hrs at 37° C. and growth on each plate was scored. No colonies were detected on the IPTGKan plate (i.e., no mutations were detected) and 50/50 scored colonies were kan resistant (most cells retained plasmid at the time of induction).

EXAMPLE 12

Quantitative ELISA

In this Example, samples from Example 11 were prepared for quantitative ELISA determination of verotoxin concentration.

First, soluble extracts were prepared from 10 $OD_{600}$ units of cells at 0–4 hrs after induction, using cells removed for timepoint analysis, exactly as described in Example 10. An osmotic shock periplasmic extract from cells at 4 hrs post induction was also prepared as described in Example 10. Briefly, 50 mls of culture were pelleted by centrifugation 10 min max rpm in a benchtop centrifuge. The pellet was resuspended in 200 ml 30 mM Tris/20% sucrose pH 8.0 and osmotic shock solution prepared exactly as described in Example 10.

An unconcentrated culture supernatant ("unconcentrated culture soup") was also tested. After overnight storage at 4° C., cells were pelleted from the entire 10 liter fermentation harvest. This was performed by centrifugation at 12,000 xg for 10 min, and pooling the clarified culture broth. A 10 ml sample was filtered through a 3 μm filter; the filtered culture soup was the "unconcentrated culture supernatant" sample. Finally, a concentrated culture supernatant ("concentrated culture soup") was also tested. The 10 liter fermentation supernatant was filtered through a 1.0 μm (Ultipor; Pall) using a peristaltic pump. The supernatant was then filtered through a 0.2 μm filter (Ultipor; Pall). The resulting 8 l of cloudy brown supernatant was concentrated using a preparation-scale TFF 1 ft2 PLGL 10K regenerated cellulose cartridge (Millipore) connected to a peristaltic pump. Material was concentrated down to 0.8 l and washed with 2 l of PBS (pH 7.0). A sample of the diafiltration flow through was kept for analysis. The final concentrated material (650 mls) was aliquoted into 50 ml tubes (Falcon) and stored at −70° C. The final concentrated sample was the concentrated culture supernatant.

The VT2B concentration in each of these samples was determined by quantitative ELISA measurement as described in Example 10, and the resulting concentrations are shown in the following Table.

TABLE 15

VT2B Concentration in pET24VT2B Fermentation Samples

| Sample | VT2B Concentration |
|---|---|
| Total soluble extract: uninduced | 50 mg/l |
| Total soluble extract: 1 hr induction | 300 mg/l |
| Total soluble extract: 2 hr induction | 700 mg/l |
| Total soluble extract: 3 hr induction | 600 mg/l |
| Total soluble extract: 4 hr induction | 600 mg/l |
| Periplasmic extract | 100 mg/l |
| Unconcentrated culture soup | 750 mg/l |
| Concentrated culture soup | 9.4 gm/l |
| Culture soup diafiltration flow-through | 3 mg/l |

These results indicated that greater than 50% of the VT2B subunit at harvest was in the culture supernatant. The remainder was cell-associated, of which approximately 20% was periplasmically localized. The culture soup material was concentrated quantitatively by diafiltration (80% recovery of VT2B in final diafiltered concentrated sample). The losses at the concentration stage were due to diafilter retension, rather than flow through (only 3 mg/l VT2B in diafiltration flow through). The total yield of VT2B subunit in the concentrated culture supernatant was 6 g from the 10 liter fermentation (starting concentration was 7.5 g in 10 liters of unconcentrated culture supernatant). This demonstrated that gram quantities of VT2B subunit can be generated by fermentation culture of the pET24VT2B BL21(DE3) cell line.

The final concentrated culture supernatant contained 9.4 mg/ml VT2B, but was heavily discolored with brown material. This colored material is removed by polyethylenimine (PEI) clarification. To 24 mls concentrated culture supernatant 2.7 ml of 2% PEI solution (Mallinkrodt; 2% solution in dH$_2$O, pH 7.5 with HCl) was added, the solution mixed 30 min on vibrax and centrifuged 3200 xg for 45 min. The concentration of VT2B in the PEI clarified culture soup was estimated to be 7.3 mg/ml by quantitative ELISA. Thus, PEI clarification can be utilized to remove impurities from the culture supernatant without precipitating the VT2B subunit from solution.

EXAMPLE 13

Purification of Native VT2B Subunit

In this Example, native VT2B was purified. A PEI clarified, concentrated culture supernatant containing native (nontagged) VT2B was prepared as in Example 12. A 30 ml aliquot of the supernatant was filtered through a Gelman glass fiber Acrodisc 4524 filter, and transferred to Spectra/Por 3 dialysis tubing (MWCO 3,500). The material was dialyzed with mixing one time, overnight, at ambient temperature against 1.5 L of 20 mM sodium phosphate, 0.025% sodium azide, 0.1% Tween 20, pH 7.0.

A 1.5 cm×14 cm column containing Whatman Express-Ion Exchanger C (CM cellulose) was equilibrated with 20 mM sodium phosphate, 0.025% sodium azide, 0.1% Tween 20, pH 7.0. The flow rate was constant at 2 ml/minute throughout the following procedure. A 20 ml aliquot of the dialyzed, PEI clarified concentrate containing VT2B was loaded onto the column. The column was washed with 20 mM sodium phosphate, 0.025% sodium azide, 0.1% Tween 20, pH 7.0. The flow-through and wash were collected (59 ml). The material loaded on the column and the flow-through and wash were assayed by the VT2B Quantitative ELISA as described in Example 10. All of the VT2B loaded onto the column (approximately 150 mg) was in the flow-through and wash. The VT2B was thus partially purified, as many contaminants bound to the Express-Ion Exchanger C column and were separated from the VT2B.

A 20 ml sample of the Ion Exchanger C flow-through and wash was loaded onto a 1.5×16.5 cm column of Whatman Express-Ion Exchanger Q (QAE cellulose) equilibrated with Buffer A (20 mM sodium phosphate, pH 7.0. 0.025% sodium azide, 10% glycerol, containing 0.1% each Tween 20, Tween 80 and Hecameg). The flow rate was 2.0 ml/minute throughout this procedure. Absorbance at 280 nm was monitored. The column was washed for 15 minutes with Buffer A, followed by a linear gradient from 0% Buffer B to 100% Buffer B over 65 minutes. Buffer B was the same as Buffer A, with the exception that it included 1.5 M sodium chloride.

The chromatogram was characterized by the following A$_{280}$ absorbing material: the flow-through, a small 26 minute peak from 25 to 27 minutes, and a large 36 minute peak from 34 to 39 minutes. These three fractions were collected and analyzed in the VT2B Quantitative ELISA, as described in Example 10, and by SDS PAGE (20% polyacrylamide).

The ELISA results indicated that there was no VT2B activity in the flow-through or in the small 26 minute peak. However, VT2B activity was found in the 36 minute peak. The purity of the partially purified VT2B was estimated to be 60% on SDS PAGE.

EXAMPLE 14

Generation of Verotoxin Subunit Immunogens

In this Example, subunit specific antiserum was generated utilizing purified recombinant verotoxin subunits. As indicated above, the B subunits associate to form a pentamer, and this pentameric conformation was thought to be important for the generation of neutralizing antibodies. Since the VT2B pentamers may be unstable when expressed without the A subunit (See, Acheson et al., Infect. Immun., 63:301 [1995]), crosslinking was utilized to prevent subunit dissociation. The antigens that were utilized for immunization are summarized in the following Table. In all cases, the antigens utilized for immunization are from the recombinant protein preparations described in Examples 6–13.

TABLE 16

Protein Preparations for Immunization

| Verotoxin Subunit | Expression Vector | Protein Description | Gluteraldehyde Cross-Linked |
|---|---|---|---|
| VT1A | pMalVT1A | MBPVT1A | No |
| VT2A | pMalVT2A | MBPVT2A | No |
| VT1B (His) | pET23HisVT1BL+ and pET24HisVT1BL+ | VT1B (His-tag) | No |
| VT2B (His) | pET23HisVT2BL+ and pET24HisVT2BL+ | VT2B (His-tag) | No |
| VT2B (His + Cross-linked) | pET24HisVT2BL+ | VT2B (His-tag) | Yes |
| VT2B (Native) | pET24VT2B | VT2B (Native) | No |
| VT2B (Native + Cross-linked) | pET24VT2B | VT2B (Native) | Yes |

Cross-linking was performed with gluteraldehyde as described below. For VT2B (His) cross-linking, 10 mls of a 1 mg/ml VT2B(His) protein preparation (in imidazole elution buffer (See e.g., Example 8) was dialysed three times for 2 hrs versus a 100-fold excess of PBS utilizing a Pierce 10 K Slide-A-Lyser cassette. To 10 mls of dialysed protein 1/10 volume (1 ml) of 1% glutaraldehyde (Mallinkrodt) was added, the solution stirred 5 min, and then left overnight at room temperature. The sample was dialysed 2X versus 100 volumes of PBS+thimerisol for greater than 6 hrs each dialysis, utilizing a Pierce 10 K Slide-A-Lyser cassette. The final dialysed sample was stored at 4° C.

For VT2B (Native) cross-linking, 10 mls of the concentrated culture supernatant (Example 12) was centrifuged 30 min at 40,000 xg to pellet insoluble material. The supernatant was dialysed three times for 2 hrs versus a 100-fold excess of PBS utilizing a Pierce 10 K Slide-A-Lyser cassette. To 10 mls of dialysed protein 1/10 volume (1 ml) of 1% glutaraldehyde (Mallinkrodt) was added, the solution stirred 5 min, and then left overnight at room temperature. The sample was dialysed 2X versus 100 volumes of PBS+ thimerisol for greater than 6 hrs each dialysis utilizing a Pierce 10 K Slide-A-Lyser cassette. The final dialysed sample was stored at 4° C.

Samples of untreated and cross-linked material were resolved on a 20% SDS-PAGE gel and Coomassie stained.

The results (not shown) demonstrated successful cross-linking of the VT2B subunits (both his and native subunits). The results also indicate that the concentrated culture supernatant is highly enriched for the VT2B subunit, as this is the predominant protein band in the sample.

EXAMPLE 15

Immunization with Recombinant Verotoxin Subunits

In this Example, hens were immunized with purified recombinant subunit immunogens. Eight groups of white Leghorn laying hens were injected subcutaneously with 0.2–0.3 mg recombinant verotoxin subunits (pET23hisVT1BL+, pET23hisVTLBL+, pMalVT1A and pMal VT2A[BamHI]), mixed with 5 μg Gerbu, or 75 μg QuilA adjuvants at 2–3 week intervals.

Eggs were collected from the hens after three or more immunizations with verotoxin subunits. Egg yolks were separated from whites, pooled and blended with four volumes of 10 mM sodium phosphate, 150 mM NaCl, pH 7.4 (PBS). Solid polyethylene glycol 8000 (PEG) was then added with mixing, to a final concentration of 3.5% and the mixture was centrifuged at 10,000 xg for 10 minutes. The supernatant was filtered though cheesecloth and PEG was again added to a final concentration of 12% to precipitate the IgY. The solution was centrifuged as above and the resulting supernatant discarded. The pellet contained the IgY and was dissolved in PBS to either the original yolk volume (1X PEG IgY) which contained approximately 5 mg/ml IgY or ¼ of the original yolk volume (4X PEG IgY) which contained approximately 20 mg/ml. The resuspended IgY was then filtered though a 0.45μ membrane and stored at 4° C. As a control, eggs from nonimmunized hens or preimmune (PI) hens were harvested and IgY extracted as descibed above.

To distinguish antibody groups, IgY was named with the antigen followed by the initial of the adjuvant used (e.g., "VT1A-G IgY" is antibody produced by hens immunizaed with VT1A using Gerbu adjuvant, whereas "VT1A-Q IgY" was produced by hens immunized with VT1A using Quil-A).

ELISAs were used to monitor antibody response during the course of immunization. IgY's from all immunogen groups were tested against rVTs. Wells of a microtiter plate were coated with 2.5 μg/ml of rVT's in PBS overnight at 2–80° C. Wells were washed 3 times with PBS containing 0.05% Tween-20 (PBS-T), and blocked with PBS containing 5 mg/ml BSA for 1 hour at room temperature. 1X PEG IgY from hyperimmune, preimmune eggs and hens immunized with toxoid produced from rVT holotoxin (postive control) was diluted in PBS containing 1 mg/ml BSA, added to the wells, and incubated for 1 hr at 37° C. Wells were washed as before, and incubated for 1 hr at 37° C. with alkaline phosphatase-conjugated rabbit anti-chicken antibody diluted 1:1000 in PBS-T. Wells were washed again and 1 mg/ml p-nitrophenyl phosphate in 50 mM $Na_2CO_3$, 10 mM $MgCl_2$ (pH 9.5), was added and allowed to incubate at room temperature. Phosphatase activity was detected by absorbance at 410 nm using a Dynatech MR700 microtitier plate reader.

The validity of each ELISA assay was demonstrated with a positive control using rVT IgY and negative controls using Preimmune (PI) IgY. The results are given in FIGS. 10–13. VT1 IgY is included in the figures as a positive control. Preimmune (PI) IgY is included in the figures as a negative control. Titer is defined as binding activity twice as high as PI levels.

FIG. 10 shows the relatively strong binding of VT1 A-G IgY and VT1 A-Q IgY to the homologous toxin rVT1, with titers of 1:6000 and 1:1200 respectively. There was essentially no cross-reactivity of VT2 A-G IgY and VT2-A-Q IgY to VT1 holotoxin.

As shown in FIG. 11, VT1 A-G IgY and VT1 A-Q IgY cross-reacted strongly to rVT2; both gave a titer of 1:1200 against rVT2. However the signal from VT1A-Q IgY was much stronger at the higher concentrations. In contrast, homologous VT2A-Q IgY reactivity to rVT2 gave a much weaker response with a titer of 1:250 and VT2A-G IgY did not react over PI levels.

FIG. 12 demonstrates the binding of VT1B-G IgY and VT1B-Q IgY to rVT1 was similar with titers of 1:500 each. Heterologous VT2B-G IgY bound poorly with a titer of 1:100 while VT2B-Q IgY had a high titer of 1:1:2500 to rVT1.

FIG. 13 shows moderate cross-reactivity of VT1B-G IgY and VT1B-Q IgY to VT2, both gave titers of 1:500 and 2500, respectively. Strong reactivity with a titer of 2500 was seen using homologous VT2B-Q IgY to VT2 while VT2B-G IgY showed no significant binding at 1:100.

In summary, VT1A IgY, VT1B IgY, and VT2B IgY reacted with both VT1 and VT2, (i.e., they cross-react). VT2A IgY reacted only with VT2 holotoxin. Overall, antibodies from animals immunized with QuilA performed better than those from animals immunized with Gerbu. In addition, QuilA is a more economical adjuvant, costing approximately 5 times less per immunization than Gerbu.

EXAMPLE 16

Toxin Neutralization

Challenge in Mice

In this Example, protection experiments were performed in mice, in a manner similar to that of Example 5. Two aspects of this experiment are included, the Toxin Challenge Model and the Viable Organism Infection Model.

A. Toxin Challenge Model rVT1 or rVT2 was premixed with IgY and injected into mice to determine whether toxin could be neutralized. Tables 17–23 show the results of rTV1 neutralization studies. VT1A-G IgY, VT1A-Q IgY, and VT1B-Q IgY all successfully neutralized rTV1. VT2A-G IgY, VT2A-Q IgY, VT1B-G IgY, and VT2B-Q IgY did not protect the mice. Tables 24–27 summarize the rVT2 neutralization studies. Only VT2B-Q IgY was capable of preventing lethality by rVT2. The other antibodies tested, VT1A-G IgY, VT1A-Q IgY, VT2A-G IgY, and VT2B-Q IgY were unable to neutralize the toxin. Therefore neutralizing antibodies to both toxins were generated, though no cross-neutralization was found. In this table, "N.S." indicates that there were no statistically significant differences (Chi-square analysis).

TABLE 17

Neutralization of rVT1 Using VT1A-G IgY and VT1-Q IgY IgY

| Antibody Tested | Results of Individual Trials #survivors/#total | Sum of All Trials #Survivors/#Total | p |
|---|---|---|---|
| Preimmune Antibody | 0/6 3/7 | 3/13 | |
| VT1A-G IgY | 7/7 7/7 | 14/14 | <.001 |
| VT1A-Q IgY | 6/6 5/7 | 11/13 | <.01 |

TABLE 18

Neutralization of rVT1 Using VT2A-G IgY

| Antibody Tested | #Survivors/#Total | p |
|---|---|---|
| Preimmune IgY | 0/6 | |
| VT2A-G IgY | 1/6 | N.S. |

TABLE 19

Neutralization of rVT1 Using VT2A-Q IgY

| Antibody Tested | #Survivors/#Total | p |
|---|---|---|
| Preimmune IgY | 3/7 | |
| VT2A-Q IgY | 2/7 | N.S. |

TABLE 20

Results for VT1B-Q IgY

| Antibody Tested | #Survivors/#Total | p |
|---|---|---|
| Preimmune IgY | 3/7 | |
| T1B-G IgY | 7/7 | N.S. |

While the results in Table 20 indicate no statistically significant difference, it is assumed from the successful neutralization of anti-VT1B-Q, that anti-VTB-G should be effective.

TABLE 21

Neutralization of rVT1 Using VT1B-Q IgY

| Antibody Tested | Results of Individual Trials #survivors/#total | Sum of All Trials #Survivors/#Total | p |
|---|---|---|---|
| Preimmune IgY | 3/9 | 3/14 | |
| VT1B-Q IgY | 9/9 | 14/14 | <0.001 |

TABLE 22

Neutralization of rVT1 Using VT2B-G IgY

| Antibody Tested | #Survivors/#Total | p |
|---|---|---|
| Preimmune IgY | 3/7 | |
| VT2B-G IgY | 2/7 | N.S. |

TABLE 23

Neutralization of rVT1 Using VT2B-Q IgY

| Antibody Tested | Results of Individual Trials #Survivors/#Total | Sum of All Trials #Survivors/#Total | p |
|---|---|---|---|
| Preimmune IgY | 2/7 1/7 | 3/14 | |
| VT2B-Q IgY | 3/7 0/7 | 3/14 | N.S. |

TABLE 24

Neutralization of rVT2 Using VT1A-G IgY

| Antibody Tested | Results of Individual Trials #Survivors/#Total | p |
|---|---|---|
| Preimmune IgY | 4/7 | |
| VT1A-G IgY | 3/6 | N.S. |

TABLE 25

Neutralization of rVT2 Using VT1A-Q IgY

| Antibody Tested | #Survivors/#Total | p |
|---|---|---|
| Preimmune IgY | 1/7 | |
| VT1A-Q IgY | 2/7 | N.S. |

TABLE 26

Neutralization of rVT2 Using VT2A-G IgY

| Antibody Tested | Results of Individual Trials #Survivors/#Total | Sum of All Trials #Survivors/#Total | p |
|---|---|---|---|
| Preimmune IgY | 4/7 1/7 | 5/14 | |
| VT2A-G IgY | 2/6 2/7 | 4/13 | N.S. |

TABLE 27

Neutralization of rVT2 Using VT1B-Q IgY and VT2B-Q IgY

| Antibody Tested | Results of Individual Trials #Survivors/#Total | Sum of All Trials #Survivors/#Total | p |
|---|---|---|---|
| Preimmune IgY | 1/7 | 1/7 | |
| VT1B-Q IgY | 0/7 | 0/7 | N.S. |
| VT2B-Q IgY | 7/7 | 7/7 | <0.01 |

B. Viable Organism Infection Model

The toxin neutralizing ability of VT IgY was further demonstrated in an infection study. This experiment was performed as described in Example 5. In this Example, mice were infected with either E. coli O91:H21 (strain B2F1) Because the infecting organism produces a variant of VT2 (i.e., VT2c), only antibodies demonstrating neutralizing ability to VT2 toxin in vitro were tested. For the results shown in Table 28, IgY was administered intraperitoneally at 4 and 10 hours post-infection and once a day thereafter for the next three days. For the results shown in Table 29, IgY was administered intraperitoneally at 4 hours post-infection and once a day thereafter for the next three days.

The results shown in Tables 28 and 29 demonstrate that the VT2B-Q IgY protected mice from lethality when administered 4 hrs following infection (the longest treatment window tested) and that preimmune IgY was unable to protect the animals.

These results indicated that IgY capable of neutralizing VT2 was generated and therefore, the VT2B-Q IgY provides therapeutic benefit for the treatment of VTEC infections.

TABLE 28

Protection of Mice from E. coli O91:H21 with VT2B-Q IgY

| IgY Treatment | Survivors/Total | p |
|---|---|---|
| Preimmune Antibody | 2/10 | |
| VT2B-Q IgY | 8/10 | <0.05 |

TABLE 29

Protection of Mice from E. Coli 091:H21 with VT2B-Q IgY

| IgY Treatment | Survivors/Total | p |
|---|---|---|
| Preimmune Antibody | 0/10 | |
| VT2B-Q IgY | 9/10 | <0.001 |

EXAMPLE 17

Anti-Verotoxin Production in Rabbits

In this Example, rabbits were used to produce neutralizing antibodies against VT1 and VT2.

Purified VT1B (pET24hisVT1BL+), VT2B (pET24hisVT2BL+), VT2A (pMalVT2A[BamHI]), VT2B (His+Cross-linked), VT2B(Native+Cross-linked), and VT2B (Native, concentrated) were used as immunogens in this experiment. As with earler examples, to distinguish antibody groups, IgY was named with the antigen follwed by the initial adjuvant used (e.g., "VT1A-G Ig" is antibody produced by rabbits immunized with VT1A using Gerbu adjuvant, and "VT1A-A.Ig" is antibody produced by rabbits immunized with VT1A using alum adjuvant). These antigens were prepared as listed in Table 16, with the exception being rVT1A, which was not used.

A group of New Zealand rabbits were immunized IM a one site with 500 µg VT1B and VT2B, mixed with 10 µg Gerbu, or an equal volume of alum. One month later, the rabbits were boosted, by reinjecting in the same manner. Two weeks after the boots, the rabbits were bled. The blood was sera stored at 37° C. for 1 hour, and centrifuged. The sera were collected, and stored at −20° C. until testing, as described below.

A second group of rabbits was initially immunized ID, in at least 20 sites with 300 µg VT2B (His+Cross-linked), VT2B (Native+Cross-linked), and VT2B (Native), with 100 µg QuilA, or an equal amount of alum. Another group of rabbits was immunized with 90 µg of VT2A and the same volumes of adjuvant as described above. One month after primary immunization, the rabbits were boosted SC, and were bled two weeks after the boost. These sera were collected and stored as described above.

EXAMPLE 18

ELISA Testing of Rabbit Sera

In this Example, the sera collected from the rabbits described in Example 17 were tested in an ELISA. In this experiment, the ELISA methods used in previous examples (See, Example 10) were used, with the exception being that the primary antibody was rabbit sera and the secondary antibody was goat anti-rabbit (1:1500 dilution).

The focus of this Example, were ELISAs that tested the binding ability of Ig to native toxin. Only VT1B-A Ig, and VT1B-G Ig reacted to rVT1 at dilutions of 1:2500. Neither VT2B-A Ig, VT2B-G Ig, nor preimmune Ig reacted with rVT1 at a dilution greater than 1:100. For rVT2, only VT1B-A Ig showed a specific antibody response, with the Ig reacting at a dilution of 1:2500.

EXAMPLE 19

Toxin Challenger Model

In this Example, the ability of rabbit Ig produced as described in Example 17 was tested for its ability to protect mice from the effects of verotoxin.

Sera was premixed with a lethal dose of toxin (lethal dose was determined as described in Ex. 1D). This preparation was then injected IP into mice. The mice were observed for seven days post injection as described in Ex. 5A. The results are summarized in Tables 30–33.

The results shown in Table 30 indicate that both VT1B-A Ig and VT1B-G Ig completely protected the mice against rVT1 when tested in the system shown in the table. However, VT2B-A Ig did not protect the mice from lethality. The results in Table 31 show that none of the antibodies tested as shown in this table protected against rVT2. The results in Table 32 show that VT2B(His+Cross-linked) Ig, VT2B(Native+Cross-linked) Ig, completely neutralized rVT2, regardless of the adjuvant used. In addition, VT2A Ig provided some protection. The results in Table 33 show that neither VT2B(native)-A Ig, nor VT2B(Native)-Q Ig provided statistically significant protection against rVT2.

TABLE 30

3 $LD_{50}$ rVT1 Premixed with Serum (Final Dilution 1:100)

| Antibody Tested | # Survivors/# Total |
|---|---|
| Preimmune Ig | 1/14 |
| VT1B-A Ig | 14/14 |
| VT1B-G Ig | 14/14 |
| VT2B-A Ig | 2/7 |

TABLE 31

7 $LD_{50}$s of rVT2 Premixed with Serum (Final Dilution 1:100)

| Antibody Tested | # Survivors/# Total |
|---|---|
| Preimmune Ig | 1/14 |
| VT1B-A Ig | 0/14 |
| VT1B-G Ig | 2/14 |
| VT2B-A Ig | 1/14 |
| VT2B-G Ig | 3/14 |

TABLE 32

3 $LD_{50}$s of rVT1 Premixed with Serum (Final Dilution 1:100)

| Antibody Tested | # Survivors/# Total |
|---|---|
| Preimmune Ig | 3/7 |
| VT2B(His + Cross-linked)-A Ig | 2/7 |
| VT2B(His + Cross-linked)-Q Ig | 2/7 |
| VT2B(Native + Cross-linked)-A Ig | 0/7 |
| VT2B(Native + Cross-linked)-Q Ig | 3/7 |
| VT2A-A Ig | 4/7 |
| VT2A-Q Ig | 4/7 |

TABLE 33

7 $LD_{50}$s of rVT2 Premixed with Serum (Final Dilution 1:100)

| Antibody Tested | # Survivors/# Total |
|---|---|
| Preimmune Ig | 0/7 |
| VT2B(His + Cross-linked)-A Ig | 7/7 |
| VT2B(His + Cross-linked)-Q Ig | 7/7 |
| VT2B(Native + Cross-linked)-A Ig | 7/7 |
| VT2B(Native + Cross-linked)-Q Ig | 7/7 |
| VT2A-A Ig | 5/7 |
| VT2A-Q Ig | 3/7 |

TABLE 34

7 LD$_{50}$ rVT2 Premixed with Serum (Final Dilution 1:100)

| Antibody Tested | # Survivors/# Total |
|---|---|
| Preimmune Ig | 1/6 |
| VT2B(Native)-A Ig | 5/6 |
| VT2B(Native)-Q Ig | 4/6 |

EXAMPLE 20 rVT2B Column

In this Example, rVT2B was covalently attached to an aldehyde activated agarose matrix. One ml VT2B was mixed with 50 μl Actigel resin (Sterogene), and 200 μl of coupling solution (Sterogene). The mixture was incuabed overnight with agitation and poured into a column. The column was equilibrated with PBS containing 0.005% thimerosol. Fifty-five ml of a VT2B-Q IgY PEG preparation or a VT2B-G IgY PEG preparation prepared as described above were applied to the column. The flow-through was collected and reloaded onto the column. The column was then washed with PBS containing 0.005% thimerosol until baseline was re-established. Bound antibody was eluted from the column in Actisep elution buffer (Sterogene), and the elution peak was collected. The column was re-equilibrated.

Affinity-purified specific antibodies were dialyzed against three changes of a 130-fold volume of PBC 4° C. The percentage of specific VT2B IgY present in each preparation was determined using UV absorbance and expressed as a percentage of total protein in the preparation. Purification of VT2B-Q IgY yielded 0.6% specific antibody and purification of VT2B-G IgY was approximately 0.2% specific antibody.

From the above, it is clear that the present invention provides compositions and methods for the preparation of effective multivalent vaccines against *Escherichia coli* verotoxins. It is also contemplated that the recombinant verotoxin proteins be used for the production of antitoxins. All publications and patents mentioned in the above specification are herein incorporated by reference. Various modifications and variations of the described method and system of the invention will be apparent to those skilled in the art without departing from the scope and spirit of the invention.

What is claimed is:

1. A bacterial host cell expressing a recombinant expression vector, said vector encoding a polyhistidine affinity tag and a protein comprising at least a portion of a bacterial toxin comprising *Escherichia coli* type 2 verotoxin, wherein said vector is selected from the group consisting of pET24hisVT2BL+, pET24hisVT2BL−, and pET24VT2B, wherein said protein is expressed as a soluble protein at a level of at least 40 milligram per 1 OD of said host cells per liter.

2. The bacterial host cell of claim 1, wherein said vector is selected from the group consisting of pET24hisVT2BL+ and pET24VT2B, and wherein said protein is expressed as a soluble protein at a level of at least 50 milligrams per 1 OD of said host cells per liter.

* * * * *